US007067281B2

(12) United States Patent
Korneluk et al.

(10) Patent No.: US 7,067,281 B2
(45) Date of Patent: *Jun. 27, 2006

(54) MAMMALIAN IAP GENE FAMILY, PRIMERS, PROBES AND DETECTION METHODS

(75) Inventors: Robert G. Korneluk, Ottawa (CA); Alexander E. MacKenzie, Ottawa (CA); Stephen Baird, Ottawa (CA); Peter Liston, Ottawa (CA)

(73) Assignee: Aegera Therapeutics, Inc., Verdun (CA)

( * ) Notice: Subject to any disclaimer, the term of this patent is extended or adjusted under 35 U.S.C. 154(b) by 90 days.

This patent is subject to a terminal disclaimer.

(21) Appl. No.: 10/600,272

(22) Filed: Jun. 20, 2003

(65) Prior Publication Data

US 2004/0157232 A1    Aug. 12, 2004

Related U.S. Application Data

(63) Continuation of application No. 09/011,356, filed on Sep. 14, 1998, now Pat. No. 6,656,704, which is a continuation-in-part of application No. 08/576,956, filed on Dec. 22, 1995, now Pat. No. 6,156,535, which is a continuation-in-part of application No. 08/511,485, filed on Aug. 4, 1995, now Pat. No. 5,919,912.

(51) Int. Cl.
*C12P 21/06* (2006.01)
*C12N 5/00* (2006.01)
*C12N 15/63* (2006.01)
*C07K 1/00* (2006.01)

(52) U.S. Cl. .................. 435/69.1; 435/320.1; 435/325; 435/455; 530/300; 530/350; 530/351; 536/23.1; 536/23.5

(58) Field of Classification Search .............. 435/69.1, 435/320.1, 325, 455; 530/350, 300, 351; 536/23.1, 23.5
See application file for complete search history.

(56) References Cited

U.S. PATENT DOCUMENTS

| 5,691,179 A | 11/1997 | Korsmeyer | 435/240.1 |
| 5,770,690 A | 6/1998 | Bitler et al. | 530/324 |
| 6,187,557 B1 | 2/2001 | Rothe et al. | 435/69.1 |

FOREIGN PATENT DOCUMENTS

| WO | WO 94/06814 | 3/1994 |
| WO | WO 95/19431 | 7/1995 |
| WO | WO 95/28497 | 10/1995 |
| WO | WO 97/06182 | 2/1997 |

OTHER PUBLICATIONS

Deveraux et al Gene & Dev. 13(3): 239-252, 1999.*
Ngo, in The Protein Folding Problem and Tertiary Structure Prediction, Merz et al. (eds.), Birkhauser Boston: Boston, MA, pp. 433 and 492-495, 1994.*
Rudinger, in Peptide Hormones, Parsons (ed.), University Park Press: Baltimore, MD, pp. 1-7, 1976.*
Accession S69544, Q13490, Q13489, S68451, HSU45878.
Birnbaum et al., "An apoptosis-inhibiting gene from a nuclear polyhedrosis virus encoding a polypeptide with Cys/His sequence motifs" *J. of Virol.* 68:2521 (1994).
Cameron, "Recent advances in transgenic technology" *Molecular Biotechnology* 7:253 (1997).
Campbell, *Monoclonal Antibody Technology* Elsevier Science Publishers B.V. N.Y. NY. (1984).
Clem et al., "Induction and inhibition of apoptosis by insect viruses" *Apoptosis II: The Molecular Basis of Apoptosis in Disease* Cold Spring Harbor Laboratory Press, p. 89 (1994).
Clem et al., "Anti-apoptotic genes of baculovirus" *Cell Death and Differentiation* 3:9 (1996).
Clem et al., "Prevention of apoptosis by a baculovirus gene during infection of insect cells" *Science* 254:1388 (1991).
Clem et al., "Control of programmed cell death by the baculovirus genes p35 and iap" *Mol. and Cell. Biology* 14:5212 (1994).
Crook et al., "An apoptosis-inhibiting baculovirus gene with a zinc finger-like motif" *J. of Virol.* 67:2168 (1993).
Dhein et al., "Autocrine T-cells suicide mediated by APO-1(Fas/CD95)" Abstract, *Nature* 373:438 (1995).
Duckett et al., "A conserved family of cellular genes related to the baculovirus iap gene and encoding apoptosis inhibitors" *The EMBO Journal* 15:2685 (1996).
Dupressoir et al., *Molecular Cell Biology* 16:4495 (1986).
Eck et al., *Goodman's and Gilman's the pharmacological basis of therapeutics* Chapter 5,9th Ed. 77-101 (1995).
Fernandez et al., "Differential sensitivity of normal and Ha-ras-transformed C3H mouse embryo fibroblasts to tumor necrosis factor: . . . " Abstract, *Oncogene* 9:2009 (1994).
Ferrari et al., "N-acetylcysteine (D- and L-stereoisomers) prevents apoptotic death of neuronal cells" Abstract, *J. Neurosci.* 1516:2857 (1995).

(Continued)

*Primary Examiner*—Sumesh Kaushal
(74) *Attorney, Agent, or Firm*—Kristina Bieker-Brady; Clark & Elbing LLP

(57) ABSTRACT

Disclosed is substantially pure DNA encoding mammalian IAP polypeptides; substantially pure polypeptides; and methods of using such DNA to express the IAP polypeptides in cells and animals to inhibit apoptosis. Also disclosed are conserved regions characteristic of the IAP family and primers and probes for the identification and isolation of additional IAP genes. In addition, methods for treating diseases and disorders involving apoptosis are provided.

9 Claims, 61 Drawing Sheets

OTHER PUBLICATIONS

Fisher et al., "Dominant interfering Fas gene mutations impair apoptosis in a human autoimmune lymphoproliferative syndrome" *Cell* 81:935 (1995).
Gibellini et al., "Tat-expressioon Jurkat cells show an increased resistance to different apoptic stimuli . . . "Abstract, *Br. J. Haematol* 89:24 (1995).
Golstein et al., "Homology between reaper and the cell death domains of Fas and TNFR1" *Cell* 81:185 (1995).
Goruppi et al., "Dissection of c-myc domains involved in S phase induction of N1H3T3 fibroblasts" Abstract, *Oncogene* 9:1537 (1994).
Harlow et al., *Antibodies: A laboratory manual* Cold Spring Harbor Laboratory, p. 76 (1989).
Harrington et al., "c-Myc-induced apoptosis in fibroblasts is inherited by specific cytokines" Abstract, *EMBO J.* 13:3286 (1994).
Itoh et al., "A novel protein required for apoptosis . . . " Abstract, *J. Biol. Chem.* 268:10932 (1993).
J. Kerr, "Neglected opportunities in apoptosis research" *Trends in Cell Biology* 5:55 (1995).
Katsikis et al., "Fas antigen stimulation induces marked apoptosis of T lymphocytes in human immunodeficiency virus-infected individuals" Abstract, *J. Exp. Med.* 1815:2029 (1995).
Korsmeyer, "Regulators of cell death" *TIG* 11:101 (1995).
Lerner, "Tapping the immunological repertoire to produce antibodies of predetermined specificity" *Nature* 299:592 (1982).
Li et al., "Induction of apoptosis in uninfected lymphocytes by HIV-1 Tat protein" Abstract, *Science* 268:429 (1995).
Liston et al., "Suppression of apoptosis in mammalian cells by NAIP and a related family of IAP genes" *Nature* 379:349 (1996).
Martin et al., "HIV-1 infection of human CD4+ T cells in vitro . . . " Abstract, *J. Immunol.* 152:330 (1994).
Melino et al., "Tissue transglutaminase and apoptosis: sense and antisense transfection studies . . . " Abstract, *Mol. Cell. Biol.* 14:6584 (1994).
Mulligan, *Science* 260:926 (1993).
Muro-Cacho et al., "Analysis of apoptosis in lymph nodes of HIV-infected persons . . . " Abstract, *J. Immunol.* 154:5555 (1995).
Nagata et al., "The FAS death factor" *Science* 267:1449 (1995).
Nunez et al., "The Bcl-2 family of proteins: regulators of cell death and survival" *Trends in Cell Biology* 4:399 (1994).
Orkin et al., "Report and recommendations of the panel to access the NIH investment in research on gene therapy" (1995).
Osborne et al., "Essential genes that regulate apoptosis" *Trends in Cell Biology* 4:394 (1994).
Rabizadeh et al., "Expression of the baculovirus p35 gene inhibits mammalian neural cell death" Abstract, *J. Neurochem.* 61:2318 (1993).
Rieux-Laucat et al., "Mutations in Fas associated with human lymphoproliferative syndrome and autoimmunity" *Science* 268:1347 (1995).
Rosenbaum et al., "Evidence for hypoxia-induced, programmed cell death of cultured neurons" Abstract, *Ann. Neurol.* 36:864 (1994).
Rothe et al., "The TNFR2-TRAF Signaling Complex Contains Two Novel Proteins Related to Baculoviral Inhibitor of Apoptosis Proteins" *Cell* 83:1243 (1995).
Roy et al., "The gene for neuronal apoptosis inhibitory protein is partially deleted in individuals with spinal muscular atrophy" *Cell* 80:167 (1995).
Sato et al., "Neuronal differentiation of PC12 cells as a result of prevention of cell death by bcl-2" Abstract, *J. Neurobiol.* 25:1227 (1994).
Steller, "Mechanisms and genes of cellular suicide" *Science* 267:1445 (1995).
Talley et al., "Tumor necrosis factor alpha-induced apoptosis in human neuronal cells: . . . " Abstract, *Mol. Cell. Biol.* 1585:2359 (1995).
Terai et al., "Apoptosis as a mechanism of cell death in cultured T lymphoblasts acutely infected with HIV-1" Abstact, *J. Clin. Invest* 87:1710 (1991).
Vossbeck et al., "Direct transforming activity of TGF-beta on rat fibroblasts", Abstract, *Int. J. Cancer* 61:92, (1995).
Westendorp et al., "Sensitization of T cells to CD95-mediated apoptosis by HIV-1 Tat and gp120" *Nature* 375:497 (1995).
Walkinshaw et al., "Induction of apoptosis in catecholaminergic PC12 cells by L-DOPA . . . " Abstract, *J. Clin. Invest.* 95:2458 (1995).
White et al., "Genetic control of programmed cell death in drosophila" *Science* 264:677 (1994).
Williams et al., "Apoptosis: final control point in cell biology" *Trends in Cell Biology* 2:263 (1992).
Wyllie, "Death gets a brake" *Nature* 369:272 (1994).

* cited by examiner

HUMAN xiap

```
SEQ ID NO:3        1 gaaaaggtggacaagtcctaattcaagagaagatgactttaacagtttgaaggatct   60
                     -----+----+----+----+----+----+----+----+----+----+----+
SEQ ID NO:4                                             M  T  F  N  S  F  E  G  S 61 aaaacttgtacctgtgcagacatcaataaggaagaagaatttgtagaagagtttaataga  120
                     -----+----+----+----+----+----+----+----+----+----+----+
                      K  T  C  V  P  A  D  I  N  K  E  E  E  F  V  E  E  F  N  R 121 ttaaaaacttttgctaatttccaagtggtagtcctgtttcagcatcaacactggcacga   180
                     -----+----+----+----+----+----+----+----+----+----+----+
                      L  K  T  F  A  N  F  P  S  G  S  P  V  S  A  S  T  L  A  R 181 gcagggtttctttatactggtgaaggagataccgtgcggtgcttagttgtcatgcagct   240
                     -----+----+----+----+----+----+----+----+----+----+----+
                      A  G  F  L  Y  T  G  E  G  D  T  V  R  C  F  S  C  H  A  A 241 gtagatagatggcaatatggagactcagcagttggaagacacaggaaagtatcccaaat   300
                     -----+----+----+----+----+----+----+----+----+----+----+
                      V  D  R  W  Q  Y  G  D  S  A  V  G  R  H  R  K  V  S  P  N 301 tgcagatttatcaacggctttatcttgaaaatagtgccacgcagtctacaaattctggt   360
                     -----+----+----+----+----+----+----+----+----+----+----+
                      C  R  F  I  N  G  F  Y  L  E  N  S  A  T  Q  S  T  N  S  G
```

Fig. 1A

HUMAN xiap

```
361 atccagaatggtcagtacaaagttgaaactatctgggaagcagagatcattttgcctta 420
     I  Q  N  G  Q  Y  K  V  E  N  Y  L  G  S  R  D  H  F  A  L 421 gacaggccatctgagacactgcagactatctttgagaactgggcaggttgtagatata 480
     D  R  P  S  E  T  H  A  D  Y  L  L  R  T  G  Q  V  V  D  I 481 tcagacaccacatatacccgagaaccctgccatgtattgtgaagaagctagattaaagtcc 540
     S  D  T  I  Y  P  R  N  P  A  M  Y  C  E  E  A  R  L  K  S 541 tttcagaactggccagactatgctcacctaaccccaagagagttagcaagtgctggactc 600
     F  Q  N  W  P  D  Y  A  H  L  T  P  R  E  L  A  S  A  G  L 601 tactacacaggtattggtgaccaagtgcagtgctttttgtgttgtggtgaaaactgaaaat 660
     Y  Y  T  G  I  G  D  Q  V  Q  C  F  C  C  G  G  K  L  K  N 661 tgggaacctttgatcgtgcctggtcagaacacaggcgacactttcctaattgcttcttt 720
     W  E  P  C  D  R  A  W  S  E  H  R  R  H  F  P  N  C  F  F
```

Fig. 1B

HUMAN xiap

```
721   gtctttgggccggaatcttaatattcgaagtgaatcgatgctgtgagttctgataggaat    780
      --------+---------+---------+---------+---------+---------+
  a    V  L  G  R  N  L  N  I  R  S  E  S  D  A  V  S  S  D  R  N 781   ttcccaaattcaacaaatcttccaagaatccatgcgcagattatgaagcacggatc      840
      --------+---------+---------+---------+---------+---------+
  a    F  P  N  S  T  N  L  P  R  N  P  S  M  A  D  Y  E  A  R  I 841   tttactttggacatggataatactcagttaacaaggagcagcttgcaagagctggattt   900
      --------+---------+---------+---------+---------+---------+
  a    F  T  F  G  T  W  I  Y  S  V  N  K  E  Q  L  A  R  A  G  F 901   tatgctttaggtgaaggtgataaagtgctttcactgtggaggaggctaactgat        960
      --------+---------+---------+---------+---------+---------+
  a    Y  A  L  G  E  G  D  K  V  K  C  F  H  C  G  G  G  L  T  D 961   tggaagccagtgaagacccttgggaacacatgctaaatgtatccaggtgcaaatat      1020
      --------+---------+---------+---------+---------+---------+
  a    W  K  P  S  E  D  P  W  E  Q  H  A  K  W  Y  P  G  C  K  Y 1021  ctgttagaacagaaagggacaagaataataaacatattcattaacttcattcacttgag   1080
      --------+---------+---------+---------+---------+---------+
  a    L  L  E  Q  K  G  Q  E  Y  I  N  N  I  H  L  T  H  S  L  E
```

Fig. 1C

HUMAN xiap

```
1081  gagtgtctggtaagaactactgagaaacaccatcactagagaattgatgatacc  1140
      ---------+---------+---------+---------+---------+---------+
      E  C  L  V  R  T  T  E  K  T  P  S  L  T  R  R  I  D  D  T 1141  atcttccaaaatcctatggtacaagaagctatacgaatggggttcagtttcaaggacatt  1200
      ---------+---------+---------+---------+---------+---------+
      I  F  Q  N  P  M  V  Q  E  A  I  R  M  G  F  S  F  K  D  I 1201  aagaaaataatggaggaaaaattcagatatctgggagcaactataaatcacttgaggtt  1260
      ---------+---------+---------+---------+---------+---------+
      K  K  I  M  E  E  K  I  Q  I  S  G  S  N  Y  K  S  L  E  V 1261  ctggttgcagatctagtgaatgctcagaaagacagtatgcaagatgagtcagtcagact  1320
      ---------+---------+---------+---------+---------+---------+
      L  V  A  D  L  V  N  A  Q  K  D  S  M  Q  D  E  S  S  Q  T 1321  tcattacagagaagattagtactgaagagcagctaaggcgcctgcaagaggagaagctt  1380
      ---------+---------+---------+---------+---------+---------+
      S  L  Q  K  E  I  S  T  E  E  Q  L  R  R  L  Q  E  E  K  L 1381  tgcaaaatctgtatggatagaaatattgctatcgttttgttccttgtggacatctagtc  1440
      ---------+---------+---------+---------+---------+---------+
```

Fig. 1D

HUMAN xiap

```
          C  K  I  C  M  D  R  N  I  A  I  V  F  V  P  C  G  H  L  V   -
1441  acttgtaaacaatgtgctgaagcagtgacaagtgtcccatgtgctacacagtcattact      1500
                                                                    -
       T  C  K  Q  C  A  E  A  V  D  K  C  P  M  C  Y  T  V  I  T   -
1501  ttcaagcaaaaatttatgtcttaatctatagtaggcatgttatgttgttct             1560
                                                                    -
       F  K  Q  K  I  F  M  S  *
1561  tattaccctgattgaatgtgatgtgaactgacttaagtaatcaggattgaattccat       1620
                                                                    -
1621  tagcattgctaccaagtaggaaaaaaatgtacatggcagtgtttagttggcaatata       1680
                                                                    -
1681  atctttgaatttctgattttcagggtattagctgtattatccatttttttactgtta      1740
                                                                    -
1741  tttaattgaaccatagactaagaataagaagcatcatactataactgaacacaatgtgt    1800
                                                                    -
```

Fig. 1E

HUMAN xiap

```
1801  attcatagtatactgattaatttctaagtgtaagtgaattaatcatctgatttttat  1860
      ----+----+----+----+----+----+----+----+----+----+----+----+
1861  tcttttcagataggcttaacaaatggagctttctgtatataaatgtggagattagagtta  1920
      ----+----+----+----+----+----+----+----+----+----+----+----+
1921  atctccccaatcacataatttgttttgtgtgaaaaggaataaattgttccatgctggtg  1980
      ----+----+----+----+----+----+----+----+----+----+----+----+
1981  gaaagatagagattgttttagaggttggttgtgttttaggattctgtccattttct  2040
      ----+----+----+----+----+----+----+----+----+----+----+----+
2041  tgtaaagnnataaacacgnacntgtgcgaaatatnttgtaaagtgatttgccattnttg  2100
      ----+----+----+----+----+----+----+----+----+----+----+----+
2101  aaagcgtatttaatgatagaatactatcgagccaacatgtactgacatggaaagatgtca  2160
      ----+----+----+----+----+----+----+----+----+----+----+----+
         a         a         a         a         a         a
```

Fig. 1F

HUMAN xiap

```
2161  nagatatgttaagtgtaaaatgcaagtggcnnnacactatgtatagtctgagccagatca  2220
      ---------+---------+---------+---------+---------+---------+   -
2221  aagtatgtatgttnttaatatgcatagaacnanagattggaaagatatacaccaaactg   2280
      ---------+---------+---------+---------+---------+---------+   -
2281  ttaaatgtggtttctcttcggggaggggggattggggagggggcccagagggggttta    2340
      ---------+---------+---------+---------+---------+---------+   -
2341  naggggccttttcacttttcnactttttcattttgttctgttcgnattttttataagtat  2400
      ---------+---------+---------+---------+---------+---------+   -
2401  gtanacccnaagggtttatgnaactaacatcagtaacctaaccccgtgactatcct      2460
      ---------+---------+---------+---------+---------+---------+   -
2461  gtnctcttcctaggagctgtnttgtttcccaccaccaccccttccctctgaacaaatgc   2520
      ---------+---------+---------+---------+---------+---------+   -
2521  ctgagtgctggggcactttn  2540
      ---------+----------
```

Fig. 1G

HUMAN hiap-1

```
SEQ ID NO:5
        1   TCCTTGAGATGTATCAGTAGTATAGGATTTAGGATCTCCATGTTGGAACTCTAAATGCATAGA    60
            ---------+---------+---------+---------+---------+---------+
       61   AATGGAAATAATGGAAATTTTTCATTTTGGCTTTTCAGCCCTAGTATTAAAACTGATAAAA   120
            ---------+---------+---------+---------+---------+---------+
      121   GCAAAGCCATGCACAAAACTACCTCCCTAGAGAAAGGCTAGTCCCTTTTCTTCCCCATTC   180
            ---------+---------+---------+---------+---------+---------+
      181   ATTTCATTATGAACATAGTAGAAAAACAGCATATTCTTATCAAATTTGATGAAAAGCGCCA   240
            ---------+---------+---------+---------+---------+---------+
SEQ ID NO:6
      241   ACACGTTTGAACTGAAATACGACTTGTCATGTGAACTGTACCGAATGTCTACGTATTCCA   300
            ---------+---------+---------+---------+---------+---------+
                M   N   I   V   E   N   S   I   F   L   S   N   L   M   K   S   A   N

301   CTTTTCCTGCTGGGGTTCCCTGTCTCAGAAAAGGAGTCTTGCTGCTGGTTTCTATTACA   360
            ---------+---------+---------+---------+---------+---------+
                T   F   E   L   K   Y   D   L   S   C   E   L   Y   R   M   S   T   Y   S   T

HUMAN hiap-1

```
361 CTGGTGTGAATGACAAGGTCAAATGCTTCTGTTGTGGCCTGATGCTGGATAACTGGAAAA 420
     G  V  N  D  K  V  K  C  F  C  C  G  L  M  L  D  N  W  K  R  -

421 GAGGAGACAGTCCTACTGAAAAGCATAAAAAGTTGTATCCTAGCTGCAGATTCGTTCAGA 480
     G  D  S  P  T  E  K  H  K  K  L  Y  P  S  C  R  F  V  Q  S  -

481 GTCTAAATTCCGTTAACAACTTGGAAGCTACCTCTCAGCCTACTTTCCTTCTTTCAGTAA 540
     L  N  S  V  N  N  L  E  A  T  S  Q  P  T  F  P  S  S  V  T  -

541 CACATTCCACACACTCATTACTTCCGGGTACAGAAAACAGTGGATATTCCGTGGCTCTT 600
     H  S  T  H  S  L  L  P  G  T  E  N  S  G  Y  F  R  G  S  Y  -

601 ATTCAAAACTCTCCATCAAATCCTGTAAACTCCAGAGCAAATCAAGAATTTCTGCCTTGA 660
     S  N  S  P  S  N  P  V  N  S  R  A  N  Q  E  F  S  A  L  M  -

661 TGAGAAGTTCCTACCCCTGTCCAATGAATAACGAAAATGCCAGATTACTTTTCAGA 720
     R  S  S  Y  P  C  P  M  N  N  E  N  A  R  L  L  T  F  Q  T  -
```

Fig. 2B

HUMAN hiap-1

```
      CATGGCCATTGACTTTTCTGTGCCAACAGATCTGGCACGAGCAGGCTTTTACTACATAG
721   ---------+---------+---------+---------+---------+---------+ 780
       W  P  L  T  F  L  S  P  T  D  L  A  R  A  G  F  Y  Y  I  G  -
   c

GACCTGGAGACAGAGTGGCTTGCTTTGCCTGTGGTGGAAAATTGAGCAATTGGGAACCGA
781   ---------+---------+---------+---------+---------+---------+ 840
       P  G  D  R  V  A  C  F  A  C  G  G  K  L  S  N  W  E  P  K  -
   c

AGGATAAATGCTATGTCAGAACACCTGAGACATTTCCCAAATGCCCATTTATAGAAAATC
841   ---------+---------+---------+---------+---------+---------+ 900
       D  N  A  M  S  E  H  L  R  H  F  P  K  C  P  F  I  E  N  Q  -
   c

AGCTTCAAGACACTTCAAGATACACAGTTTCTAATCTGAGCATGCAGACACATGCAGCCC
901   ---------+---------+---------+---------+---------+---------+ 960
       L  Q  D  T  S  R  Y  T  V  S  N  L  S  M  Q  T  H  A  A  R  -
   c

GCTTTAAAACATTCTTTAACTGGCCCTCTAGTGTTCTAGTTAATCCTGAGCAGCTTGCAA
961   ---------+---------+---------+---------+---------+---------+ 1020
       F  K  T  F  F  N  W  P  S  S  V  L  V  N  P  E  Q  L  A  S  -
   c

GTGCGGGTTTTTATTATGTGGGTAACAGTGATGATGTCAAATGCTTTTGCTGTGATGGTG
1021  ---------+---------+---------+---------+---------+---------+ 1080
       A  G  F  Y  Y  V  G  N  S  D  D  V  K  C  F  C  C  D  G  G  -
   c
```

Fig. 2C

HUMAN hiap-1

```
1081  GACTCAGGTGTTGGGAATCTGGAGATGATCCATGGGTTCAACATGCCAAGTGGTTTCCAA  1140
       L  R  C  W  E  S  G  D  D  P  W  V  Q  H  A  K  W  F  P  R  -

1141  GGTGTGAGTACTTGATAAGAATTAAAGGACACAGGAGTTCATCCGTCAAGTTCAAGCCAGTT  1200
       C  E  Y  L  I  R  I  K  G  Q  E  F  I  R  Q  V  Q  A  S  Y  -

1201  ACCCTCATCTACTTGAACAGCTGCTATCCACATCAGACAGCCCAGGAGATGAAAATGCAG  1260
       P  H  L  E  Q  L  L  S  T  S  D  S  P  G  D  E  N  A  E  -

1261  AGTCATCAATTATCCATTTGGAACCTGGAGAAGACCATTCAGAAGATGCAATCATGATGA  1320
       S  S  I  I  H  L  E  P  G  E  D  H  S  E  D  A  I  M  M  N  -

1321  ATACTCCTGTGATTAATGCTGCCGTGGAAATGGGCTTTAGTAGAAGCCTGGTAAAACAGA  1380
       T  P  V  I  N  A  A  V  E  M  G  F  S  R  S  L  V  K  Q  T  -

1381  CAGTTCAGAGAAAAATCCTAGCAACTGGAGAGAATTATAGACTAGTCAATGATCTTGTGT  1440
       V  Q  R  K  I  L  A  T  G  E  N  Y  R  L  V  N  D  L  V  L  -
```

Fig. 2D

HUMAN hiap-1

```
1441 TAGACTTACTCAATGCAGAAGATGAAATAAGGGAAGAGAGAGAAAGAGCAACTGAGG 1500
        D  L  N  A  E  D  E  I  R  E  E  E  R  E  R  A  T  E  E  -
1501 AAAAAGAATCAAATGATTTATTATTAATCCGGAAGAATAGAATGGCACTTTTTCAACATT 1560
        K  E  S  N  D  L  L  L  I  R  K  N  R  M  A  L  F  Q  H  L  -
1561 TGACTTGTGTAATTCCAATCCTGGATAGTCTACTAACTGCCGGAATTATTAATGAACAAG 1620
        T  C  V  I  P  I  L  D  S  L  L  T  A  G  I  I  N  E  Q  E  -
1621 AACATGATGTTATTAAACAGAAGACACAGAGTCTTTACAAGCAAGAGAACTGATTGATA 1680
        H  D  V  I  K  Q  K  T  Q  T  S  L  Q  A  R  E  L  I  D  T  -
1681 CGATTTTAGTAAAAGGAAATATTGCAGCCACTGTATTCAGAAACTCTCTGCAAGAAGCTG 1740
        I  L  V  K  G  N  I  A  A  T  V  F  R  N  S  L  Q  E  A  E  -
1741 AAGCTGTGTTATATGAGCATTTATTTGTGCAACAGCACATAAAATATATTCCCACAGAAG 1800
        A  V  L  Y  E  H  L  F  V  Q  Q  D  I  K  Y  I  P  T  E  D  -
```

Fig. 2E

HUMAN hiap-1

```
1801 ATGTTTCAGATCTACCAGTGGAAGAACAATTGCGGAGACTACCAGAAGAAGAACATGTA 1860
      V  S  D  L  P  V  E  E  Q  L  R  R  L  P  E  E  R  T  C  K
1861 AAGTGTGTATGGACAAAGAAGTGTCCATAGTGTTTATTCCTTGTGGTCATCTAGTAGTAT 1920
      V  C  M  D  K  E  V  S  I  V  F  I  P  C  G  H  L  V  V  C
1921 GCAAAGATTGTGCTCCTCCTTTAAGAAAGTGTCCTATTTGTAGGAGTACAATCAAGGGTA 1980
      K  D  C  A  P  S  L  R  K  C  P  I  C  R  S  T  I  K  G  T
1981 CAGTTCGTACACATTTCTTCTTTCATGAAGAACATGTCTAAACTTTAGAATTAAT 2040
      V  R  T  F  L  S  *
2041 TTATTAAATGTATTATAACTTTAACTTTTATCCTAATTGGTTTCCTTAAAATTTTATT 2100
2101 TATTTACAACTCAAAAAACATTGTTTTGTGTAACATATTTATATATGTATCTAAACCATA 2160
```

Fig. 2F

HUMAN hiap-1

```
2161  TGAACATATATTTTTAGAAACTAAGAGAATGATAGGCTTTTGTTCTTATGAACGAAAAA
      ---------+---------+---------+---------+---------+---------+  2220
                                                                    -

2221  GAGGTAGCACTACAAACACAATATTCAATCCAAATTTCAGCATTATTGAAATTGTAAGTG
      ---------+---------+---------+---------+---------+---------+  2280
                                                                    -

2281  AAGTAAAAACTTAAGATATTTGAGTTAACCTTTAAGAATTTTAAATATTTTGGCATTGTAC
      ---------+---------+---------+---------+---------+---------+  2340
                                                                    -

2341  TAATACCGGGAACATGAAGCCAGGTGTGGTGGTATGTACCTGTAGTCCCAGGCTGAGGCA
      ---------+---------+---------+---------+---------+---------+  2400
                                                                    -

2401  AGAGAATTACTTGAGCCCAGGAGTTTGAATCCATCCTGGGCAGCATACTGAGACCCTGCC
      ---------+---------+---------+---------+---------+---------+  2460
                                                                    -

2461  TTTAAAAACXAACAGXACCAAAXCCAAACACCAGGGACACATTTCTCTGTCTTTTTGAT
      ---------+---------+---------+---------+---------+---------+  2520
                                                                    -
``` c c c c c c

Fig. 2G

HUMAN hiap-1

```
2521 CAGTGTCCTATACATCGAAGGTGTGCATATATGTTGAATCACATTTTAGGGACATGGTGT
      ------------+---------+---------+---------+---------+---------+ 2580
                                                                    c

2581 TTTTATAAAGAATTCTGTGAGXAAAAATTTAATAAAGCAACCXAAATTACTCTTAAAAAA
      ------------+---------+---------+---------+---------+---------+ 2640
                                                                    c

2641 AAAAAAAAAAAAAAAACTCGAGGGGCCCGTACCAAT
      ------------+---------+---------+------ 2676
                                             c
```

Fig. 2H

HUMAN hiap-2

```
SEQ ID NO:7
           1  TTAGGTTACCTGAAAGAGTTACTACAACCCCAAAGAGTTGTGTTCTAAGTAGTATCTTGG   60
              ------+---------+---------+---------+---------+---------+
        a
          61  TAATTCAGAGAGATACTCATCCTACCTGAATATAAACTGAGATAAATCCAGTAAAGAAAG  120
              ------+---------+---------+---------+---------+---------+
        a
         121  TGTAGTAAATTCTACATAAGAGTCTATCATTGATTTCTTTTTGTGGTGGAAATCTTAGTT  180
              ------+---------+---------+---------+---------+---------+
        a
         181  CATGTGAAGAAATTTCATGTGAATGTTTTAGCTATCAAACAGTACTGTCACCTACTCATG  240
              ------+---------+---------+---------+---------+---------+
                                                                       M
         241  CACAAAAACTGCCTCCCAAAGACTTTTCCCAGGTCCCCTCGTATCAAACATTAAGAGTATA  300
              ------+---------+---------+---------+---------+---------+
        a      H  K  T  A  S  Q  R  L  F  P  G  P  S  Y  Q  N  I  K  S  I

SEQ ID NO:8
         301  ATGGAAGATAGCACGATCTTGTCAGATTGGACAAACAGCAACAAACAAAAAATGAAGTAT  360
              ------+---------+---------+---------+---------+---------+
        a      M  E  D  S  T  I  L  S  D  W  T  N  S  N  K  Q  K  M  K  Y
```

Fig. 3A

HUMAN hiop-2

```
     GACTTTTCCTGTGAACTCTACAGAATGTCTACATATTCAACTTTCCCGCCGGGGTGCCT
361  ------+---------+---------+---------+---------+---------+  420
      D  F  S  C  E  L  Y  R  M  S  T  Y  S  T  F  P  A  G  V  P

GTCTCAGAAAGGAGTCTTGCTCGTGGTTTTATTATACTGGTGTGAATGACAAGGTC
421  ------+---------+---------+---------+---------+---------+  480
      V  S  E  R  S  L  A  R  A  G  F  Y  Y  T  G  V  N  D  K  V

AAATGCTTCTGTTGTGGCCTGATGCTGGATAACTGGAAACTAGGAGACAGTCCTATTCAA
481  ------+---------+---------+---------+---------+---------+  540
      K  C  F  C  C  G  L  M  L  D  N  W  K  L  G  D  S  P  I  Q

AAGCATAAACAGCTATATCCTAGCTGTAGCTTTATTCAGAATCTGGTTTCAGCTAGTCTG
541  ------+---------+---------+---------+---------+---------+  600
      K  H  K  Q  L  Y  P  S  C  S  F  I  Q  N  L  V  S  A  S  L

GGATCCACCTCTAAGAATACGTCTCCAATGAGAAACAGTTTTGCACATTCATTATCTCCC
601  ------+---------+---------+---------+---------+---------+  660
      G  S  T  S  K  N  T  S  P  M  R  N  S  F  A  H  S  L  S  P

ACCTTGGAACATAGTAGCTTGTTCAGTGGTTCTTACTCCAGCCTTCCTCCAAACCCCTCTT
661  ------+---------+---------+---------+---------+---------+  720
      T  L  E  H  S  S  L  F  S  G  S  Y  S  S  L  P  P  N  P  L
```

Fig. 3B

HUMAN hiap-2

```
       AATTCTAGAGCAGTTGAAGACATCTCTTCATCGAGGACTAACCCCTACAGTTATGCAATG
 721   ------------------------------------------------------------  780
        N  S  R  A  V  E  D  I  S  S  S  R  T  N  P  Y  S  Y  A  M

AGTACTGAAGAAGCCAGATTTCTTACCTACCATATGTGGCCATTAACTTTTTTGTCACCA
 781   ------------------------------------------------------------  840
        S  T  E  E  A  R  F  L  T  Y  H  M  W  P  L  T  F  L  S  P

TCAGAATTGGCAAGAGCTGGTTTTTATTATATAGGACCTGGAGATAGGGTAGCCTGCTTT
 841   ------------------------------------------------------------  900
        S  E  L  A  R  A  G  F  Y  Y  I  G  P  G  D  R  V  A  C  F

GCCTGTGGTGGGAAGCTCAGTAACTGGGAACCAAAGGATGATGCTATGTCAGAACACCGG
 901   ------------------------------------------------------------  960
        A  C  G  G  K  L  S  N  W  E  P  K  D  D  A  M  S  E  H  R

AGGCATTTCCCAACTGTCCATTTTTGGAAAATTCTCTAGAAACTCTGAGGTTTAGCATT
 961   ------------------------------------------------------------ 1020
        R  H  F  P  N  C  P  F  F  L  E  N  S  L  E  T  L  R  F  S  I

TCAAATCTGAGCATGCAGACACATGCAGCTCGAATGAGAACATTTATGTACTGGCCATCT
1021   ------------------------------------------------------------ 1080
        S  N  L  S  M  Q  T  H  A  A  R  M  R  T  F  M  Y  W  P  S
```

Fig. 3C

HUMAN hiap-2

```
1081  AGTGTTCCAGTTCAGCCTGAGCAGCTTGCAAGTGCTGTGGTTTTATTATGTGGGTCGCAAT  1140
       S  V  P  V  Q  P  E  Q  L  A  S  A  G  F  Y  Y  V  G  R  N

1141  GATGATGTCAAATGCTTTGGTTGTGATGGTGGCTTGAGGTGTTGGGAATCTGGAGATGAT  1200
       D  D  V  K  C  F  G  C  D  G  G  L  R  C  W  E  S  G  D  D

1201  CCATGGGTAGAACATGCCAAGTGGTTTCCAAGGTGTGAGTTCTTGATACGAATGAAAGGC  1260
       P  W  V  E  H  A  K  W  F  P  R  C  E  F  L  I  R  M  K  G

1261  CAAGAGTTTGTTGATGAGATTCAAGGTAGATATCCTCATCTTCTTGAACAGCTGTTGTCA  1320
       Q  E  F  V  D  E  I  Q  G  R  Y  P  H  L  L  E  Q  L  L  S

1321  ACTTCAGATACCACTGGAGAAGAAAATGCTGACCCACCAATTATTCATTTTGGACCTGGA  1380
       T  S  D  T  T  G  E  E  N  A  D  P  P  I  I  H  F  G  P  G

1381  GAAAGTTCTTCAGAAGATGCTGTCATGATGAATACACCTGTGGTTAAATCTGCCTTGGAA  1440
       E  S  S  E  D  A  V  M  M  N  T  P  V  V  K  S  A  L  E
```

Fig. 3D

HUMAN hiap-2

```
1441  ATGGGCTTTAATAGAGACCTGGTGAAACAAACAGTTCTAAGTAAAATCCTGACAACTGGA
       ---------+---------+---------+---------+---------+---------+ 1500
   a    M  G  F  N  R  D  L  V  K  Q  T  V  L  S  K  I  L  T  T  G

1501  GAGAACTATAAAACAGTTAATGATATTGTGTCAGCACTTCTTAATGCTGAAGATGAAAAA
       ---------+---------+---------+---------+---------+---------+ 1560
   a    E  N  Y  K  T  V  N  D  I  V  S  A  L  L  N  A  E  D  E  K

1561  AGAGAAGAGGAAGAAAAACAAGCTGAAGAAATGGCATCAGATGATTTGTCATTAATT
       ---------+---------+---------+---------+---------+---------+ 1620
   a    R  E  E  E  K  Q  A  E  E  M  A  S  D  D  L  S  L  I

1621  CGGAAGAACAGAATGGCTCTCTTTCAACAATTGACATGTGTCTTCCTATCCTGATAAT
       ---------+---------+---------+---------+---------+---------+ 1680
   a    R  K  N  R  M  A  L  F  Q  Q  L  T  C  V  L  P  I  L  D  N

1681  CTTTTAAAGGCCAATGTAATTAATAAACAGGAACATGATATTATTAAACAAAAACACAG
       ---------+---------+---------+---------+---------+---------+ 1740
   a    L  L  K  A  N  V  I  N  K  Q  E  H  D  I  K  Q  K  T  Q

1741  ATACCCTTTACAAGCCGAGAGAACTGATTGATACCATTTGGGTTAAAGGAAATGCTGCGGCC
       ---------+---------+---------+---------+---------+---------+ 1800
   a    I  P  L  Q  A  R  E  L  I  D  T  I  W  V  K  G  N  A  A  A
```

Fig. 3E

HUMAN hiap-2

```
1801 AACATCTTCAAAAACTGTCTAAAGAATTGACTTCTACATTGTATAAGAACTTATTTGTG
     ------+---------+---------+---------+---------+---------+ 1860
      N  I  F  K  N  C  L  K  E  I  D  S  T  L  Y  K  N  L  F  V

1861 GATAAGAATATGAAGTATATTCCAACAGAAGATGTTCAGGTCTGTCACTGGAAGAACAA
     ------+---------+---------+---------+---------+---------+ 1920
      D  K  N  M  K  Y  I  P  T  E  D  V  S  G  L  S  L  E  E  Q

1921 TTGAGGAGGTTGCAAGAAGAACGAACTTGTAAAGTGTGTATGGACAAAGAAGTTTCTGTT
     ------+---------+---------+---------+---------+---------+ 1980
      L  R  R  L  Q  E  E  R  T  C  K  V  C  M  D  K  E  V  S  V

1981 GTATTTATTCCTTGTGGTCATCTGGTAGTATGCCAGGAATGTGCCCCTTCTCTAAGAAAA
     ------+---------+---------+---------+---------+---------+ 2040
      V  F  I  P  C  G  H  L  V  V  C  Q  E  C  A  P  S  L  R  K

2041 TGCCCTATTTGCAGGGGTATAATCAAGGGTACTGTTCGTACATTTCTCTCTTAAAGAAAA
     ------+---------+---------+---------+---------+---------+ 2100
      C  P  I  C  R  G  I  I  K  G  T  V  R  T  F  L  S  *

2101 ATAGTCTATATTTTAACCTGCATAAAAAGTCTTTAAAATATTGTTGAACACTTGAAGCC
     ------+---------+---------+---------+---------+---------+ 2160
```

Fig. 3F

HUMAN hiap-2

```
2161 ATCTAAAAGTAAAAAGGGAATTATGAGTTTTCAATTAGTAACATTCATGTTCTAGTCTGC 2220
     ----+----+----+----+----+----+----+----+----+----+----+----+
2221 TTTGGTACTAATAATCTTGTTTCTGAAAAGATGGTATCATATATTAATCTTAATCTGTT 2280
     ----+----+----+----+----+----+----+----+----+----+----+----+
2281 TATTTACAAGGGAAGATTTATGTTTGGTGAACTATATATTAGTATGTATGTGTACCTAAGGG 2340
     ----+----+----+----+----+----+----+----+----+----+----+----+
2341 AGTAGCGTCXCTGCTTGTTATGCATCATTCAGGAGTTACTGGATTTGTGTTGTTCTTTCAG 2400
     ----+----+----+----+----+----+----+----+----+----+----+----+
2401 AAAGCTTTGAAXACTAAATTATAGTGTAGAAAAGAACTGGAAACCAGGAACTCTGGAGTT 2460
     ----+----+----+----+----+----+----+----+----+----+----+----+
2461 CATCAGAGTTATGGTGCCGAATTGTCTTTGGTGCTTTTCACTTGTGTTTAAAATAAGGA 2520
     ----+----+----+----+----+----+----+----+----+----+----+----+
2521 TTTTTCTCTTATTCTCCCCCTAGTTTGTGAGAAACATCTCAATAAAGTGCTTTAAAAAG 2580
     ----+----+----+----+----+----+----+----+----+----+----+----+
```

Fig. 3G

MOUSE xiap

```
SEQ ID NO:9    1  GACACTCTGCTGGGGCGGGGGCCGCCCTCCCTCCGGGACCTCCCCTCGGGAACCGTGCGCC    60
                  ---------+---------+---------+---------+---------+---------+
              61  GCGGCGCTTAGTTAGGACTGGAGTGCTTGGCGCGGAAAAGGTGGACAAGTCCTATTTTCCA   120
                  ---------+---------+---------+---------+---------+---------+
             121  GAGAAGATGACTTTTAACAGTTTTGAAGGAACTAGAACTTTTGTACTTGCAGACACCAAT   180
                  ---------+---------+---------+---------+---------+---------+
SEQ ID NO:10 a         M  T  F  N  S  F  E  G  T  R  T  F  V  L  A  D  T  N

181  AAGGATGAAGAATTTGTAGAAGAGTTTAATAGATTAAAAACATTTGCTAACTTCCCAAGT   240
                  ---------+---------+---------+---------+---------+---------+
             a     K  D  E  E  F  V  E  E  F  N  R  L  K  T  F  A  N  F  P  S

241  AGTAGTCCTGTTTCAGCATCAACATTGGCCGCGAGCTGGGTTTCTTTATACCGGTGAAGGA  300
                  ---------+---------+---------+---------+---------+---------+
             a     S  S  P  V  S  A  S  T  L  A  R  A  G  F  L  Y  T  G  E  G

301  GACACCGTGCAATGTTTCAGTTGTCATGCGGCAATAGATAGATGGCAGTATGGAGACTCA  360
                  ---------+---------+---------+---------+---------+---------+
             a     D  T  V  Q  C  F  S  C  H  A  A  I  D  R  W  Q  Y  G  D  S
```

Fig. 4A

MOUSE xiap

```
361 GCTGTTGGAAGACACAGGAGAATATCCCAAATTGCAGATTTATCAATGTTTTATTTT 420
     A  V  G  R  H  R  R  I  S  P  N  C  R  F  I  N  G  F  Y  F

421 GAAAATGGTGCTGCACAGTCTACAAATCCTGGTATCCAAAATGGCCAGTACAAATCTGAA 480
     E  N  G  A  A  Q  S  T  N  P  G  I  Q  N  G  Q  Y  K  S  E

481 AACTGTGTGGGAAATAGAAATCCTTTTGCCCCTGACAGGCCACCTGAGACTCATGCTGAT 540
     N  C  V  G  N  R  N  P  F  A  P  D  R  P  P  E  T  H  A  D

541 TATCTCTTGAGAACTGGACAGGTTGTAGATATTTCAGACACCATATACCCGAGGAACCCT 600
     Y  L  L  R  T  G  Q  V  V  D  I  S  D  T  I  Y  P  R  N  P

601 GCCATGTGTAGTGAAGAAGCCAGATTGAAGTCATTTCAGAACTGGCCGGACTATGCTCAT 660
     A  M  C  S  E  E  A  R  L  K  S  F  Q  N  W  P  D  Y  A  H

661 TTAACCCCCAGAGAGTTAGCTAGTGCTGGCCCTCTACTACACAGGGGCTGATGATCAAGTG 720
     L  T  P  R  E  L  A  S  A  G  L  Y  Y  T  G  A  D  D  Q  V
```

Fig. 4B

MOUSE xiap

```
721  CAATGCTTTTGTTGTGGGGGAAAACTGAAAAATTGGGAACCCTGTGATCGTGCCTGGTCA  780
        Q  C  F  C  G  G  K  L  K  N  W  E  P  C  D  R  A  W  S

781  GAACACAGGAGACACTTTCCCAATTGCTTTTTTGTTTTGGGCCGGAACGTTAATGTTCGA  840
        E  H  R  R  H  F  P  N  C  F  F  V  L  G  R  N  V  N  V  R

841  AGTGAATCTGGTGTGAGTTCTGATAGGAATTTCCCAAATTCAACAAACTCTCCAAGAAAT  900
        S  E  S  G  V  S  S  D  R  N  F  P  N  S  T  N  S  P  R  N

901  CCAGCCATGGCAGAATATGAAGCACGGATCGTTACTTTTGGAACATGGATATACTCAGTT  960
        P  A  M  A  E  Y  E  A  R  I  V  T  F  G  T  W  I  Y  S  V

961  AACAAGGAGCAGCTTGCAAGAGCTGGATTTTATGCTTTAGGTGAAGGCGATAAAGTGAAG  1020
        N  K  E  Q  L  A  R  A  G  F  Y  A  L  G  E  G  D  K  V  K

1021 TGCTTCCACTGTGGAGGGGCTCACGGATTGGAAGCCAAGTGAAGACCCCTGGGACCAG    1080
        C  F  H  C  G  G  G  L  T  D  W  K  P  S  E  D  P  W  D  Q
```

Fig. 4C

MOUSE xiap

```
     CATGCTAAGTGCTACCCAGGGTGCAAATACCTATTGGATGAGAAGGGGCAAGAATATATA
1081 ------------------------------------------------------------ 1140
      H   A   K   C   Y   P   G   C   K   Y   L   L   D   E   K   G   Q   E   Y   I
     AATAATATTCATTTAACCCATCCACTTGAGGAATCTTTGGGAAGAACTGCTGAAAAAACA
1141 ------------------------------------------------------------ 1200
      N   N   I   H   L   T   H   P   L   E   E   S   L   G   R   T   A   E   K   T
     CCACCGCTAACTAAAAAAAATCGATGATACCATCTTCCAGAATCCTATGGTGTCAAGAAGCT
1201 ------------------------------------------------------------ 1260
      P   P   L   T   K   K   I   D   D   T   I   F   Q   N   P   M   V   Q   E   A
     ATACGAATGGGATTTAGCTTCAAGGACCTTAAGAAGACCAATGAAGAAAAATCCAAACA
1261 ------------------------------------------------------------ 1320
      I   R   M   G   F   S   F   K   D   L   K   K   T   M   E   E   K   I   Q   T
     TCCGGGAGCAGCTATCTATCACTTGAGGTCCGATTGCAGATCTTGTGAGTGCTCAGAAA
1321 ------------------------------------------------------------ 1380
      S   G   S   S   Y   L   S   L   E   V   L   I   A   D   L   V   S   A   Q   K
     GATAATACGGAGGATGAGTCAAGTCAAACTTCATTGCAGAAAGACATTAGTACTGAAGAG
1381 ------------------------------------------------------------ 1440
      D   N   T   E   D   E   S   S   Q   T   S   L   Q   K   D   I   S   T   E   E
```

Fig. 4D

MOUSE xiap

```
1441 CAGCTAAGGCGCCTACAAGAGGAGAAGCTTTCCAAATCTGTATGGATAGAAATATTGCT
     ------+---------+---------+---------+---------+---------+ 1500
      Q  L  R  R  L  Q  E  E  K  L  S  K  I  C  M  D  R  N  I  A    -

1501 ATCGTTTTTTTCCTTGTGGACATCTGGCCACTTGTAAACAGTGTCAGAAGCAGTTGAC
     ------+---------+---------+---------+---------+---------+ 1560
      I  V  F  F  P  C  G  H  L  A  T  C  K  Q  C  A  E  A  V  D    -

1561 AAATGTCCCATGTGCTACACCGTCATTACGTTCAACCAAAAATTTTATGTCTTAGTGG
     ------+---------+---------+---------+---------+---------+ 1620
      K  C  P  M  C  Y  T  V  I  T  F  N  Q  K  I  F  M  S  *       -

1621 GGCACCACATGTTATGTCTTCTTGCTCTAATTGAATGTGTAATGGGAGCGAACTTTAAG
     ------+---------+---------+---------+---------+---------+ 1680

1681 TAATCCCTGCATTTGCATTCCATTAGCATCCCTGCTGTTTCCAAATGGAGACCAATGCTAAC
     ------+---------+---------+---------+---------+---------+ 1740

1741 AGCACTGTTTCCGTCTAAACATTCAATTTCTGGATCTTTCGAGTTATCAGCTGTATCATT
     ------+---------+---------+---------+---------+---------+ 1800
```

Fig. 4E

MOUSE xiap

```
1801 TAGCCAGTGTTTACTCGATTGAAACCTTAGACAGAGAAGCATTTTATAGCTTTTCACAT 1860
1861 GTATATTGGTAGTACACTGACTTGATTTCTATATGTAAGTGAATTCATCACCTGCATGTT 1920
1921 TCATGCCTTTTGCATAAGCTTAACAAATGGAGTGTTCTGTATAAGCATGGAGATGTGATG 1980
1981 GAATCTGCCCAATGACTTTAATTGGCTTATTGTAAACACGGAAAGAACTGCCCCACGCTG 2040
2041 CTGGGAGGATAAAGATTGTTTTAGATGCTCACTTCTGTGTTTTAGGATTCTGCCCATTTA 2100
```

Fig. 4F

M-hiap-1

```
SEQ ID NO:39    GAATTCCGGGAGACCTACACCCCCGGAGATCAGAGGTCATTGCTGGCGTTCAGAGCCTAG
              1 ----+----+----+----+----+----+----+----+----+----+----+----+  60
                GAAGTGGGCTGCGGTATCAGCAGCCTAGCAGTAGAAACCGACTAAAACCACAAAAACTAC
             61 ----+----+----+----+----+----+----+----+----+----+----+----+ 120
                ATCCCCAGAGAAAGACTTGTCCCTTCCCCTCCCTGTCATCTCACCATGAACATGGTTCAA
            121 ----+----+----+----+----+----+----+----+----+----+----+----+ 180
                                                            M  N  M  V  Q

SEQ ID NO:40    GACAGCGCCTTTCTAGCCAAGCTGATGAAGAGTGCTGACACCTTTGAGTTGAAGTATGAC
            181 ----+----+----+----+----+----+----+----+----+----+----+----+ 240
                 D  S  A  F  L  A  K  L  M  K  S  A  D  T  F  E  L  K  Y  D
                TTTTCCTGTGAGCTGTACCGATTGTCCACGTATTCAGCTTTTCCCAGGGGAGTTCCTGTG
            241 ----+----+----+----+----+----+----+----+----+----+----+----+ 300
                 F  S  C  E  L  Y  R  L  S  T  Y  S  A  F  D  R  G  V  P  V
                TCAGAAAGGAGTCTGGCTCGTGCTGGCTTTTACTACACTGGTGCCAATGACAAGGTCAAG
            301 ----+----+----+----+----+----+----+----+----+----+----+----+ 360
                 S  E  R  S  L  A  R  A  G  F  Y  Y  T  G  A  N  D  K  V  K
                TGCTTCTGCTGTGGCCTGATGCTAGACAACTGGAAACAAGGGGACAGTCCCATGGAGAAG
            361 ----+----+----+----+----+----+----+----+----+----+----+----+ 420
                 C  F  C  C  G  L  M  L  D  N  W  K  Q  G  D  S  P  M  E  K
```

Fig. 5A

M-hiap-1

```
421 CACAGAAAGTTGTACCCCAGCTGCAACTTTGTACAGACTTTGAATCCAGCCAACAGTCTG
     ------+---------+---------+---------+---------+---------+ 480
      H  R  K  L  Y  P  S  C  N  F  V  Q  T  L  N  P  A  N  S  L

481  GAAGCTAGTCCTCGGCCTTCTCTTCCTTCCACGGCGATGAGCACCATGCCTTTGAGCTTT
     ------+---------+---------+---------+---------+---------+ 540
      E  A  S  P  R  P  S  L  P  S  T  A  M  S  T  M  P  L  S  F

541  GCAAGTTCTGAGAATACTGGCTATTTCAGTGGCTCTTACTCGAGCTTTCCCTCAGACCCT
     ------+---------+---------+---------+---------+---------+ 600
      A  S  S  E  N  T  G  Y  F  S  G  S  Y  S  S  F  P  S  D  P

601  GTGAACTTCCGAGCAAATCAAGATTGTCCTGCTTTGAGCACAAGTCCCTACCACTTTGCA
     ------+---------+---------+---------+---------+---------+ 660
      V  N  F  R  A  N  Q  D  C  P  A  L  S  T  S  P  Y  H  F  A

661  ATGAACACAGAGAAGGCCAGATTACTCACCTATGAAACATGGCCATTGTCTTTTCTGTCA
     ------+---------+---------+---------+---------+---------+ 720
      M  N  T  E  K  A  R  L  L  T  Y  E  T  W  P  L  S  F  L  S

721  CCAGCAAAGCTGGCCAAAGCAGGCTTCTACTACATAGGACCTGGAGATAGAGTGGCCTGC
     ------+---------+---------+---------+---------+---------+ 780
      P  A  K  L  A  K  A  G  F  Y  Y  I  G  P  G  D  R  V  A  C
```

Fig. 5B

M-hiap-1

```
781  TTTGCGTGCGATGGGAAACTGAGCAACTGGAACGTAAGGATGATGCTATGTCAGAGCAC  840
      F  A  C  D  G  K  L  S  N  W  E  R  K  D  D  A  M  S  E  H

841  CAGAGGCATTCCCCAGCTGTCCGTTCTTAAKGACTTGGGTCAGTCTGCTTCGAGATAC  900
      Q  R  H  F  P  S  C  P  F  F  L  K  D  L  G  Q  S  A  S  R  Y

901  ACTGTCTCTAACCTGAGCATGCAGACACGCAGCCCGTATTAGAACATTCTCTAACTGG  960
      T  V  S  N  L  S  M  Q  T  H  A  A  R  I  R  T  F  S  N  W

961  CCTTCTAGTGCACTAGTTCATTCCCAGGAACTTGCAAGTGCGGGCTTTATTATACAGGA 1020
      P  S  S  A  L  V  H  S  Q  E  L  A  S  A  G  F  Y  Y  T  G

1021 CACAGTGATGATGTCAAGTGTTTATGCTGTGATGTGGGCTGAGGTGCTGGGAATCTGGA 1080
      H  S  D  D  V  K  C  L  C  C  D  G  G  L  R  C  W  E  S  G

1081 GATGACCCCCTGGGTGGAACATGCCAAGTGGTTTCCAAGGTGTGAGTACTTGCTCAGAATC 1140
      D  D  P  W  V  E  H  A  K  W  F  P  R  C  E  Y  L  L  R  I

1141 AAAGGCCAAGAATTTGTCAGCCAAGTTCAAGCTGGCTATCCTCATCTACTTGAGCAGCTA 1200
      K  G  Q  E  F  V  S  Q  V  Q  A  G  Y  P  H  L  L  E  Q  L
```

Fig. 5C

M-hiap-1

```
     TTATCTACGTCAGACTCCCCAGAAGATGAGAATGCAGAGCGCAGCAATCGTGCATTTTGGC
1201 ------------+---------+---------+---------+---------+---------+ 1260
      L  S  T  S  D  S  P  P  E  D  E  N  A  D  A  A  I  V  H  F  G

CCTGGAGAAAGTTCGGAAGATGTCGTCATGATGAGCACGCCTGTGGTTAAAGCAGCCTTG
1261 ------------+---------+---------+---------+---------+---------+ 1320
      P  G  E  S  S  E  D  V  V  M  M  S  T  P  V  V  K  A  A  L

GAAATGGGCTTCAGTAGGAGCCTGGTGAGACAGACGGTTCAGTGGCAGATCCTGGCCACT
1321 ------------+---------+---------+---------+---------+---------+ 1380
      E  M  G  E  S  R  S  L  V  R  Q  T  V  Q  W  Q  I  L  A  T

GGTGAGAACTACAGGACCGTCAGTGACCTCGTTATAGGCTTACTCGATGCAGAAGACGAG
1381 ------------+---------+---------+---------+---------+---------+ 1440
      G  E  N  Y  R  T  V  S  D  L  V  I  G  L  L  D  A  E  D  E

ATGAGAGAGGAGCAGATGGAGCAGGCGGCCGAGGAGGAGTCAGATGATCTAGCACTA
1441 ------------+---------+---------+---------+---------+---------+ 1500
      M  R  E  E  Q  M  E  Q  A  A  E  E  E  E  S  D  D  L  A  L

ATCCGGAAGAACAAAATGGTGCTTTTCCAACATTTGACGTGTGTGACACCAATGCTGTAT
1501 ------------+---------+---------+---------+---------+---------+ 1560
      I  R  K  N  K  M  V  L  F  Q  H  L  T  C  V  T  P  M  L  Y
```

Fig. 5D

M-hiap-1

```
1561  TGCCTCCTAAGTGCAAGGGCCATCACTGAACAGGAGTGCAATGCTGTGAAACAGAAACCA  1620
       C  L  L  S  A  R  A  I  T  E  Q  E  C  N  A  V  K  Q  K  P

1621  CACACCTTACAAGCAAGCACACTGATTGATACTGTGTTAGCAAAAGGAAACACTGCAGCA  1680
       H  T  L  Q  A  S  T  L  I  D  T  V  L  A  K  G  N  T  A  A

1681  ACCTCATTCAGAAATTCCCTTCGGGAAATTGACCCTGCGTTATACAGAGATATATTTGTG  1740
       T  S  F  R  N  S  L  R  E  I  D  P  A  L  Y  R  D  I  F  V

1741  CAACAGGACATTAGGAGTCTTCCCACAGATGACATTGCAGCTCTACCAATGGAAGAACAG  1800
       Q  Q  D  I  R  S  L  P  T  D  D  I  A  A  L  P  M  E  E  Q

1801  TTGCGGCCCCTCCCGGAGGACAGAATGTGTAAAGTGTGTATGGACCGAGAGGTATCCATC  1860
       L  R  P  L  P  E  D  R  M  C  K  V  C  M  D  R  E  V  S  I

1861  GTGTTCATTCCCTGTGGCCATCTGGTCGTGTGCAAAGACTGCGCTCCCTCTCTGAGGAAG  1920
       V  F  I  P  C  G  H  L  V  V  C  K  D  C  A  P  S  L  R  K
```

Fig. 5E

M-hiap-1

```
1921 TGTCCCATCTGTAGAGGGACCATCAAGGGCACAGTGCGCACATTCTCTCCTGAACAAGA
      ------+---------+---------+---------+---------+---------+ 1980
       C  P  I  C  R  G  T  I  K  G  T  V  R  T  F  L  S  *

1981 CTAATGGTCCATGGCTGCAACTTCAGCCAGGAGGAAGTTCACTGTCACTCCCAGTTCCAT
      ------+---------+---------+---------+---------+---------+ 2040

2041 TCGGAACTTGAGGCCAGCCTGGATAGCACGAGACACCGCCAAACkCACAAATATAAACAT
      ------+---------+---------+---------+---------+---------+ 2100

2101 GAAAAACTTTTGTCTGAAGTCAAGAATGAATTACTTATATAATAATTTTAATTGGT
      ------+---------+---------+---------+---------+---------+ 2160

2161 TTCCTTAAAAGTGCTATTTGTTCCCAACTCAGAAAAATTGTTTTCTGTAAACATATTTACA
      ------+---------+---------+---------+---------+---------+ 2220

2221 TACTACCTGCATCTAAAGTATTCATATATTCAGATGTCATGAGAGAGGGTTT
      ------+---------+---------+---------+---------+---------+ 2280

2281 TGTTCTTGTTCCTGAAAAGCTGGTTTATCATCTGATCAGCATATACTGCGCAACGGGCAG
      ------+---------+---------+---------+---------+---------+ 2340

2341 GGCTAGAATCCATGAACCAAGCTGCAAAGATCTCACGCTAAATAAGGCGGAAAGATTTGG
      ------+---------+---------+---------+---------+---------+ 2400

2401 AGAAACGAAAGGAAATTCTTTCCTGTCCAATGTATACTCTTCAGACTAATGACCTCTTCC
      ------+---------+---------+---------+---------+---------+ 2460

2461 TATCAAGCCTTCTA
      ------+------ 2474
```

Fig. 5F

M-hiap-2

```
SEQ ID NO:41
        1   CTGTGGTGGAGATCTATTGTCCAAGTGGTGAGAAACTTCATCTGGAAGTTTAAGCGGTCA    60
       61   GAAATACTATTACTACTCATGGACAkRACTGTCTCCCAGAGACTCGCCCAAGGTACCTTA   120
      121   CACCCRAAAACTTAAACGTATAATGGAGAAGAGCACAATCTTGTCAAATTGGACAAAGGA   180
SEQ ID NO:42
                          M  E  K  S  T  I  L  S  N  W  T  K  E
      181   GAGCGAAGAAAAAAATGAAGTTTGACTTTTCGTGTGAACTCTACCGAATGTCTACATATTC   240
             S  E  E  K  M  K  F  D  F  S  C  E  L  Y  R  M  S  T  Y  S
      241   AGCTTTTCCCAGGGAGTTCCTGTCTCAGAGAGAGTCTGGCTCGTGCTCGTGCTGGCTTTTATTA   300
             A  F  P  R  G  V  P  V  S  E  R  S  L  A  R  A  G  F  Y  Y
      301   TACAGGTGTGAATGACAAAGTCAAGTGCTTCTGCTGTGGCCTGATGTTGGATAACTGGAA   360
             T  G  V  N  D  K  V  K  C  F  C  C  G  L  M  L  D  N  W  K
      361   ACAAGGGGACAGTCCTGTTGAAAAGCACAGACAGTTCTATCCCAGCTGCAGCTTTGTACA   420
             Q  G  D  S  P  V  E  K  H  R  Q  F  Y  P  S  C  S  F  V  Q
```

Fig. 6A

M-hiap-2

```
421 GACTCTGCTTTCAGCCAGTCTGCAGTCTCCATCTAAGAATATGTCTCCTGTGAAAAGTAG 480
     T   L   L   S   A   S   L   Q   S   P   S   K   N   M   S   P   V   K   S   R

481 ATTTGCACATTCGTCACCTCTGGAACGAGGTGGCATTCACTCCAACCTGTCTCTAGCCC 540
     F   A   H   S   S   P   L   E   R   G   G   I   H   S   N   L   C   S   S   P

541 TCTTAATTCTAGAGCAGTGGAAGACTTCTCATCAAGGATGATCCCTGCAGCTATGCCAT 600
     L   N   S   R   A   V   E   D   F   S   S   R   M   D   P   C   S   Y   A   M

601 GAGTACAGAAGAGGCCAGATTCTTACTTACAGTATGTGGCCTTTAAGTTTTCTGTCACC 660
     S   T   E   E   A   R   F   L   T   Y   S   M   W   P   L   S   F   L   S   P

661 AGCAGAGAGCTGGCCAGAGCTGGCTTCTATTACATAGGGCCTGGAGACAGAGGTGCCTGTTT 720
     A   E   L   A   R   A   G   F   Y   Y   I   G   P   G   D   R   V   A   C   F

721 TGCCTGTGTGGTGGGAAACTGAGCAACTGGGAACCAAAGGATTATGCTATGTCAGAGCACCG 780
     A   C   G   G   K   L   S   N   W   E   P   K   D   Y   A   M   S   E   H   R
```

Fig. 6B

M-hiap-2

```
781  CAGACATTTTCCCCACTGTCCATTTCTGGAAAATACTTCAGAAACACAGAGGTTTAGTAT  840
      R  H  F  P  H  C  P  F  L  E  N  T  S  E  T  Q  R  F  S  I

841  ATCAAATCTAAGTATGCAGACACACTCTGCTCGATTGAGGACATTTCTGTACTGGCCACC  900
      S  N  L  S  M  Q  T  H  S  A  R  L  R  T  F  L  Y  W  P  P

901  TAGTGTTCCTGTTCAGCCCGAGCAGCTTGCAAGTGCTGGATTCTATTACGTGGATCGCRA  960
      S  V  P  V  Q  P  E  Q  L  A  S  A  G  F  Y  Y  V  D  R  N

961  TGATGATGTCAAGTGCCTTTGTTGTGATGGGGCTTGAGATGTTGGGAACCTGGAGATGA  1020
      D  D  V  K  C  L  C  C  D  G  G  L  R  C  W  E  P  G  D  D

1021 CCCCTGGATAGAACACGCCAAATGGTTTCCAAGGTGTGAGTTCTTGATACGGATGAAGGG  1080
      P  W  I  E  H  A  K  W  F  P  R  C  E  F  L  I  R  M  K  G

1081 TCAGGAGTTTGTTGATGAGATTCAAGCTAGATATCCTCATCTTCTTGAGCAGCTGTTGTC  1140
      Q  E  F  V  D  E  I  Q  A  R  Y  P  H  L  L  E  Q  L  L  S
```

Fig. 6C

M-hiap-2

```
        CACTTCAGAGACACCCCAGGAGAAGAAATGCTGACCCTACAGAGACAGTGGTGCATTTTGG
1141    ------+---------+---------+---------+---------+---------+  1200
         T  S  D  T  P  G  E  E  N  A  D  P  T  E  T  V  V  H  F  G

CCCTGGAGAAAGTTCGAAAGATGTCGTCATGATGAGCACGCCTGTGGTTAAAGCAGCCTT
1201    ------+---------+---------+---------+---------+---------+  1260
         P  G  E  S  S  K  D  V  V  M  M  S  T  P  V  V  K  A  A  L

GGAAATGGGCTTCAGTAGGAGCCTGGTGAGACAGACGGTTCAGCGGCAGATCCTGGCCAC
1261    ------+---------+---------+---------+---------+---------+  1320
         E  M  G  F  S  R  S  L  V  R  Q  T  V  Q  R  Q  I  L  A  T

TGGTGAGAACTACAGGACCGTCAATGATATTGTCTCAGTACTTTTGAATGCTGAAGATGA
1321    ------+---------+---------+---------+---------+---------+  1380
         G  E  N  Y  R  T  V  N  D  I  V  S  V  L  L  N  A  E  D  E

GAGAAGAGAAGAGGAGAAGAAAGACAGACTGAAGAGATGGCATCAGGTGACTTATCACT
1381    ------+---------+---------+---------+---------+---------+  1440
         R  R  E  E  E  K  E  R  Q  T  E  E  M  A  S  G  D  L  S  L

GATTCGGAAGAATAGAATGGCCCTCTTTCAACAGTTGACACATGTCCTTCCTATCCTGA
1441    ------+---------+---------+---------+---------+---------+  1500
         I  R  K  N  R  M  A  L  E  Q  Q  L  T  H  V  L  P  I  L  D
```

Fig. 6D

M-hiap-2

```
      TAATCTTCTTGAGGCCAGTGTAATTACAAAACAGGAACATGATATTATTAGACAGAAAAC
1501  ------+---------+---------+---------+---------+---------+  1560
       N  L  E  A  S  V  I  T  K  Q  E  H  D  I  I  R  Q  K  T

ACAGATACCCTTACAAGCAAGAGAGCTTATTGACACCGTTTAGTCAAGGGAAATGCTGC
1561  ------+---------+---------+---------+---------+---------+  1620
       Q  I  P  L  Q  A  R  E  L  I  D  T  V  L  V  K  G  N  A  A

AGCCAACACATCTTCAAAAACTCTCTGAAGGAATTGACTCCACGTTATATGAAAACTTATT
1621  ------+---------+---------+---------+---------+---------+  1680
       A  N  I  F  K  N  S  L  K  G  I  D  S  T  L  Y  E  N  L  F

TGTGGAAAAGAATATGAAGTATATTCCAACAGAAGACGTTTCAGGCTTGTCATTGGAAGA
1681  ------+---------+---------+---------+---------+---------+  1740
       V  E  K  N  M  K  Y  I  P  T  E  D  V  S  G  L  S  L  E  E

GCAGTTGCGGAGATTACAAGAAGAACGAACTTGCAAAGTGTGTATGGACAGAGAGGTTTC
1741  ------+---------+---------+---------+---------+---------+  1800
       Q  L  R  R  L  Q  E  E  R  T  C  K  V  C  M  D  R  E  V  S

TATTGTGTTCATTCCGTGTGGTCATCTAGTAGTCTGCCAGGAATGTGCCCCTTCTCTAAG
1801  ------+---------+---------+---------+---------+---------+  1860
       I  V  F  I  P  C  G  H  L  V  V  C  Q  E  C  A  P  S  L  R
```

Fig. 6E

M-hiap-2

```
      GAAGTGCCCCATCTGCAGGGGACAATCAAGGGGACTGTGCGCACATTTCTCTCATGAGT
1861  ----+---------+---------+---------+---------+---------+  1920
       K  C  P  I  C  R  G  T  I  K  G  T  V  R  T  F  L  S  *

GAAGAATGGTCTGAAAGTATTGTTGGACATCAGAAGCTGTCAGAACAAAGAATGAACTAC
1921  ----+---------+---------+---------+---------+---------+  1980

TGATTTCAGCTCTTCAGCAGGACATTCTACTCTCTTTCAAGATTAGTAATCTTGCTTTAT
1981  ----+---------+---------+---------+---------+---------+  2040

GAAGGGTAGCATTGTATATTTAAGCTTAGTCTGTTGCAAGGGAAGGTCTATGCTGTTGAG
2041  ----+---------+---------+---------+---------+---------+  2100

CTACAGGACTGTGTCTGTGTTCCAGAGCAGGAGTTGGGATGCTTGCTGTGTATGTCCTTCAGGA
2101  ----+---------+---------+---------+---------+---------+  2160

CTTCTTGGGATTGGGAATTTGGGGAAAGCTTTGGAATCCAGTGATGTGGAGCTCAGAAA
2161  ----+---------+---------+---------+---------+---------+  2220

TCCTGGAACCAGTGACTCTGGTACTCAGTAGATAGGGTACCCTGTACTTCTTGGTGCTTT
2221  ----+---------+---------+---------+---------+---------+  2280

TCCAGTGTCTGGGAAATAAGGAGGAATCTGCTGCTGGTAAAAATTGCTGGATGTGAGAAAT
2281  ----+---------+---------+---------+---------+---------+  2340

AGATGAAAGTGTTTTCGGGTGGGGGCCGTGCATCAGTGTAGTGTGTGCAGGATGTATGCAG
2341  ----+---------+---------+---------+---------+---------+  2400

GCCAAACACTGTGTAG
2401  ----+------  2416
```

Alignment of BIR (Baculoviral IAP Repeats) Domains

Baculovirus
 Cp_iap    Cydia pomonella
 Op_iap    Orgyia pseudotsugata

Human
 xiap              IAP on X chromosome
 hiap1, hiap2      two different human IAP genes Mouse
 m-xiap            mouse homologue of human xiap gene Insect
 diap              Drosophila IAP gene, not clearly a homologue of xiap or hiap note on consensus: The consensus line represents amino acids or very similar amino acids which are present in 14 of the 19 BIR sequences at each position. Capitalized residues are those that are in the consensus sequence.

```
                                1                                                                        68
SEQ ID NO:11  Op_iap-1    kaaRLgTYtn WPvgf.leps rMAasGFYYl GrgDeVrCaf CkveitnWvr gDdpetdHkr waPqCpFV
SEQ ID NO:14  Cp_iap-1    eevRLnTFek WPvsf.lspe tMAknGFYYl GrsDeVrCaf CkveimrWke gEdpaadHkk waPqCpFV
SEQ ID NO:15  diap-2      eanRLvTFkd WPnpn.iLpq aLAkAGFYYl nrlDhVkCvw Cngviakwek nDnafeeHkr ffPqCprV
SEQ ID NO:16  m-xiap-1    efnRLkTFan FPsssspvsas tLArAGFLYt GegDtVqCFs ChaaidrWqy gDsavgrHrr isPnCrFI
SEQ ID NO:17  xiap-1      efnRLkTFan FPsgspvsas tLArAGFLYt GegDtVrCFs ChaavdrWqy gDsavgrHrk vsPnCrFI
SEQ ID NO:18  hiap1-1     elyRMsTYst FPagvpvser sLArAGFYYt GvnDkVkCFc CglmldnWkr gDsptekHkk lyPsCrFV
SEQ ID NO:19  hiap2-1     elyRMsTYst FPagvpvser sLArAGFYYt GvnDkVkCFc CglmldnWkl gDspiqkHkq lyPsCsFI
SEQ ID NO:20  m-xiap-2    eeaRLksFqn WPdyahltpr eLAsAGLLYt GadDqVqCFc Cggklknwep cDrawseHrr hfPnCfFv
SEQ ID NO:21  xiap-2      eeaRLksFqn WPdyahltpr eLAsAGLLYt GigDqVqCFc Cggklknwep cDrawseHrr hfPnCfFv
SEQ ID NO:22  hiap1-2     enaRLlTFqt WP.lLflspt dLArAGFYYi GpgDrVaCFa Cggklsnwep kDnamseHlr hfPkCpFI
SEQ ID NO:23  hiap2-2     eeaRFlTYhm WP.lLflsps eLArAGFYYi GpgDrVkCFh Cggglrdwes kDdamseHrr cyPgCkYl
SEQ ID NO:24  yeaRivTFgt  Wiysv..nke qLArAGFYal GegDkVkCFh Cgggltdwkp sEdpwdqHak wyPgCkYl
SEQ ID NO:25  yeaRifTFgt  Wiysv..nke qLArAGFYal GegDkVkCFh Cgggltdwkp sEdpweqHak wyPgCkYl
SEQ ID NO:26  haaRFkTFfn  WPssvlvnpe qLAsAGFYYv GnsDdVkCFh Cdgglrcwes gDdpwvqHak wfPrC Yl
SEQ ID NO:27  haaRMrTFmy  WPssvpvqpe qLAsAGFYYv GrnDdVkCFg Cdgglrcwes gDdpwveHak wfPrCeFl
SEQ ID NO:28  Op_iap-2    eaaRLrTFae WPrglkqrpe eLAeAGFYYt GggDktrCFc Cdgglkdwep dDapwqqHar wydrCeYV
SEQ ID NO:29  Cp_iap-2    eaaRvksFhn WPrcmkqrpe qMAdAGFFYt GygDntkCFy Cdgglkdwep eDvpweqHvr widrCaYV
SEQ ID NO:30  diap-3      vdaRLrTFtd WPisniqpas aLAqAGLlYq kigDqVrCFh CniglrsWqk eDepwieHak wsPkCqFV
SEQ ID NO:31  diap-1      esvRLaTFge WPlnapvsae dlvangFF.. Gtwmeaecdf ChvridrWey gDlvaerHrr ssPiCsmV
SEQ ID NO:2   Consensus   ---RL-TF-- -WP------- -LA-AGFYY- G--D-V-CF- C-----W--  -D-----H-- --P-C-FV
```

```
SEQ ID NO:12  cp-iap      ................  ................  ................  ................
SEQ ID NO:13  diap        ................  ................  ................  .mtelgMeiEs vRLaTFgewP inaPVSaedL
SEQ ID NO:10  m-xiap      ................  ..mtfnsfe gtrtfvladt nkdeEFveEF nRLkTFanFP sssPVSastL
SEQ ID NO:4   xiap        ................  ..mtfnsfe gsktcvpadi nkeeEFveEF nRLkTFanFP sgsPVSastL
SEQ ID NO:6   hiap1       ................  mnivensifl snlmksantf elkyDLscEL yRMsTYstFP agvPVSersL
SEQ ID NO:8   hiap2       ................  ..medstil sdwtns.nkq kmkyDFscEL yRMsTYstFP agvPVSersL
SEQ ID NO:44  consensus   ................  ----------------  ----------F-- -RL-TF--FP ---PVS---L BIR 1
              cp-iap      ................  ................  ................  ................
              diap        .vanGFFaTGk .wleaeChfCh vriDrWeyGD qvaerHrrss PiCsmVla..
              m-xiap      ARAGFLYTGe gDtVqCFsCh aaiDrWqyGD SavgrHrris PnCrFIngFy
              xiap        ARAGFLYTGe gDtVrCFsCh aavDrWqyGD SavgrHrkvs PnCrFIngFy
              hiap1       ARAGFYYTGv nDkVkCFcCg lmlDnWkrGD SptekHkkly PsCrFVqsLn
              hiap2       ARAGFYYTGv nDkVkCFcCg lmlDnWklGD SpigkHkqly PsCsFIqnLv
              consensus   ARAGF-YTG- -D-V-CF-C- ---D-W---GD S----H---- P-C-FI---- cp-iap      ................  ................  ................  ................
              diap        ................  ................  ................  .P nhcgnvprsq
              m-xiap      .....feng aagStnpgig .thSlipgte nsgyfrgsYs gnrnpfapdR
              hiap1       svnnleatsq ptfpssvths .thSlipgte nsgyfrgsYs nspsnpvnsR
              hiap2       s.aslgstsk nt..spmrns fahSlsptle hsslfsgsYs slpppplnsR
              consensus   ---------- ---------- ---S------ ---------Y- ---------R
```

Fig. 8A

```
          151                                                                    200
cp-iap    ..........  .........mSD  lrl.........  ..........  ..EEvRLnTF  ekWPv.sFls
diap      esDnegnsvv  dspescscpD    lll.........  ..........  .EanRLvTF   kdWPn.pnit
m-xiap    ppEthadyll  rtgqvvDiSD    tiyprnp.aM    csEEARLksF  qnWPdyahLt
xiap      psEthadyll  rtgqvvDiSD    tiyprnp.aM    ycEEARLksF  qnWPdyahLt
hiap1     ang.......  .........    EfSa......    lmrssypcpM  nnEnARLlTF  qtwP.ltfls
hiap2     avE.......  .........    DiSs......    srtnpysyaM  stEEEARFlTY  hmWP.ltfls
consensus ----E-----  ---------     -D-SD------  ----------M  -EEARL-TF   --WP----L-

201                                                                    250
                                    BIR 2
cp-iap    PetMAknGFY  YlGrsDeVrC    afCkveimrw    kegEdpaaDH  kkwaPqCPFFV
diap      PqaLakAGFY  YlnrlDhVkC    vwCnGviakW    EknDnAfeEH  kRfFPqCPrV
m-xiap    PrELAsAGLY  YtGadDqVgC    FcCGGKLknW    EPcDrAwSEH  rRHFPnCfFFV
xiap      PrELAsAGLY  YtGigDqVqC    FCCGGKLknW    EPcDrAwSEH  rRHFPnCfFV
hiap1     PtDLArAGFY  YiGpgDrVaC    FaCGGKLsNW    EPkDnAmSEH  lRHFPkCPFFI
hiap2     PsELArAGFY  YiGpgDrVaC    FaCGGKLsNW    EPkDdAmSEH  rRHFPnCPFl
consensus P-ELA-AGFY  Y-G---D-V-C   F-CGGKL-NW    EP-D-A-SEH  -RHFP-CPFV 251                                                                    300
                                                               BIR 3
cp-iap    kgidvcgsiv  ttnniqnttt    hdtiigPahP    kyAheaARvk  sFhnwPrcmk
diap      qmgplie.fa  tgknldelgi    qpttl.PlrP    kyAcvdARlr  TftdwPiSnI
m-xiap    lgrnvnvrse  s.gvssdrnF    pnStnsPrnP    aMAeyeARiv  TFgtWiyS..
xiap      lgrnlnirse  sdavssdrnF    pnStnlPrnP    sMAdyeARif  TFgtWiyS..
hiap1     englqdtsry  tvS.......    Nl........    sMgthaARfk  TFlnwPsSvl
hiap2     ensl.etlrF  siS.......    Nl........    sMgthaARmr  TFmyWPsSvp
consensus ---------F  ---S------    --------P-NP  -MA------AR--  TF---WP-S--
```

Fig. 8B

BIR 3

```
           301                                                                                350
cp-iap     qrpEQMAdAG FFYtGyGDnt KCFyCdGGLk dWepeDvPWe QHvrWFdrCa
diap       qpasaLAqAG LYYqkiGdqv rCFhCniGLr sWqkeDEPWf eHAKWsPkCq
m-xiap     VnkEQLArAG FYalGeGDkV KCFhCgGGLt dWkpsEDPwd QHAKcYPgCk
xiap       VnkEQLArAG FYalGeGDkV KCFhCgGGLt dWkpsEDPwd QHAKWYPgCk
hiap1      VnpEQLAsAG FYYvGnsDdV KCFcCdGGLr cWesgDDPWv QHAKWFPrCe
hiap2      VqpEQLAsAG FYYvGRsDdV KCFgCdGGLr cWesgDDPWv eHAKWFPrCe
consensus  V--EQLA-AG FYY-G-GD-V KCF-C-GGL- -W---DDPW- QHAKWFP-C-

351                                                                                400
cp-iap     Yvqlvkgrdy Vqkvit.... .......... .e........ ..........
diap       FvllaKGpaY VseVlattaa nassqpaTap aptlq..... ..........
m-xiap     YlldeKGQEY InnIhlthp. LeEsLgrTae kt........ ....Ppltk
xiap       YlleqKGQEY InnIhlths. LeEcLvrTte kt........ ....Psltr
hiap1      YlirikGQEY IrqVqasyph LlEqLlsTsD spgdenaess iihlePgedh
hiap2      FlirmKGQEF VdeIggryph LlEqLlsTsD ttgeenadpp iihfgPgess
consensus  Yl---KGQEY ---------- L-E-L--T-- ---------- ----P-----

401                                                                                450
cp-iap     ..acVLpge. .......... .......... dggvVrnaiq rKIlssGcaF stldeLlhDi
diap       ..adVLmdea .......... pakeAltLGi sfkdIKktme eKIqtsGssY lslevLiaDL
m-xiap     kiDdtifqnP adVLmdea.. mVgeAirMGF sfkdIKkime eKIqisGsnY kslevLVaDL
xiap       riDdtifqnP .......... mVgeAirMGF srslVKqtvg rKIfatGenY rlvndLVlDL
hiap1      seDaIMmntP .......... vInaAveMGF nrdlVKqtvl sKIlttGenY ktvndiVsaL
hiap2      seDaVMmntP .......... vVksAleMGF ---------- ---------- ----LV-DL
consensus  --D-V----P -V--A--MGF ---------- ----VK---- -KI---G--Y ----LV-DL
```

Fig. 8C

```
          451                                                500
cp-iap    ..........  ..........  ..........  ..........  ..........
diap      fddagagaal  Evreppe...  ..........  ..........  ..........
m-xiap    vsAqkDnteD  E.........  ..........  ..........  ..........
xiap      vnAqkDsmqD  E.........  ..........  ..........  ..........
hiap1     lnAedEireE  Ererateeke  sndlliirkn  rmalfqhltc  vipildsllt
hiap2     lnAedEkreE  Ekekqaeema  sddlslirkn  rmalfgqltc  vipildnllk
consensus --A-------  E-------- - ---------- ---------- ----------

501                                                550
cp-iap    ..........  ..........  ..........  ..........  ..........
diap      ..........  ..........  ..........  ..........  ..........
m-xiap    ..........  psapfie...  ..nttvstaa  pvsepipe..  ..........
xiap      ..........  ssQtsL....  pcqattskaa  svpipvadsi  pakpqaaeav
hiap1     agiineqehd  vikqktQtsL  Qarelidtil  vkgniaatvf  rnslqeaeav
hiap2     anvinkqehd  iikqktQipL  Qarelidtiw  vkgnaaanif  knclkeidst
consensus ----------  -----Q--L-  Q------- - ---------- ----------
```

Fig. 8D

```
                                                    Ring Zinc Finger
          551                                                                    600
cp-iap    ..tki.. .......... .......   .Ekepq  veDskLCKIC  yveEcivcFV
diap      sniskitdei qkmsvstpng ........   nislEEenRg  LkDarLCKVC  LDeEvgvVFl
m-xiap    ..........  ..........  ........k  diStEEQLRR  LqEEkLsKIC  MDrnIaIVFf
xiap      ..........  ..........  ........k  eiStEEQLRR  LqEEkLCKIC  MDrnIaIVFV
hiap1     lyehlfvqqd  ..........  ikyiptedvs  dlpvEEQLRR  LPEErtCKVC  MDkEVsIVFI
hiap2     lyknlfvdkn  ..........  mkyiptedvs  glSlEEQLRR  LqEErtCKVC  MDkEVsVVFI
consensus ----------  ----------  ----------  --S-EEQLRR  L-EE-LCK-C  MD-EV--VF- 601                                                  635
cp-iap    PCGHvVaCak  CAlSVdkCPM  QRkIVtsvlk  vYFS.
diap      PCGHLatCnq  CApSVanCPM  CRadIkgfvr  tFLS*
m-xiap    PCGHLatCkq  CAeaVdkCPM  CytVItfnqk  iFMS*
xiap      PCGHLVtCkg  CAeaVdkCPM  CytVItfkqk  iFMS*
hiap1     PCGHLVvCkd  CApSlrkCPi  CRstIkgtvr  tFLS*
hiap2     PCGHLVvCge  CApSlrkCPi  CRgIIkgtvr  tFLS.
consensus PCGHLV-C--  CA-SV-KCPM  CR---I----  -FLS-
```

Fig. 8E

Alignment of RZF (Ring Zinc Finger) Domains

Baculovirus
Cp_iap   Cydia pomonella
Op_iap   Orgyia pseudotsugata

Human
xiap           IAP on X chromosome
hiap1, hiap2   two different human IAP genes

Mouse
m-xiap   mouse homologue of human xiap gene

Insect
diap     Drosophilia IAP gene, not clearly a homologue of xiap or hiap note on consensus: The consensus line represents amino acids or very similar amino acids which are present in 6 of the 7 RZF sequences at each position. Capitalized residues are those that are in the consensus sequence.

```
                            1                                                              46
SEQ ID NO:32 hiap2      EqlrrlqEer tCKVCMdkev sVvFiPCGHl vvCgeCApel rkCPiC
SEQ ID NO:33 hiap1      EqlrrlpEer tCKVCMdkev sIvFiPCGHl w CkdCApsl rkCPiC
SEQ ID NO:34 m-xiap     EqlrrlqEek lsKICMdrni aIvFfPCGHl atCkqCAeav dkCPmC
SEQ ID NO:35 xiap       EqlrrlqEek lCKICMdrni aIvFvPCGHl vtCkqCAeav dkCPmC
SEQ ID NO:36 diap       EenrqlkDar lCKVCLdeev gVvFlPCGHl atCnqCApev anCPmC
SEQ ID NO:37 Cp_iap     EkepgveDsk lCKICyveec iVcFvPCGHv vaCakCAlsv dkCPmC
SEQ ID NO:38 Op_iap     aveaevaDdr lCKICLgack tVcFvPCGHv vaCgkCAagv ttCPvC
SEQ ID NO:1  consensus  E------E-- -CKICM---- -V-F-PCGH- ---C---CA- --CP-C
```

Fig. 9

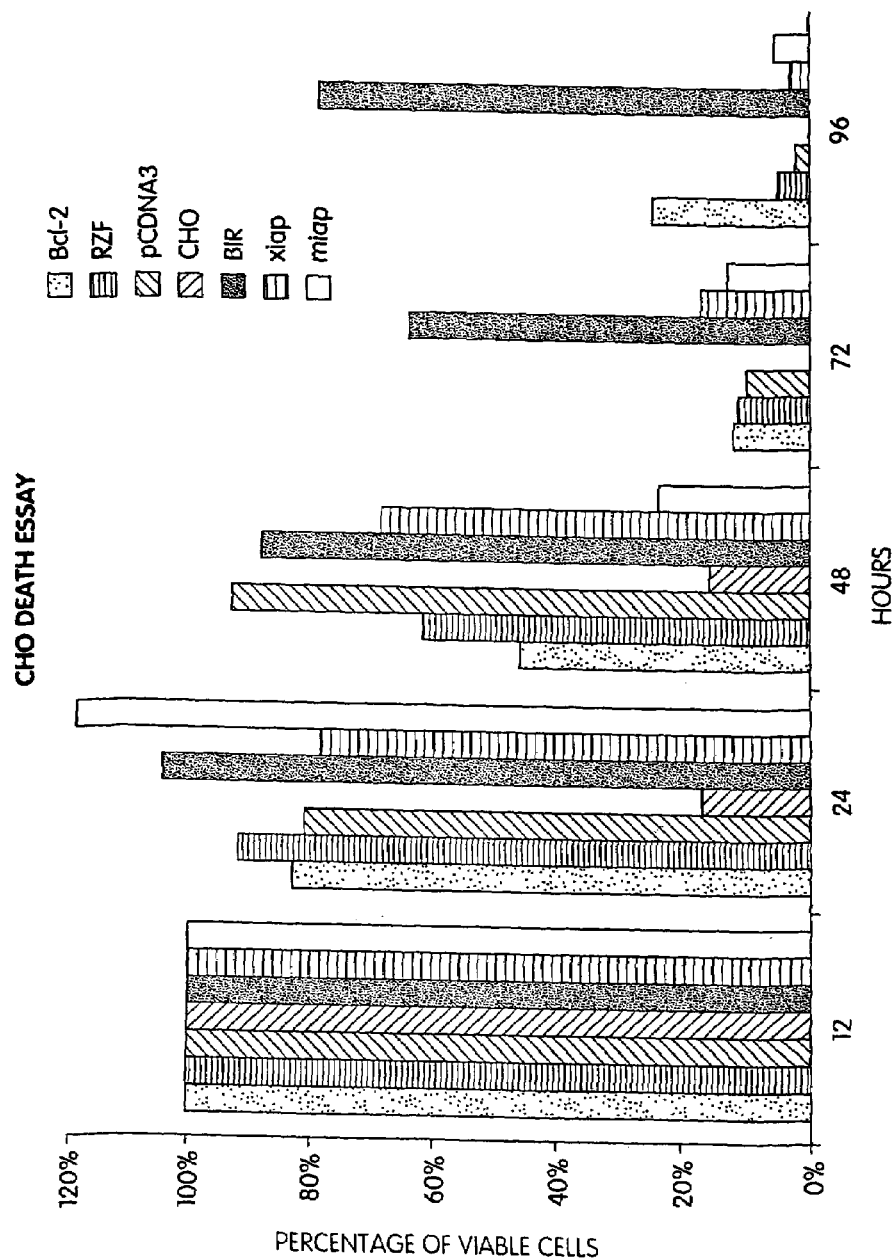

US 7,067,281 B2

MAMMALIAN IAP GENE FAMILY, PRIMERS, PROBES AND DETECTION METHODS

CROSS REFERENCE TO RELATED APPLICATIONS

This application is a continuation of U.S. Ser. No. 09/011,356, filed Sep. 14, 1998 (now U.S. Pat. No. 6,656,704), which is a U.S. National Phase application of PCT/IB/96/01022, filed Aug. 5, 1996, and published in English under PCT article 21(2), which is continuation-in-part of U.S. Ser. No. 08/576,956, filed Dec. 22, 1995 (now U.S. Pat. No. 6,156,535), which is a continuation-in-part of U.S. Ser. No. 08/511,485, filed Aug. 4, 1995 (now U.S. Pat. No. 5,919,912), all of which are hereby incorporated by reference in their entirety.

BACKGROUND OF THE INVENTION

The invention relates to apoptosis.

There are two general ways by which cells die. The most easily recognized way is by necrosis, which is usually caused by an injury that is severe enough to disrupt cellular homeostasis. Typically, the cell's osmotic pressure is disturbed and, consequently, the cell swells and then ruptures. When the cellular contents are spilled into the surrounding tissue space, an inflammatory response often ensues.

The second general way by which cells die is referred to as apoptosis, or programmed cell death. Apoptosis often occurs so rapidly that it is difficult to detect. This may help to explain why the involvement of apoptosis in a wide spectrum of biological processes has only recently been recognized.

The apoptosis pathway has been highly conserved throughout evolution, and plays a critical role in embryonic development, viral pathogenesis, cancer, autoimmune disorders, and neurodegenerative disease. For example, inappropriate apoptosis may cause or contribute to AIDS, Alzheimer's Disease, Parkinson's Disease, Amyotrophic Lateral Sclerosis (ALS), retinitis pigmentosa and other diseases of the retina, myelodysplastic syndrome (e.g. aplastic anemia), toxin-induced liver disease, including alcoholism, and ischemic injury (e.g. myocardial infarction, stroke, and reperfusion injury). Conversely, the failure of an apoptotic response has been implicated in the development of cancer, particularly follicular lymphoma, p53-mediated carcinomas, and hormone-dependent tumors, in autoimmune disorders, such as lupus erythematosis and multiple sclerosis, and in viral infections, including those associated with herpes virus, poxvirus, and adenovirus.

In patients infected with HIV-1, mature $CD4^+$ T lymphocytes respond to stimulation from mitogens or super-antigens by undergoing apoptosis. However, the great majority of these cells are not infected with the virus. Thus, inappropriate antigen-induced apoptosis could be responsible for the destruction of this vital part of the immune system in the early stages of HIV infection.

Baculoviruses encode proteins that are termed inhibitors of apoptosis proteins (IAPs) because they inhibit the apoptosis that would otherwise occur when insect cells are infected by the virus. These proteins are thought to work in a manner that is independent of other viral proteins. The baculovirus IAP genes include sequences encoding a ring zinc finger-like motif (RZF), which is presumed to be directly involved in DNA binding, and two N-terminal domains that consist of a 70 amino acid repeat motif termed a BIR domain (Baculovirus IAP Repeat).

SUMMARY OF THE INVENTION

In general, the invention features a substantially pure DNA molecule, such as a genomic, cDNA, or synthetic DNA molecule, that encodes a mammalian IAP polypeptide. This DNA may be incorporated into a vector, into a cell, which may be a mammalian, yeast, or bacterial cell, or into a transgenic animal or embryo thereof. In preferred embodiments, the DNA molecule is a murine gene (e.g., m-xiap, m-hiap-1, or m-hiap-2) or a human gene (e.g., xiap, hiap-1, or hiap-2). In most preferred embodiments the IAP gene is a human IAP gene. In other various preferred embodiments, the cell is a transformed cell. In related aspects, the invention features a transgenic animal containing a transgene that encodes an IAP polypeptide that is expressed in or delivered to tissue normally susceptible to apoptosis, i.e., to a tissue that may be harmed by either the induction or repression of apoptosis. In yet another aspect, the invention features DNA encoding fragments of IAP polypeptides including the BIR domains and the RZF domains provided herein.

In specific embodiments, the invention features DNA sequences substantially identical to the DNA sequences shown in FIGS. 1–6, or fragments thereof. In another aspect, the invention also features RNA which is encoded by the DNA described herein. Preferably, the RNA is mRNA. In another embodiment the RNA is antisense RNA.

In another aspect, the invention features a substantially pure polypeptide having a sequence substantially identical to one of the IAP amino acid sequences shown in FIGS. 1–6.

In a second aspect, the invention features a substantially pure DNA which includes a promoter capable of expressing the IAP gene in a cell susceptible to apoptosis. In preferred embodiments, the IAP gene is xiap, hiap-1, or hiap-2. Most preferably, the genes are human or mouse genes. The gene encoding HIAP-2 may be the full-length gene, as shown in FIG. 3, or a truncated variant, such as a variant having a deletion of the sequence boxed in FIG. 3.

In preferred embodiments, the promoter is the promoter native to an IAP gene. Additionally, transcriptional and translational regulatory regions are, preferably, those native to an IAP gene. In another aspect, the invention provides transgenic cell lines and transgenic animals. The transgenic cells of the invention are preferably cells that are altered in their apoptotic response. In preferred embodiments, the transgenic cell is a fibroblast, neuronal cell, a lymphocyte cell, a glial cell, an embryonic stem cell, or an insect cell. Most preferably, the neuron is a motor neuron and the lymphocyte is a $CD4^+$ T cell.

In another aspect, the invention features a method of inhibiting apoptosis that involves producing a transgenic cell having a transgene encoding an IAP polypeptide. The transgene is integrated into the genome of the cell in a way is that allows for expression. Furthermore, the level of expression in the cell is sufficient to inhibit apoptosis.

In a related aspect, the invention features a transgenic animal, preferably a mammal, more preferably a rodent, and most preferably a mouse, having either increased copies of at least one IAP gene inserted into the genome (mutant or wild-type), or a knockout of at least one IAP gene in the genome. The transgenic animals will express either an increased or a decreased amount of IAP polypeptide, depending on the construct used and the nature of the genomic alteration. For example, utilizing a nucleic acid molecule that encodes all or part of an IAP to engineer a knockout mutation in an IAP gene would generate an animal with decreased expression of either all or part of the corresponding IAP polypeptide. In contrast, inserting exogenous copies of all or part of an IAP gene into the genome, preferably under the control of active regulatory and promoter elements, would lead to increased expression or the corresponding IAP polypeptide.

In another aspect, the invention features a method of detecting an IAP gene in a cell by contacting the IAP gene, or a portion thereof (which is greater than 9 nucleotides, and preferably greater than 18 nucleotides in length), with a preparation of genomic DNA from the cell. The IAP gene and the genomic DNA are brought into contact under conditions that allow for hybridization (and therefore, detection) of DNA sequences in the cell that are at least 50% identical to the DNA encoding HIAP-1, HIAP-2, or XIAP polypeptides.

In another aspect, the invention features a method of producing an IAP polypeptide. This method involves providing a cell with DNA encoding all or part of an IAP polypeptide (which is positioned for expression in the cell), culturing the cell under conditions that allow for expression of the DNA, and isolating the IAP polypeptide. In preferred embodiments, the IAP polypeptide is expressed by DNA that is under the control of a constitutive or inducible promotor. As described herein, the promotor may be a heterologous promotor.

In another aspect, the invention features substantially pure mammalian IAP polypeptide. Preferably, the polypeptide includes an amino acid sequence that is substantially identical to all, or to a fragment of, the amino acid sequence shown in any one of FIGS. 1–4. Most preferably, the polypeptide is the XIAP, HIAP-1, HIAP-2, M-XIAP, M-HIAP-1, or M-HIAP-2 polypeptide. Fragments including one or more BIR domains (to the exclusion of the RZF), the RZF domain (to the exclusion of the BIR domains), and a RZF domain with at least one BIR domain, as provided herein, are also a part of the invention.

In another aspect, the invention features a recombinant mammalian polypeptide that is capable of modulating apoptosis. The polypeptide may include at least a RZF domain and a BIR domain as defined herein. In preferred embodiments, the invention features (a) a substantially pure polypeptide, and (b) an oligonucleotide encoding the polypeptide. In instances were the polypeptide includes a RZF domain, the RZF domain will have a sequence conforming to: Glu-Xaa1-Xaa1-Xaa1- Xaa1-Xaa1-Xaa1-Xaa2-Xaa1-Xaa1-Xaa1-Cys-Lys-Xaa3-Cys-Met-Xaa1-Xaa1-Xaa1-Xaa1-Xaa1-Xaa3-Xaa1-Phe-Xaa1-Pro-Cys-Gly-His-Xaa1-Xaa1-Xaa1-Cys-Xaa1-Xaa1-Cys-Ala-Xaa1-Xaa1-Xaa1-Xaa1-Xaa1-Cys-Pro-Xaa1-Cys, where Xaa1 is any amino acid, Xaa2 is Glu or Asp, Xaa3 is Val or Ile (SEQ ID NO: 1); and where the polypeptide includes at least one BIR domain, the BIR domain will have a sequence conforming to: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa1-Xaa1-Xaa1-Xaa1-Pro-Xaa1-Cys-Xaa1-Phe-Val, where Xaa1 may be any amino acid and Xaa2 may be any amino acid or may be absent (SEQ ID NO: 2).

In various preferred embodiments the polypeptide has at least two or, more preferably at least three BIR domains, the RZF domain has one of the IAP sequences shown in FIG. 6, and the BIR domains are comprised of BIR domains shown in FIG. 5. In other preferred embodiments the BIR domains are at the amino terminal end of the protein relative to the RZF domain, which is at or near the carboxyl terminus of the polypeptide.

In another aspect, the invention features an IAP gene isolated according to the method involving: (a) providing a sample of DNA; (b) providing a pair of oligonucleotides having sequence homology to a conserved region of an IAP disease-resistance gene; (c) combining the pair of oligonucleotides with the cell DNA sample under conditions suitable for polymerase chain reaction-mediated DNA amplification; and (d) isolating the amplified IAP gene or fragment thereof.

In preferred embodiments, the amplification is carried out using a reverse-transcription polymerase chain reaction, for example, the RACE method. In another aspect, the invention features an IAP gene isolated according to the method involving: (a) providing a preparation of DNA; (b) providing a detectably labelled DNA sequence having homology to a conserved region of an IAP gene; (c) contacting the preparation of DNA with the detectably-labelled DNA sequence under hybridization conditions providing detection of genes having 50% or greater nucleotide sequence identity; and (d) identifying an IAP gene by its association with the detectable label.

In another aspect, the invention features an IAP gene isolated according to the method involving: (a) providing a cell sample; (b) introducing by transformation into the cell sample a candidate IAP gene; (c) expressing the candidate IAP gene within the cell sample; and (d) determining whether the cell sample exhibits an altered apoptotic response, whereby a response identifies an IAP gene.

In another aspect, the invention features a method of identifying an IAP gene in a cell, involving: (a) providing a preparation of cellular DNA (for example, from the human genome or a cDNA library (such as a cDNA library isolated from a cell type which undergoes apoptosis); (b) providing a detectably-labelled DNA sequence (for example, prepared by the methods of the invention) having homology to a conserved region of an IAP gene; (c) contacting the preparation of cellular DNA with the detectably-labelled DNA sequence under hybridization conditions providing detection of genes having 50% nucleotide or greater sequence identity; and (d) identifying an IAP gene by its association with the detectable label.

In another aspect, the invention features a method of isolating an IAP gene from a recombinant library, involving: (a) providing a recombinant library; (b) contacting the library with a detectably-labelled gene fragment produced according to the PCR method of the invention under hybridization conditions providing detection of genes having 50% or greater nucleotide sequence identity; and (c) isolating an IAP gene by its association with the detectable label. In another aspect, the invention features a method of identifying an IAP gene involving: (a) providing a cell tissue sample; (b) introducing by transformation into the cell sample a candidate IAP gene; (c) expressing the candidate IAP gene within the cell sample; and (d) determining whether the cell sample exhibits inhibition of apoptosis, whereby a change in (i.e. modulation of) apoptosis identifies an IAP gene. Preferably, the cell sample is a cell type that may be assayed for apoptosis (e.g., T cells, B cells, neuronal cells, baculovirus-infected insect cells, glial cells, embryonic stem cells, and fibroblasts). The candidate IAP gene is obtained, for example, from a cDNA expression library, and the response assayed is the inhibition of apoptosis.

In another aspect, the invention features a method of inhibiting apoptosis in a mammal wherein the method includes: (a) providing DNA encoding at least one IAP polypeptide to a cell that is susceptible to apoptosis; wherein the DNA is integrated into the genome of the cell and is positioned for expression in the cell; and the IAP gene is under the control of regulatory sequences suitable for controlled expression of the gene(s); wherein the IAP transgene is expressed at a level sufficient to inhibit apoptosis relative to a cell lacking the IAP transgene. The DNA integrated into the genome may encode all or part of an IAP polypeptide. It may, for example, encode a ring zinc finger and one or more BIR domains. In contrast, it may encode either the ring zinc finger alone, or one or more BIR domains alone. Skilled artisans will appreciate that IAP polypeptides may also be administered directly to inhibit undesirable apoptosis.

In a related aspect, the invention features a method of inhibiting apoptosis by producing a cell that has integrated, into its genome, a transgene that includes the IAP gene, or a fragment thereof. The IAP gene may be placed under the control of a promoter providing constitutive expression of the IAP gene. Alternatively, the IAP transgene may be placed under the control of a promoter that allows expression of the gene to be regulated by environmental stimuli. For example, the IAP gene may be expressed using a tissue-specific or cell type-specific promoter, or by a promoter that is activated by the introduction of an external signal or agent, such as a chemical signal or agent. In preferred embodiments the cell is a lymphocyte, a neuronal cell, a glial cell, or a fibroblast. In other embodiments, the cell in an HIV-infected human, or in a mammal suffering from a neurodegenerative disease, an ischemic injury, a toxin-induced liver disease, or a myelodysplastic syndrome.

In a related aspect, the invention provides a method of inhibiting apoptosis in a mammal by providing an apoptosis-inhibiting amount of IAP polypeptide. The IAP polypeptide may be a full-length polypeptide, or it may be one of the fragments described herein.

In another aspect, the invention features a purified antibody that binds specifically to an IAP family protein. Such an antibody may be used in any standard immunodetection method for the identification of an IAP polypeptide. Preferably, the antibody binds specifically to XIAP, HIAP-1, or HIAP-2. In various embodiments, the antibody may react with other IAP polypeptides or may be specific for one or a few IAP polypeptides. The antibody may be a monoclonal or a polyclonal antibody. Preferably, the antibody reacts specifically with only one of the IAP polypeptides, for example, reacts with murine and human XIAP, but not with HIAP-1 or HIAP-2 from other mammalian species.

The antibodies of the invention may be prepared by a variety of methods. For example, the IAP polypeptide, or antigenic fragments thereof, can be administered to an animal in order to induce the production of polyclonal antibodies. Alternatively, antibodies used as described herein may be monoclonal antibodies, which are prepared using hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas,* Elsevier, N.Y., 1981). The invention features antibodies that specifically bind human or murine IAP polypeptides, or fragments thereof. In particular the invention features "neutralizing" antibodies. By "neutralizing" antibodies is meant antibodies that interfere with any of the biological activities of IAP polypeptides, particularly the ability of IAPs to inhibit apoptosis. The neutralizing antibody may reduce the ability of IAP polypeptides to inhibit polypeptides by, preferably 50%, more preferably by 70, and most preferably by 90% or more. Any standard assay of apoptosis, including those described herein, may be used to assess neutralizing antibodies.

In addition to intact monoclonal and polyclonal anti-IAP antibodies, the invention features various genetically engineered antibodies, humanized antibodies, and antibody fragments, including F(ab')2, Fab', Fab, Fv and sFv fragments. Antibodies can be humanized by methods known in the art, e.g., monoclonal antibodies with a desired binding specificity can be commercially humanized (Scotgene, Scotland; Oxford Molecular, Palo Alto, Calif.). Fully human antibodies, such as those expressed in transgenic animals, are also features of the invention (Green et al., Nature Genetics 7:13, 1994).

Ladner (U.S. Pat. Nos. 4,946,778 and 4,704,692) describes methods for preparing single polypeptide chain antibodies. Ward et al. (Nature 341:544, 1989) describe the preparation of heavy chain variable domains, which they term "single domain antibodies," which have high antigen-binding affinities. McCafferty et al. (Nature 348:552, 1990) show that complete antibody V domains can be displayed on the surface of fd bacteriophage, that the phage bind specifically to antigen, and that rare phage (one in a million) can be isolated after affinity chromatography. Boss et al. (U.S. Pat. No. 4,816,397) describe various methods for producing immunoglobulins, and immunologically functional fragments thereof, which include at least the variable domains of the heavy and light chain in a single host cell. Cabilly et al. (U.S. Pat. No. 4,816,567) describe methods for preparing chimeric antibodies.

In another aspect, the invention features a method of identifying a compound that modulates apoptosis. The method includes providing a cell expressing an IAP polypeptide, contacting the cell with a candidate compound, and monitoring the expression of an IAP gene. An alteration in the level of expression of the IAP gene indicates the presence of a compound which modulates apoptosis. The compound may be an inhibitor or an enhancer of apoptosis. In various preferred embodiments, the cell is a fibroblast, a neuronal cell, a glial cell, a lymphocyte (T cell or B cell), or an insect cell; the polypeptide expression being monitored is XIAP, HIAP-1, HIAP-2, M-XIAP, M-HIAP-1, or M-HIAP-2 (i.e., human or murine).

In a related aspect, the invention features methods of detecting compounds that modulate apoptosis using the interaction trap technology and IAP polypeptides, or fragments thereof, as a component of the bait. In preferred embodiments, the compound being tested as a modulator of apoptosis is also a polypeptide.

In another aspect, the invention features a method for diagnosing a cell proliferation disease, or an increased likelihood of such a disease, using an IAP nucleic acid probe or antibody. Preferably, the disease is a cancer. Most preferably, the disease is selected from the group consisting of promyelocytic leukemia, a HeLa-type carcinoma, chronic myelogenous leukemia (preferably using xiap or hiap-2 related probes), lymphoblastic leukemia (preferably using a xiap related probe), Burkitt's lymphoma (preferably using an hiap-1 related probe), colorectal adenocarcinoma, lung carcinoma, and melanoma (preferably using a xiap probe). Preferably, a diagnosis is indicated by a 2-fold increase in expression or activity, more preferably, at least a 10-fold increase in expression or activity.

Skilled artisans will recognize that a mammalian IAP, or a fragment thereof (as described herein), may serve as an active ingredient in a therapeutic composition. This composition, depending on the IAP or fragment included, may be used to modulate apoptosis and thereby treat any condition that is caused by a disturbance in apoptosis.

In addition, apoptosis may be induced in a cell by administering to the cell a negative regulator of the IAP-dependent anti-apoptotic pathway. The negative regulator may be, but is not limited to, an IAP polypeptide that includes a ring zinc finger, and an IAP polypeptide that includes a ring zinc finger and lacks at least one BIR domain. Alternatively, apoptosis may be induced in the cell by administering a gene encoding an IAP polypeptide, such as these two polypeptides. In yet another method, the negative regulator may be a purified antibody, or a fragment thereof, that binds specifically to an IAP polypeptide. For example, the antibody may bind to an approximately 26 kDa cleavage product of an IAP polypeptide that includes at least one BIR domain but lacks a ring zinc finger domain. The negative regulator may also be an IAP antisense mRNA molecule.

As summarized above, an IAP nucleic acid, or an IAP polypeptide may be used to modulate apoptosis. Furthermore, an IAP nucleic acid, or an IAP polypeptide, may be used in the manufacture of a medicament for the modulation of apoptosis.

By "IAP gene" is meant a gene encoding a polypeptide having at least one BIR domain and a ring zinc finger domain which is capable of modulating (inhibiting or enhancing) apoptosis in a cell or tissue when provided by other intracellular or extracellular delivery methods. In preferred embodiments the IAP gene is a gene having about 50% or greater nucleotide sequence identity to at least one of the IAP amino acid encoding sequences of FIGS. 1–4 or portions thereof. Preferably, the region of sequence over which identity is measured is a region encoding at least one BIR domain and a ring zinc finger domain. Mammalian IAP genes include nucleotide sequences isolated from any mammalian source. Preferably, the mammal is a human.

The term "IAP gene" is meant to encompass any member of the family of apoptosis inhibitory genes, which are characterized by their ability to modulate apoptosis. An IAP gene may encode a polypeptide that has at least 20%, preferably at least 30%, and most preferably at least 50% amino acid sequence identity with at least one of the conserved regions of one of the IAP members described herein (i.e., either the BIR or ring zinc finger domains from the human or murine xiap, hiap-1 and hiap-2). Representative members of the IAP gene family include, without limitation, the human and murine xiap, hiap-1, and hiap-2 genes.

By "IAP protein" or "IAP polypeptide" is meant a polypeptide, or fragment thereof, encoded by an IAP gene.

By "BIR domain" is meant a domain having the amino acid sequence of the consensus sequence: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa1-Xaa1-Xaa1-Xaa1-Pro-Xaa1-Cys-Xaa1-Phe-Val, wherein Xaa1 is any amino acid and Xaa2 is any amino acid or is absent (SEQ ID NO: 2). Preferably, the sequence is substantially identical to one of the BIR domain sequences provided herein for XIAP, HIAP-1, or HIAP-2.

By "ring zinc finger" or "RZF" is meant a domain having the amino acid sequence of the consensus sequence: Glu-Xaa1-Xaa1-Xaa1-Xaa1-Xaa1-Xaa1-Xaa2-Xaa1-Xaa1-Xaa1-Cys-Lys-Xaa3-Cys-Met-Xaa1-Xaa1-Xaa1-Xaa1-Xaa1-Xaa3-Xaa1-Phe-Xaa1-Pro-Cys-Gly-His-Xaa1-Xaa1-Xaa1-Cys-Xaa1-Xaa1-Cys-Ala- Xaa1-Xaa1-Xaa1-Xaa1-Xaa1-Cys-Pro-Xaa1-Cys, wherein Xaa1 is any amino acid, Xaa2 is Glu or Asp, and Xaa3 is Val or Ile (SEQ ID NO: 1).

Preferably, the sequence is substantially identical to the RZF domains provided herein for the human or murine XIAP, HIAP-1, or HIAP-2.

By "modulating apoptosis" or "altering apoptosis" is meant increasing or decreasing the number of cells that would otherwise undergo apoptosis in a given cell population. Preferably, the cell population is selected from a group including T cells, neuronal cells, fibroblasts, or any other cell line known to undergo apoptosis in a laboratory setting (e.g., the baculovirus infected insect cells). It will be appreciated that the degree of modulation provided by an IAP or modulating compound in a given assay will vary, but that one skilled in the art can determine the statistically significant change in the level of apoptosis which identifies an IAP or a compound which modulates an IAP.

By "inhibiting apoptosis" is meant any decrease in the number of cells which undergo apoptosis relative to an untreated control. Preferably, the decrease is at least 25%, more preferably the decrease is 50%, and most preferably the decrease is at least one-fold.

By "polypeptide" is meant any chain of more than two amino acids, regardless of post-translational modification such as glycosylation or phosphorylation.

By "substantially identical" is meant a polypeptide or nucleic acid exhibiting at least 50%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at, least 60 nucleotides, more preferably at least 75 nucleotides, and most preferably 110 nucleotides.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably, the polypeptide is an IAP polypeptide that is at least 75%, more preferably at least 90%, and most preferably at least 99%, by weight, pure. A substantially pure IAP polypeptide may be obtained, for example, by extraction from a natural source (e.g. a fibroblast, neuronal cell, or lymphocyte) by expression of a recombinant nucleic acid encoding an IAP polypeptide, or by chemically synthesizing the protein. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes. By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an IAP polypeptide.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic mammalian (e.g., rodents such as rats or mice) and the DNA (transgene) is inserted by artifice into the nuclear genome.

By "transformation" is meant any method for introducing foreign molecules into a cell. Lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "positioned for expression" is meant that the DNA molecule is positioned adjacent to a DNA sequence which directs transcription and translation of the sequence (i.e., facilitates the production of, e.g., an IAP polypeptide, a recombinant protein or a RNA molecule).

By "reporter gene" is meant a gene whose expression may be assayed; such genes include, without limitation, glucuronidase (GUS), luciferase, chloramphenicol transacetylase (CAT), and lacZ.

By "promoter" is meant minimal sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins are bound to the regulatory sequences).

By "conserved region" is meant any stretch of six or more contiguous amino acids exhibiting at least 30%, preferably 50%, and most preferably 70% amino acid sequence identity between two or more of the IAP family members, (e.g., between human HIAP-1, HIAP-2, and XIAP). Examples of preferred conserved regions are shown (as boxed or designated sequences) in FIGS. 5–7 and Tables 1 and 2, and include, without limitation, BIR domains and ring zinc finger domains.

By "detectably-labelled" is meant any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling).

By "antisense," as used herein in reference to nucleic acids, is meant a nucleic acid sequence, regardless of length, that is complementary to the coding strand of a gene.

By "purified antibody" is meant antibody which is at least 60%, by weight, free from proteins and naturally occurring organic molecules with which it is naturally associated. Preferably, the preparation is at least 75%, more preferably 90%, and most preferably at least 99%, by weight, antibody, e.g., an IAP specific antibody. A purified antibody may be obtained, for example, by affinity chromatography using recombinantly-produced protein or conserved motif peptides and standard techniques.

By "specifically binds" is meant an antibody that recognizes and binds a protein but that does not substantially recognize and bind other molecules in a sample, e.g., a biological sample, that naturally includes protein.

Other features and advantages of the invention will be apparent from the following description of the preferred embodiments thereof, and from the claims.

BRIEF DESCRIPTION OF THE DRAWINGS

FIGS. 1A–1G is the human xiap cDNA sequence (SEQ ID NO: 3) and the XIAP polypeptide sequence (SEQ ID NO: 4).

FIGS. 2A–2H is the human hiap-1 cDNA sequence (SEQ ID NO: 5) and the HIAP-1 polypeptide sequence (SEQ ID NO: 6).

FIGS. 3A–3G is the human hiap-2 cDNA sequence (SEQ ID NO: 7) and the HIAP-2 polypeptide sequence (SEQ ID NO: 8). The sequence absent in the hiap-2-Δ variant is boxed.

FIGS. 4A–4F is the murine xiap cDNA sequence (SEQ ID NO: 9) and encoded murine XIAP polypeptide sequence (SEQ ID NO: 10).

FIGS. 5A–5F is the murine hiap-1 cDNA sequence (SEQ ID NO: 39) and the encoded murine HIAP-1 polypeptide sequence (SEQ ID NO: 40).

FIGS. 6A–6F is the murine hiap-2 cDNA sequence (SEQ ID NO: 41) and the encoded murine HIAP-2 polypeptide (SEQ ID NO: 42).

FIG. 7 is a representation of the alignment of the BIR domains of IAP proteins (SEQ ID NOs: 11 and 14–31).

FIGS. 8A–8E is a representation of the alignment of human IAP polypeptides with diap, cp-iap, and the IAP consensus sequence (SEQ ID NOs: 4, 6, 8, 10, 12, and 13).

FIG. 9 is a representation of the alignment of the ring finger domains of IAP proteins (SEQ ID NOs: 32–38).

FIGS. 15A and 15B are bar graphs depicting the percentage of viable CHO cells following transient transfection with the cDNA constructs shown and subsequent serum withdrawal.

FIG. 16B=20 μM menadione).

DETAILED DESCRIPTION

I. IAP Genes and Polypeptides

A new class of mammalian proteins that modulate apoptosis (IAPs) and the genes that encode these proteins have been discovered. The IAP proteins are characterized by the presence of a ring zinc finger domain (RZF; FIG. 9) and at least one BIR domain, as defined by the boxed consensus sequences shown in FIGS. 7 and 8, and by the sequence domains listed in Tables 1 and 2. As examples of novel IAP genes and proteins, the cDNA sequences and amino acid sequences for human IAPs (HIAP-1, HIAP-2, and XIAP) and a new murine inhibitor of apoptosis, XIAP, are provided. Additional members of the mammalian IAP family (including homologs from other species and mutant sequences) may be isolated using standard cloning techniques and the conserved amino acid sequences, primers, and probes provided herein and known in the art. Furthermore, IAPs include those proteins lacking the ring zinc finger, as further described below.

TABLE 1

NUCLEOTIDE POSITION OF CONSERVED DOMAINS*

|  | BIR-1 | BIR-2 | BIR-3 | Ring Zinc Finger |
|---|---|---|---|---|
| h-xiap | 109–312 | 520–723 | 826–1023 | 1348–1485 |
| m-xiap | 202–405 | 613–816 | 916–1113 | 1438–1575 |
| h-hiap-1 | 273–476 | 693–893 | 951–1154 | 1824–1961 |
| m-hiap-1 | 251–453 | 670–870 | 928–1131 | 1795–1932 |
| h-hiap-2 | 373–576 | 787–987 | 1042–1245 | 1915–2052 |
| m-hiap-2 | 215–418 | 608–808 | 863–1066 | 1763–1876 |

*Positions indicated correspond to those shown in FIGS. 1–4.

TABLE 2

AMINO ACID POSITION OF CONSERVED DOMAINS*

|  | BIR-1 | BIR-2 | BIR-3 | Ring Zinc Finger |
|---|---|---|---|---|
| h-XAIP | 26–93 | 163–230 | 265–330 | 439–484 |
| m-XIAP | 26–93 | 163–230 | 264–329 | 438–483 |
| h-HIAP1 | 29–96 | 169–235 | 255–322 | 546–591 |
| m-HIAP1 | 29–96 | 169–235 | 255–322 | 544–589 |
| h-HIAP2 | 46–113 | 184–250 | 269–336 | 560–605 |
| m-HIAP2 | 25–92 | 156–222 | 241–308 | 541–578 |

*Positions indicated correspond to those shown in FIGS. 1–4.

Recognition of the mammalian IAP family has provided an emergent pattern of protein structure. Recognition of this pattern allows proteins having a known, homologous sequence but unknown function to be classified as putative inhibitors of apoptosis. A *Drosophila* gene, now termed diap, was classified in this way (for sequence information see Genbank Accession Number M96581 and FIG. 6). The conservation of these proteins across species indicates that the apoptosis signalling pathway has been conserved throughout evolution.

The IAP proteins may be used to inhibit the apoptosis that occurs as part of numerous disease processes or disorders. For example, IAP polypeptides or nucleic acid encoding IAP polypeptides may be administered for the treatment or prevention of apoptosis that occurs as a part of AIDS, neurodegenerative diseases, ischemic injury, toxin-induced liver disease and myelodysplastic syndromes. Nucleic acid encoding the IAP polypeptide may also be provided to inhibit apoptosis.

II. Cloning of IAP Genes

A. Human xiap

Figure 10A:
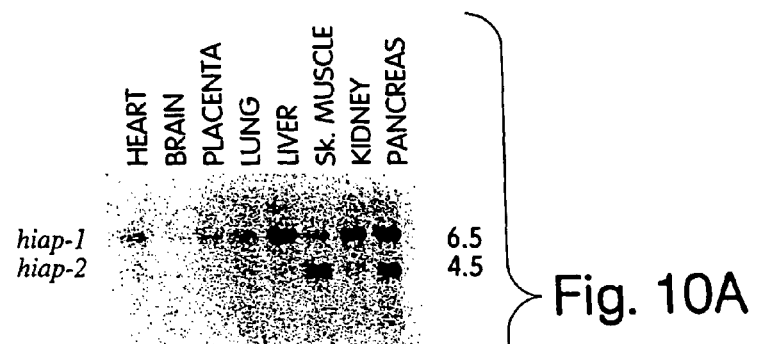
FIGS. 10A–10C is a photograph of a northern blot illustrating human hiap-1 and hiap-2 mRNA expression in human tissues.
Figure 10B:
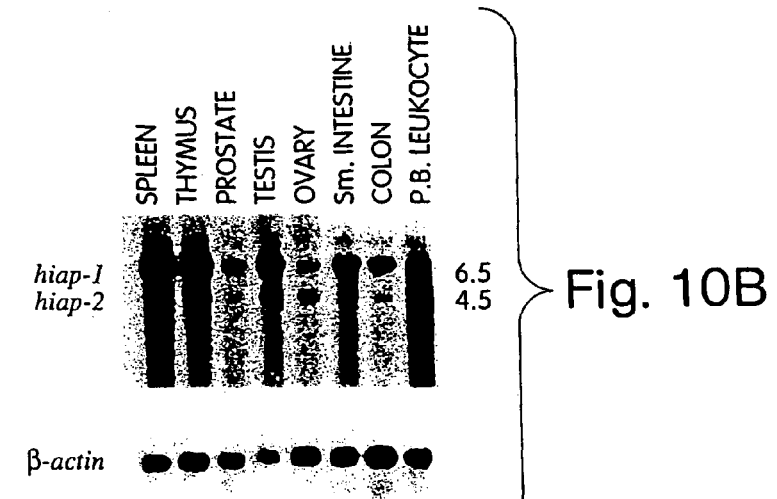
Figure 10C:
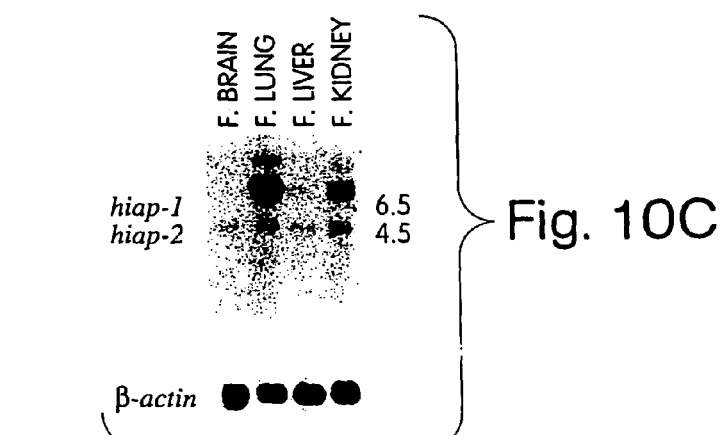
Figure 11A:
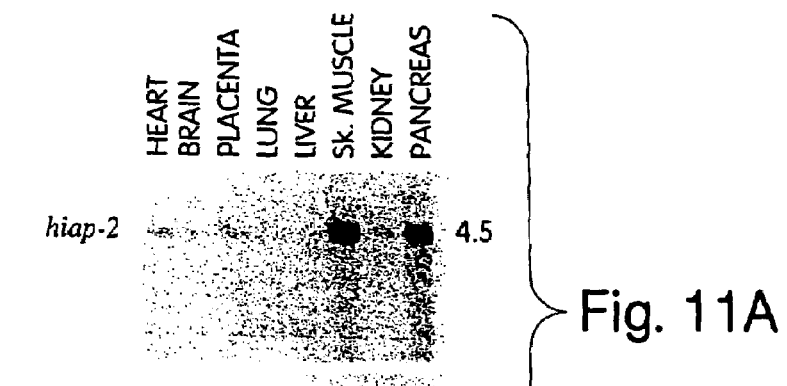
FIGS. 11A–11C is a photograph of a northern blot illustrating human hiap-2 mRNA expression in human tissues.
Figure 11B:
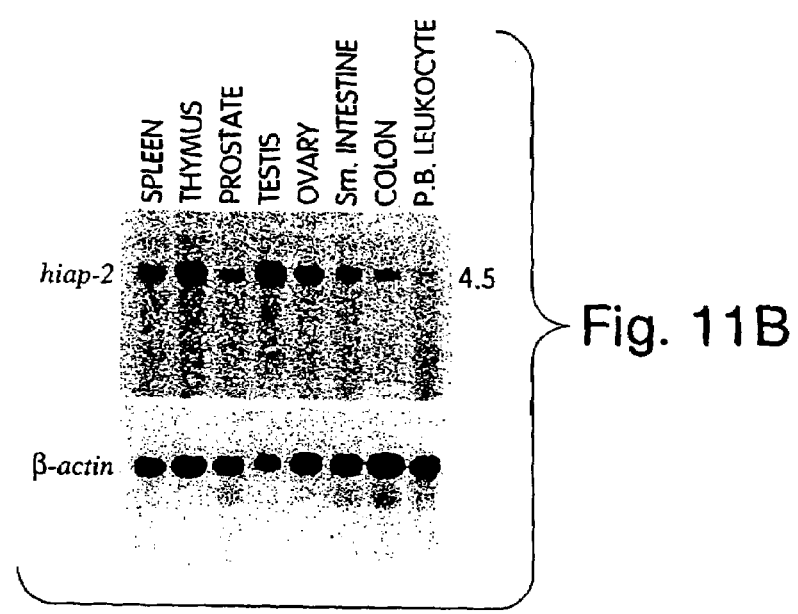
Figure 11C:
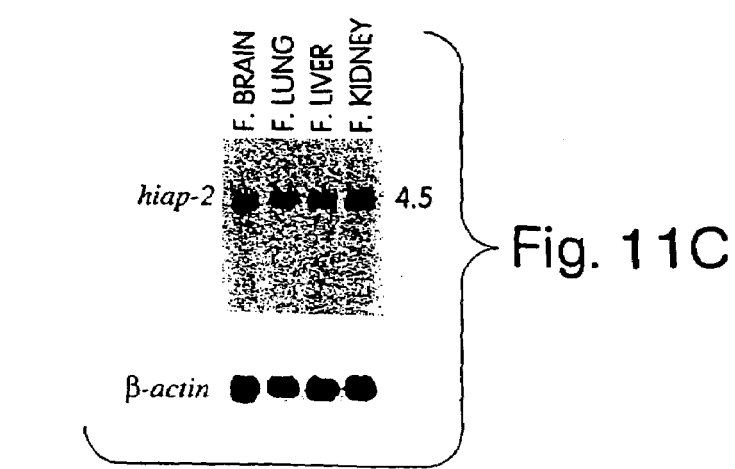
Figure 12A:
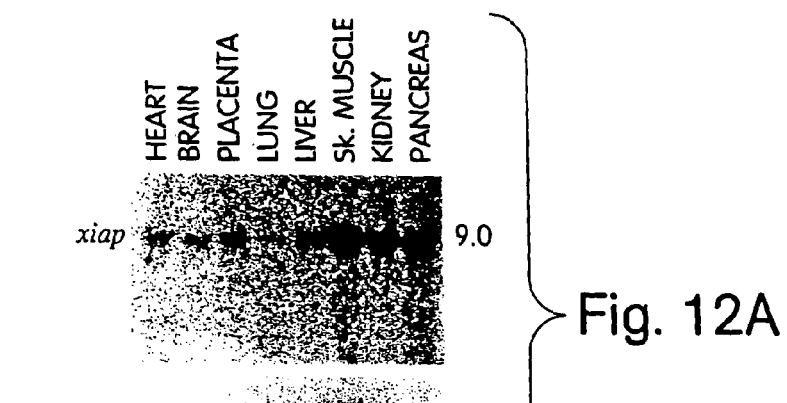
FIGS. 12A–12C is a photograph of a northern blot illustrating human xiap mRNA expression in human tissues.
Figure 12B:
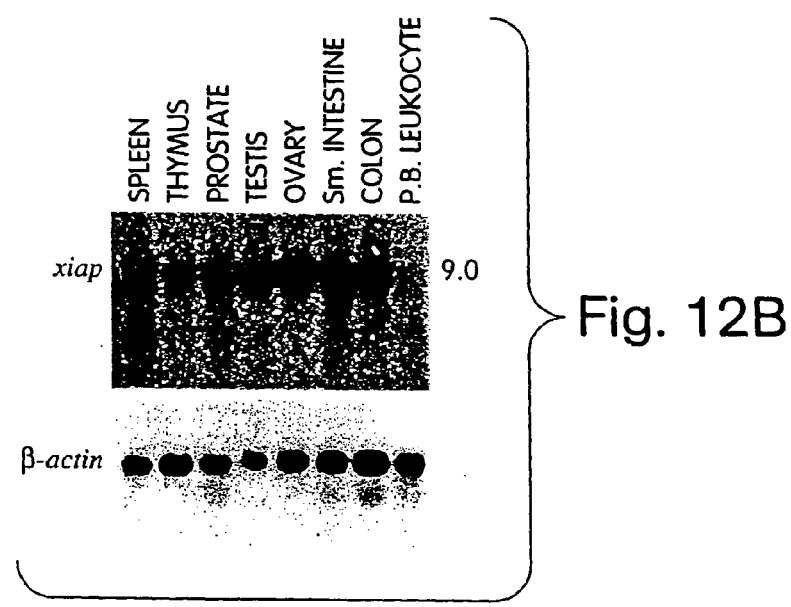
Figure 12C:
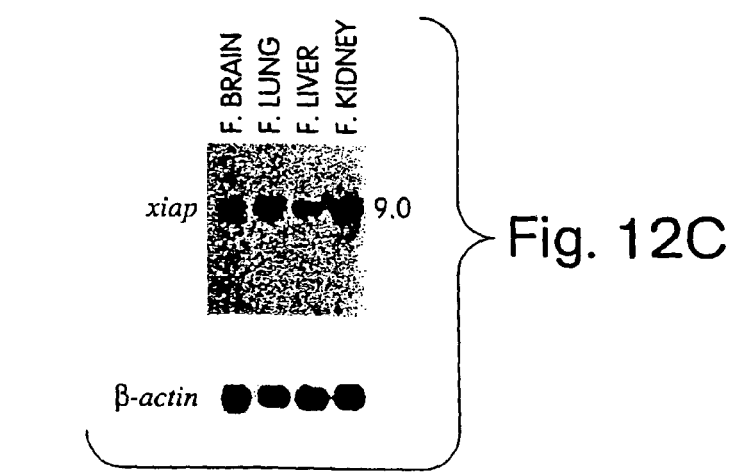

The search for human genes involved in apoptosis resulted in the identification of an X-linked sequence tag site (STS) in the GenBank database, which demonstrated strong homology with the conserved RZF domain of CpIAP and OpIAP, the two baculovirus genes known to inhibit apoptosis (Clem et al., Mol. Cell Biol. 14:5212, 1994; Birnbaum et al., J. Virol. 68:2521, 1994). Screening a human fetal brain ZapII cDNA library (Stratagene, La Jolla, Calif.) with this STS resulted in the identification and cloning of xiap (for X-linked Inhibitor of Apoptosis Protein gene). The human gene has a 1.5 kb coding sequence that includes three BIR domains (Crook et al., J. Virol. 67:2168, 1993; Clem et al., Science 254:1388, 1991; Birnbaum et al., J. Virol. 68:2521, 1994) and a zinc finger. Northern blot analysis with xiap revealed message greater than 7 kb, which is expressed in various tissues, particularly liver and kidney (FIG. 12). The large size of the transcript reflects large 5' and 3' untranslated regions.

B. Human hiap-1 and hiap-2

The hiap-1 and hiap-2 genes were cloned by screening a human liver library (Stratagene Inc., LaJolla, Calif.) with a probe including the entire xiap coding region at low stringency (the final wash was performed at 40° C. with 2×SSC, 10% SDS; FIGS. 2 and 3). The hiap-1 and hiap-2 genes were also detected independently using a probe derived from an expressed sequence tag (EST; GenBank Accession No. T96284), which includes a portion of a BIR domain. The EST sequence was originally isolated by the polymerase chain reaction; a cDNA library was used as a template and amplified with EST-specific primers. The DNA amplified probe was then used to screen the human liver cDNA library for full-length hiap coding sequences. A third DNA was subsequently detected that includes the hiap-2 sequence but that appears to lack one exon, presumably due to alternative mRNA splicing (see boxed region in FIG. 3). The expression of hiap-1 and hiap-2 in human tissues as assayed by northern blot analysis is shown in FIGS. 8 and 9.

C. m-xiap

Fourteen cDNA and two genomic clones were identified by screening a mouse embryo λgt11 cDNA library (Clontech, Palo Alto, Calif.) and a mouse FIX II genomic library with a xiap cDNA probe, respectively. A cDNA contig spanning 8.0 kb was constructed using 12 overlapping mouse clones. Sequence analysis revealed a coding sequence of approximately 1.5 kb. The mouse gene, m-xiap, encodes a polypeptide with striking homology to human XIAP at and around the initiation methionine, the stop codon, the three BIR domains, and the RZF domain. As with the human gene, the mouse homologue contains large 5' and 3' UTRs, which could produce a transcript as large as 7–8 kb.

Analysis of the sequence and restriction map of m-xiap further delineate the structure and genomic organization of m-xiap. Southern blot analysis and inverse PCR techniques (Groden et al., Cell 66:589, 1991) can be employed to map exons and define exon-intron boundaries.

Antisera can be raised against a M-XIAP fusion protein that was obtained from, for example, E. coli using a bacterial expression system. The resulting antisera can be used along with northern blot analysis to analyze the spatial and temporal expression of m-xiap in the mouse.

D. m-hiap-1 and m-hiap-2

The murine homologs of hiap-1 and hiap-2 were cloned and sequenced in the same general manner as m-xiap using the human hiap-1 and hiap-2 sequences as probes. Cloning of m-hiap-1 and m-hiap-2 further demonstrate that homologs from different species may be isolated using the techniques provided herein and those generally known to artisans skilled in molecular biology.

III. Identification of Additional IAP Genes

Standard techniques, such as the polymerase chain reaction (PCR) and DNA hybridization, may be used to clone additional human IAP genes and their homologues in other species. Southern blots of human genomic DNA hybridized at low stringency with probes specific for xiap, hiap-1 and hiap-2 reveal bands that correspond to other known human IAP sequences as well as additional bands that do not correspond to known IAP sequences. Thus, additional IAP sequences may be readily identified using low stringency hybridization. Examples of murine and human xiap, hiap-1, and hiap-2 specific primers, which may be used to clone additional genes by RT-PCR, are shown in Table 5.

IV. Characterization of IAP Activity and Intracellular Localization Studies

The ability of putative IAPs to modulate apoptosis can be defined in in vitro systems in which alterations of apoptosis can be detected. Mammalian expression constructs carrying IAP cDNAs, which are either full-length or truncated, can be introduced into cell lines such as CHO, NIH 3T3, HL60, Rat-1, or Jurkat cells. In addition, Sf2l insect cells may be used, in which case the IAP gene is preferentially expressed using an insect heat shock promotor. Following transfection, apoptosis can be induced by standard methods, which include serum withdrawal, or application of staurosporine, menadione (which induces apoptosis via free radial formation), or anti-Fas antibodies. As a control, cells are cultured under the same conditions as those induced to undergo apoptosis, but either not transfected, or transfected with a vector that lacks an IAP insert. The ability of each IAP construct to inhibit apoptosis upon expression can be quantified by calculating the survival index of the cells, i.e., the ratio of surviving transfected cells to surviving control cells. These experiments can confirm the presence of apoptosis inhibiting activity and, as discussed below, can also be used to determine the functional region(s) of an IAP. These assays may also be performed in combination with the application of additional compounds in order to identify compounds that modulate apoptosis via IAP expression.

Figure 14A:
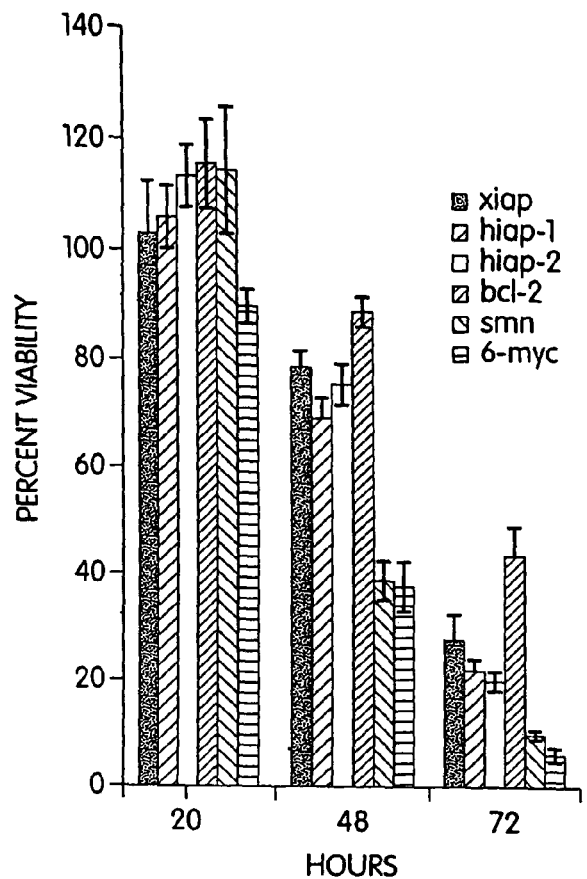
FIGS. 14A–14D are graphs depicting suppression of apoptosis by XIAP, HIAP-1, HIAP-2, Bcl-2, smn, and 6-myc.
Figure 14B:
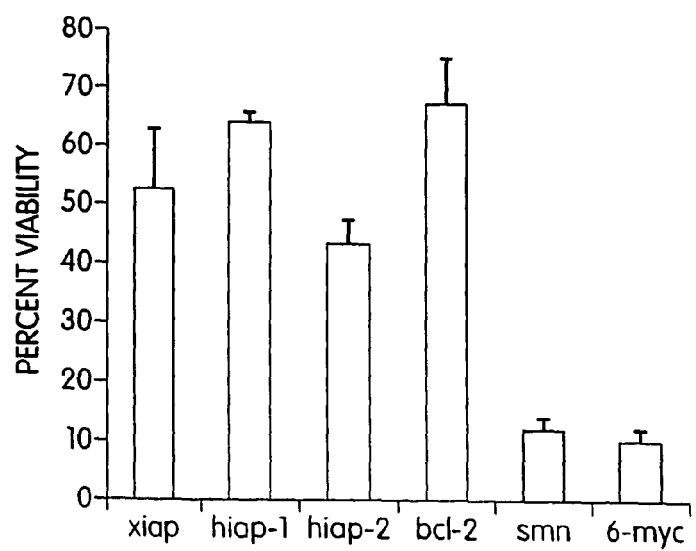

A. Cell Survival Following Transfection with Full-Length IAP Constructs and Induction of Apoptosis Specific examples of the results obtained by performing various apoptosis suppression assays are shown in FIGS. 14A to 14D. For example, CHO cell survival following transfection with one of six constructs and subsequent serum withdrawal is shown in FIG. 14A. The cells were transfected using Lipofectace™ with 2 µg of one of the following recombinant plasmids: pCDNA3-6myc-xiap (xiap), pCDNA3-6myc-hiap-1 (hiap-1), pCDNA3-6myc-hiap-2 (hiap-2), pCDNA3-bcl-2 (bcl-2), pCDNA3-HA-smn (smn), and pCDNA3-6myc (6-myc). Oligonucleotide primers were synthesized to allow PCR amplification and cloning of the xiap, hiap-1, and hiap-2 ORFs in pCDNA3 (Invitrogen). Each construct was modified to incorporate a synthetic myc tag encoding six repeats of the peptide sequence MEQKLI- SEEDL (SEQ ID NO: 43), thus allowing detection of myc-IAP fusion proteins via monoclonal anti-myc antiserum (Egan et al., Nature 363:45, 1993). Triplicate samples of cell lines in 24-well dishes were washed 5 times with serum free media and maintained in serum free conditions during the course of the experiment. Cells that excluded trypan blue, and that were therefore viable, were counted with a hemocytometer immediately, 24 hours, 48 hours, and 72 hours after serum withdrawal. Survival was calculated as a percentage of the initial number of viable cells. In this experiment, as well as those presented in FIGS. 14B and 14D, the percentage of viable cells shown represents the average of three separate experiments performed in triplicate, ± standard deviation.

The survival of CHO cells following transfection (with each one of the six constructs described above) and exposure to menadione is shown in FIG. 14B. The cells were plated in 24-well dishes, allowed to grow overnight, and then exposed to 20 μM menadione (Sigma Chemical Co., St. Louis, Mo.) for 1.5 hours. Triplicate samples were harvested at the time of exposure to menadione and 24 hours afterward, and survival was assessed by trypan blue exclusion.

Figure 14C:
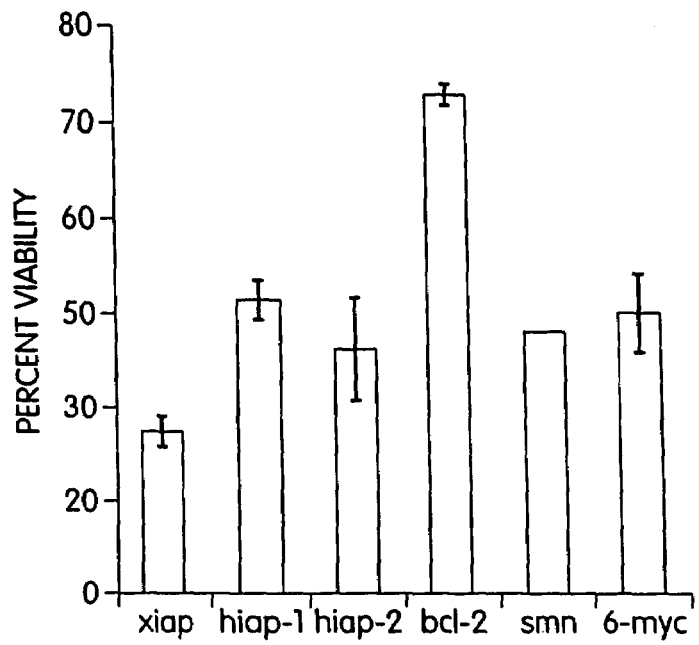
Figure 14D:
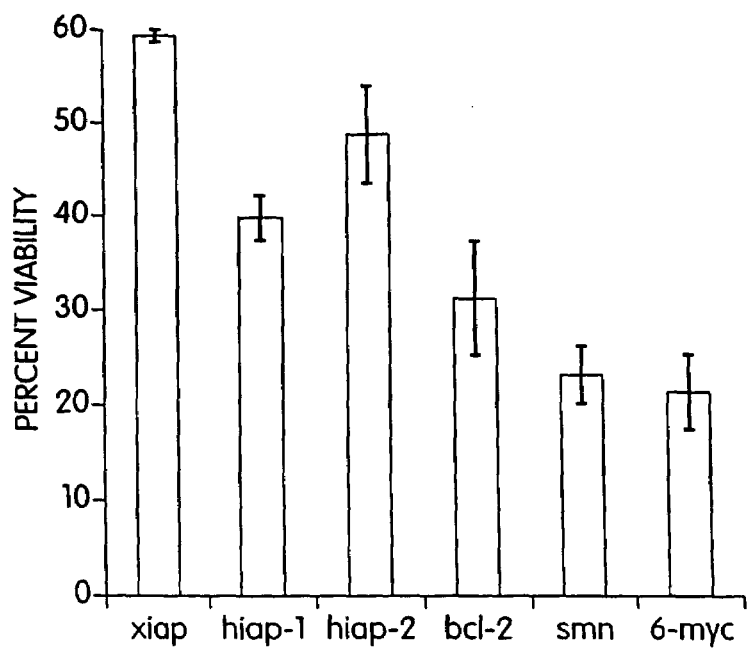

The survival of Rat-1 cells following transfection (with each one of the six constructs described above) and exposure to staurosporine is shown in FIG. 14C. Rat-1 cells were transfected and then selected in medium containing 800 μg/ml G418 for two weeks. The cell line was assessed for resistance to staurosporine-induced apoptosis (1 μM) for 5 hours. Viable cells were counted 24 hours after exposure to staurosporine by trypan blue exclusion. The percentage of viable cells shown represents the average of two experiments, ± standard deviation.

The Rat-1 cell line was also used to test the resistance of these cells to menadione (FIG. 14D) following transfection with each of the six constructs described above. The cells were exposed to 10 μM menadione for 1.5 hours, and the number of viable cells was counted 18 hours later.

B. Comparison of Cell Survival Following Transfection with Full-Length vs. Partial IAP Constructs In order to investigate the mechanism whereby human IAPs, including XIAP, HIAP-1, and HIAP-2, afford protection against cell death, expression vectors were constructed that contained either: (1) full-length IAP cDNA (as described above), (2) a portion of an IAP gene that encodes the BIR domains, but not the RZF, or (3) a portion of an IAP gene that encodes the RZF, but not the BIR domains. Human and murine xiap or m-xiap cDNAs were tested by transient or stable expression in HeLa, Jurkat, and CHO cell lines. Following transfection, apoptosis was induced by serum withdrawal, application of menadione, or application of an anti-Fas antibody. Cell death was then assessed, as described above, by trypan blue exclusion. As a control for transfection efficiency, the cells were co-transfected with a β-gal expression construct. Typically, approximately 20% of the cells were successfully transfected.

Figure 15B:
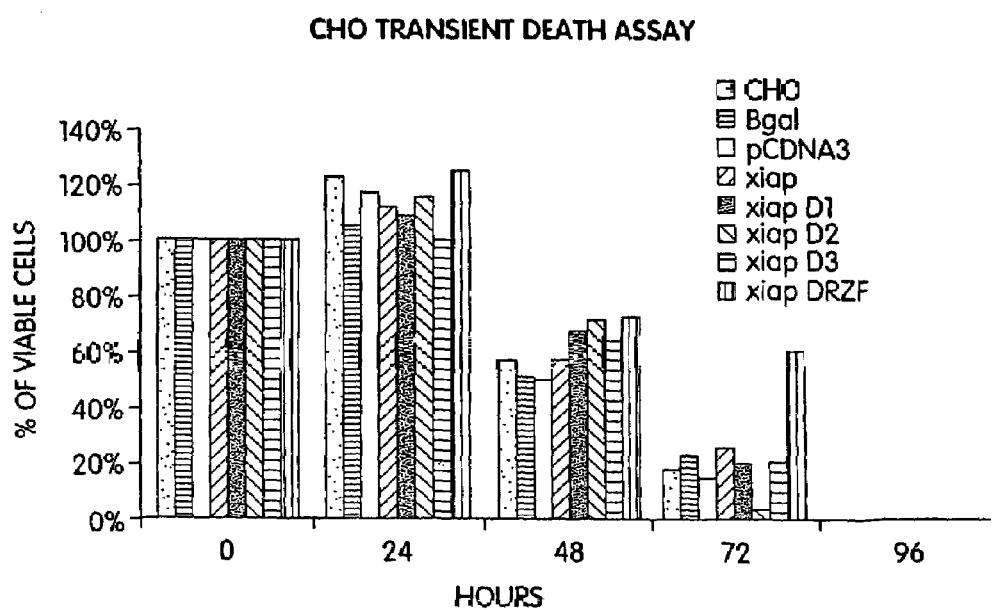

When CHO cells were transiently transfected, constructs containing full-length xiap or m-xiap cDNAs conferred modest protection against cell death (FIG. 15A). In contrast, the survival of CHO cells transfected with constructs encoding only the BIR domains (i.e., lacking the RZF domain; see FIG. 15A) was markedly enhanced 72 hours after serum deprivation. Furthermore, a large percentage of cells expressing the BIR domains were still viable after 96 hours, at which time no viable cells remained in the control, i.e. non-transfected, cell cultures (see "CHO" in FIG. 15A), and less than 5% of the cells transfected with the vector only, i.e., lacking a cDNA insert, remained viable (see "pcDNA3" in FIG. 15A). Deletion of any of the BIR domains results in the complete loss of apoptotic suppression, which is reflected by a decrease in the percentage of surviving CHO cells to control levels within 72 hours of serum withdrawal (FIG. 15B; see "xiapΔ1" (which encodes amino acids 89–497 of XIAP (SEQ ID NO.:4)), "xiapΔ2" (which encodes amino acids 246–497 of XIAP (SEQ ID NO.:4)), and "xiapΔ3" (which encodes amino acids 342–497 of XIAP (SEQ ID NO.:4)) at 72 hours).

Figure 16A:
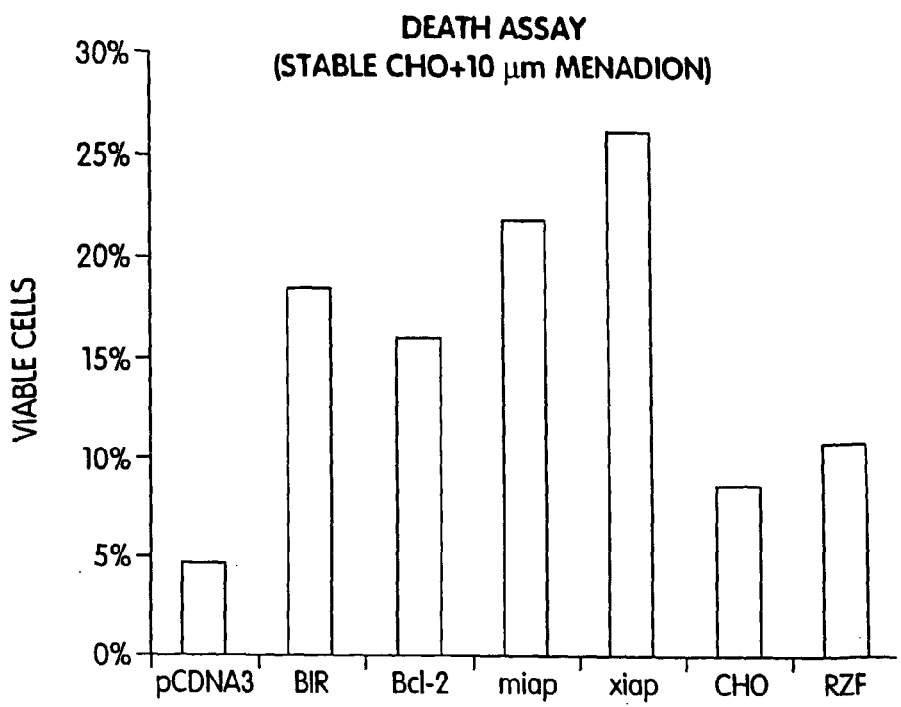
FIGS. 16A and 16B are bar graphs depicting the percentage of viable CHO cells following transient transfection with the cDNA constructs shown and subsequent exposure to menadione (FIG. 16A=10 μM menadione.
Figure 16B:
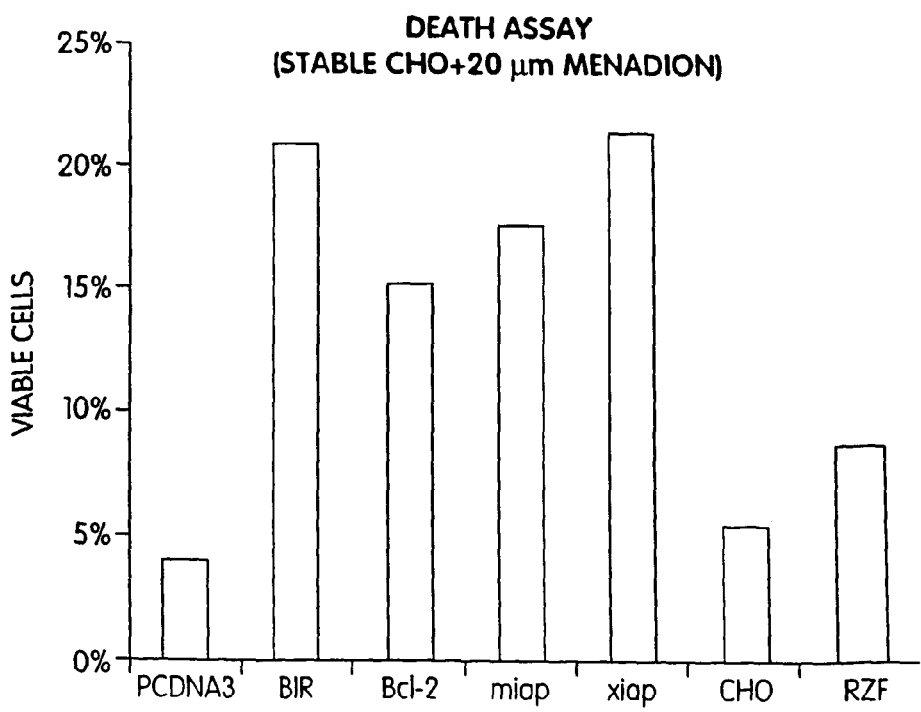

Stable pools of transfected CHO cells, which were maintained for several months under G418 selection, were induced to undergo apoptosis by exposure to 10 μM menadione for 2 hours. Among the CHO cells tested were those that were stably transfected with: (1) full-length m-xiap cDNA (miap), (2) full-length xiap cDNA (xiap), (3) full-length bcl-2 cDNA (Bcl-2), (4) cDNA encoding the three BIR domains (but not the RZF) of M-XIAP (BIR), and (5) cDNA encoding the RZF (but not BIR domains) of M-XIAP (RZF). Cells that were non-transfected (CHO) or transfected with the vector only (pcDNA3), served as controls for this experiment. Following exposure to 10 μM menadione, the transfected cells were washed with phosphate buffered saline (PBS) and cultured for an additional 24 hours in menadione-free medium. Cell death was assessed, as described above, by trypan blue exclusion. Less than 10% of the non-transfected or vector-only transfected cells remained viable at the end of the 24 hour survival period. Cells expressing the RZF did not fare significantly better. However, expression of full-length m-xiap, xiap, or bcl-2, and expression of the BIR domains, enhanced cell survival (FIG. 16A). When the concentration of menadione was increased from 10 μM to 20 μM (with all other conditions of the experiment being the same as when 10 μM menadione was applied), the percentage of viable CHO cells that expressed the BIR domain cDNA construct was higher than the percentage of viable cells that expressed either full-length m-xiap or bcl-2 (FIG. 16B).

C. Analysis of the Subcellular Location of Expressed RZF and BIR Domains

The assays of cell death described above indicate that the RZF may act as a negative regulator of the anti-apoptotic function of IAPs. One way in which the RZF, and possibly other IAP domains, may exert their regulatory influence is by altering the expression of genes, whose products function in the apoptotic pathway.

In order to determine whether the subcellular locations of expressed RZF and BIR domains are consistent with roles as nuclear regulatory factors, COS cells were transiently transfected with the following four constructs, and the expressed polypeptide was localized by immunofluorescence microscopy: (1) pcDNA3-6myc-xiap, which encodes all 497 amino acids of SEQ ID NO: 4, (2) pcDNA3-6myc-m-xiap, which encodes all 497 amino acids of mouse xiap (SEQ ID NO: 10), (3) pcDNA3-6myc-mxiap-BIR, which encodes amino acids 1 to 341 of m-xiap (SEQ ID NO: 10), and (4) pcDNA3-6myc-mxiap-RZF, which encodes amino acids 342–497 of m-xiap (SEQ ID NO: 10). The cells were grown on multi-well tissue culture slides for 12 hours, and then fixed and permeabilized with methanol. The constructs used (here and in the cell death assays) were tagged with a human Myc epitope tag at the N-terminus. Therefore, a monoclonal anti-Myc antibody and a secondary goat anti-mouse antibody, which was conjugated to FITC, could be used to localize the expressed products in transiently transfected COS cells. Full-length XIAP and MIAP were located in the cytoplasm, with accentuated expression in the peri-nuclear zone. The same pattern of localization was observed when the cells expressed a construct encoding the RZF domain (but not the BIR domains). However, cells expressing the BIR domains (without the RZF) exhibited, primarily, nuclear staining. The protein expressed by the BIR domain construct appeared to be in various stages of transfer to the nucleus.

These observations are consistent with the fact that, as described below, XIAP is cleaved within T cells that are treated with anti-Fas antibodies (which are potent inducers of apoptosis), and its N-terminal domain is translocated to the nucleus.

D. Examples of Additional Apoptosis Assays

Specific examples of apoptosis assays are also provided in the following references. Assays for apoptosis in lymphocytes are disclosed by: Li et al., Science 268:429, 1995; Gibellini et al., Br. J. Haematol. 89:24, 1995; Martin et al., J. Immunol. 152:330, 1994; Terai et al., J. Clin. Invest. 87:1710, 1991; Dhein et al., Nature 373:438, 1995; Katsikis et al., J. Exp. Med. 1815:2029, 1995; Westendorp et al., Nature 375:497, 1995; DeRossi et al., Virology 198:234, 1994.

Assays for apoptosis in fibroblasts are disclosed by: Vossbeck et al., Int. J. Cancer 61:92, 1995; Goruppi et al., Oncogene 9:1537, 1994; Fernandez et al., Oncogene 9:2009, 1994; Harrington et al., EMBO J., 13:3286, 1994; Itoh et al., J. Biol. Chem. 268:10932, 1993.

Assays for apoptosis in neuronal cells are disclosed by: Melino et al., Ann. Neurol. 36:864, 1994; Sato et al., J. Neurobiol. 25:1227, 1994; Ferrari et al., J. Neurosci. 1516:2857, 1995; Talley et al., Mol. Cell Biol. 1585:2359, 1995; Talley et al., Mol. Cell. Biol. 15:2359, 1995; Walkinshaw et al., J. Clin. Invest. 95:2458, 1995.

Assays for apoptosis in insect cells are disclosed by: Clem et al., Science 254:1388, 1991; Crook et al., J. Virol. 67:2168, 1993; Rabizadeh et al., J. Neurochem. 61:2318, 1993; Birnbaum et al., J. Virol. 68:2521, 1994; Clem et al., Mol. Cell. Biol. 14:5212, 1994.

V. Construction of a Transgenic Animal

Characterization of IAP genes provides information that is necessary for an IAP knockout animal model to be developed by homologous recombination. Preferably, the model is a mammalian animal, most preferably a mouse. Similarly, an animal model of IAP overproduction may be generated by integrating one or more IAP sequences into the genome, according to standard transgenic techniques.

A replacement-type targeting vector, which would be used to create a knockout model, can be constructed using an isogenic genomic clone, for example, from a mouse strain such as 129/Sv (Stratagene Inc., LaJolla, Calif.). The targeting vector is introduced into a suitably-derived line of embryonic stem (ES) cells by electroporation to generate ES cell lines that carry a profoundly truncated form of an IAP. To generate chimeric founder mice, the targeted cell lines are injected into a mouse blastula stage embryo. Heterozygous offspring are interbred to homozygosity. Knockout mice would provide the means, in vivo, to screen for therapeutic compounds that modulate apoptosis via an IAP-dependent pathway.

VI. IAP Protein Expression

IAP genes may be expressed in both prokaryotic and eukaryotic cell types. If an IAP modulates apoptosis by exacerbating it, it may be desirable to express that protein under control of an inducible promotor.

In general, IAPs according to the invention may be produced by transforming a suitable host cell with all or part of an IAP-encoding cDNA fragment that has been placed into a suitable expression vector.

Those skilled in the art of molecular biology will understand that a wide variety of expression systems may be used to produce the recombinant protein. The precise host cell used is not critical to the invention. The IAP protein may be produced in a prokaryotic host (e.g., *E. coli*) or in a eukaryotic host (e.g., *S. cerevisiae,* insect cells such as Sf21 cells, or mammalian cells such as COS-1, NIH 3T3, or HeLa cells). These cells are publicly available, for example, from the American Type Culture Collection (ATCC), Rockville, Md.; see also Ausubel et al., *Current Protocols in Molecular Biology,* John Wiley & Sons, New York, N.Y., 1994. The method of transduction and the choice of expression vehicle will depend on the host system selected. Transformation and transfection methods are described, e.g., in Ausubel et al. (supra), and expression vehicles may be chosen from those provided, e.g. in *Cloning Vectors: A Laboratory Manual* (P. H. Pouwels et al., 1985, Supp. 1987).

A preferred expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (Mol. Cell Biol. 5:3610, 1985).

Alternatively, an IAP may be produced by a stably-transfected mammalian cell line. A number of vectors suitable for stable transfection of mammalian cells are available to the public, (e.g., see Pouwels et al., supra), as are methods for constructing such cell lines (e.g., see Ausubel et al., supra). In one example, cDNA encoding an IAP is cloned into an expression vector that includes the dihydrofolate reductase (DHFR) gene. Integration of the plasmid and, therefore, integration of the IAP-encoding gene into the host cell chromosome is selected for by inclusion of 0.01–300 µM methotrexate in the cell culture medium (as described in Ausubel et al., supra). This dominant selection can be accomplished in most cell types. Recombinant protein expression can be increased by DHFR-mediated amplification of the transfected gene.

Methods for selecting cell lines bearing gene amplifications are described in Ausubel et al. (supra). These methods generally involve extended culture in medium containing gradually increasing levels of methotrexate. The most commonly used DHFR-containing expression vectors are pCVSEII-DHFR and pAdD26SV(A) (described in Ausubel et al., supra). The host cells described above or, preferably, a DHFR-deficient CHO cell line (e.g., CHO DHFR⁻ cells, ATCC Accession No. CRL 9096) are among those most preferred for DHFR selection of a stably-transfected cell line or DHFR-mediated gene amplification.

Once the recombinant protein is expressed, it is isolated by, for example, affinity chromatography. In one example, an anti-IAP antibody, which may be produced by the methods described herein, can be attached to a column and used to isolate the IAP protein. Lysis and fractionation of IAP-harboring cells prior to affinity chromatography may be performed by standard methods (see e.g., Ausubel et al., supra). Once isolated, the recombinant protein can, if desired, be purified further by e.g., by high performance liquid chromatography (HPLC; e.g., see Fisher, *Laboratory Techniques In Biochemistry And Molecular Biology,* Work and Burdon, Eds., Elsevier, 1980).

Polypeptides of the invention, particularly short IAP fragments, can also be produced by chemical synthesis (e.g., by the methods described in *Solid Phase Peptide Synthesis*, 2nd ed., 1984 The Pierce Chemical Co., Rockford, Ill.). These general techniques of polypeptide expression and purification can also be used to produce and isolate useful IAP fragments or analogs, as described herein.

VII. Anti-IAP Antibodies

In order to generate IAP-specific antibodies, an IAP coding sequence (i.e., amino acids 180–276) can be expressed as a C-terminal fusion with glutathione S-transferase (GST; Smith et al., Gene 67:31, 1988). The fusion protein can be purified on glutathione-Sepharose beads, eluted with glutathione, and cleaved with thrombin (at the engineered cleavage site), and purified to the degree required to successfully immunize rabbits. Primary immunizations can be carried out with Freund's complete adjuvant and subsequent immunizations performed with Freund's incomplete adjuvant. Antibody titres are monitored by western blot and immunoprecipitation analyses using the thrombin-cleaved IAP fragment of the GST-IAP fusion protein. Immune sera are affinity purified using CNBr-Sepharose-coupled IAP protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of IAP may be generated and coupled to keyhole limpet hemocyanin (KLH) through an introduced C-terminal lysine. Antiserum to each of these peptides is similarly affinity purified on peptides conjugated to BSA, and specificity is tested by ELISA and western blotting using peptide conjugates, and by western blotting and immunoprecipitation using IAP expressed as a GST fusion protein.

Alternatively, monoclonal antibodies may be prepared using the IAP proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, New York, N.Y., 1981; Ausubel et al., supra). Once produced, monoclonal antibodies are also tested for specific IAP recognition by western blot or immunoprecipitation analysis (by the methods described in Ausubel et al., supra).

Antibodies that specifically recognize IAPs or fragments of IAPs, such as those described herein containing one or more BIR domains (but not a ring zinc finger domain), or that contain a ring zinc finger domain (but not a BIR domain) are considered useful in the invention. They may, for example, be used in an immunoassay to monitor IAP expression levels or to determine the subcellular location of an IAP or IAP fragment produced by a mammal. Antibodies that inhibit the 26 kDa IAP cleavage product described herein (which contains at least one BIR domain) may be especially useful in inducing apoptosis in cells undergoing undesirable proliferation.

Preferably, antibodies of the invention are produced using IAP sequence that does not reside within highly conserved regions, and that appears likely to be antigenic, as analyzed by criteria such as those provided by the Peptide structure program (Genetics Computer Group Sequence Analysis Package, Program Manual for the GCG Package, Version 7, 1991) using the algorithm of Jameson and Wolf (CABIOS 4:181, 1988). Specifically, these regions, which are found between BIR1 and BIR2 of all IAPs, are: amino acid 99 to amino acid 170 of HIAP-1, amino acid 123 to amino acid 184 of HIAP-2, and amino acid 116 to amino acid 133 of either XIAP or M-XIAP. These fragments can be generated by standard techniques, e.g., by PCR, and cloned into the pGEX expression vector (Ausubel et al., supra). Fusion proteins are expressed in *E. coli* and purified using a glutathione agarose affinity matrix as described in Ausubel et al. (supra). In order to minimize the potential for obtaining antisera that is non-specific, or exhibits low-affinity binding to IAP, two or three fusions are generated for each protein, and each fusion is injected into at least two rabbits. Antisera are raised by injections in series, preferably including at least three booster injections.

VIII. Identification of Molecules that Modulate IAP Protein Expression

Isolation of IAP cDNAs also facilitates the identification of molecules that increase or decrease IAP expression. In one approach, candidate molecules are added, in varying concentration, to the culture medium of cells expressing IAP mRNA. IAP expression is then measured, for example, by northern blot analysis (Ausubel et al., supra) using an IAP cDNA, or cDNA fragment, as a hybridization probe (see also Table 5). The level of IAP expression in the presence of the candidate molecule is compared to the level of IAP expression in the absence of the candidate molecule, all other factors (e.g. cell type and culture conditions) being equal.

The effect of candidate molecules on IAP-mediated apoptosis may, instead, be measured at the level of translation by using the general approach described above with standard protein detection techniques, such as western blotting or immunoprecipitation with an IAP-specific antibody (for example, the IAP antibody described herein).

Compounds that modulate the level of IAP may be purified, or substantially purified, or may be one component of a mixture of compounds such as an extract or supernatant obtained from cells (Ausubel et al., supra). In an assay of a mixture of compounds, IAP expression is tested against progressively smaller subsets of the compound pool (e.g., produced by standard purification techniques such as HPLC or FPLC) until a single compound or minimal number of effective compounds is demonstrated to modulate IAP expression.

Compounds may also be screened for their ability to modulate IAP apoptosis inhibiting activity. In this approach, the degree of apoptosis in the presence of a candidate compound is compared to the degree of apoptosis in its absence, under equivalent conditions. Again, the screen may begin with a pool of candidate compounds, from which one or more useful modulator compounds are isolated in a step-wise fashion. Apoptosis activity may be measured by any standard assay, for example, those described herein.

Another method for detecting compounds that modulate the activity of IAPs is to screen for compounds that interact physically with a given IAP polypeptide. These compounds may be detected by adapting interaction trap expression systems known in the art. These systems detect protein interactions using a transcriptional activation assay and are generally described by Gyuris et al. (Cell 75:791, 1993) and Field et al. (Nature 340:245, 1989), and are commercially available from Clontech (Palo Alto, Calif.). In addition, PCT Publication WO 95/28497 describes an interaction trap assay in which proteins involved in apoptosis, by virtue of their interaction with Bcl-2, are detected. A similar method may be used to identify proteins and other compounds that interact with IAPs.

Compounds or molecules that function as modulators of IAP-mediated cell death may include peptide and nonpeptide molecules such as those present in cell extracts, mammalian serum, or growth medium in which mammalian cells have been cultured.

A molecule that promotes an increase in IAP expression or IAP activity is considered particularly useful in the invention; such a molecule may be used, for example, as a therapeutic to increase cellular levels of IAP and thereby exploit the ability of IAP polypeptides to inhibit apoptosis.

A molecule that decreases IAP activity (e.g., by decreasing IAP gene expression or polypeptide activity) may be used to decrease cellular proliferation. This would be advantageous in the treatment of neoplasms (see Table 3, below), or other cell proliferative diseases.

TABLE 3

NORTHERN BLOT IAP RNA LEVELS IN CANCER CELLS*

|  | xiap | hiap1 | hiap2 |
|---|---|---|---|
| Promyelocytic Leukemia HL-60 | + | + | + |
| Hela S-3 | + | + | + |
| Chronic Myelogenous Leukemia K-562 | +++ | + | +++ |
| Lymphoblastic Leukemia MOLT-4 | +++ | + | + |
| Burkitt's Lymphoma Raji | + | +(×10) | + |
| Colorectal Adenocarcinoma SW-480 | +++ | +++ | +++ |
| Lung Carcinoma A-549 | + | + | + |
| Melanoma G-361 | +++ | + | + |

*Levels are indicated by a (+) and are the approximate increase in RNA levels relative to northern blots of RNA from non-cancerous control cell lines. A single plus indicates an estimated increase of at least 1-fold Molecules that are found, by the methods described above, to effectively modulate IAP gene expression or polypeptide activity may be tested further in animal models. If they continue to function successfully in an in vivo setting, they may be used as therapeutics to either inhibit or enhance apoptosis, as appropriate.

IX. IAP Therapy

The level of IAP gene expression correlates with the level of apoptosis. Thus, IAP genes also find use in anti-apoptosis gene therapy. In particular, a functional IAP gene may be used to sustain neuronal cells that undergo apoptosis in the course of a neurodegenerative disease, lymphocytes (i.e., T cells and B cells), or cells that have been injured by ischemia.

Retroviral vectors, adenoviral vectors, adeno-associated viral vectors, or other viral vectors with the appropriate tropism for cells likely to be involved in apoptosis (for example, epithelial cells) may be used as a gene transfer delivery system for a therapeutic IAP gene construct. Numerous vectors useful for this purpose are generally known (Miller, Human Gene Therapy 15, 1990; Friedman, Science 244:1275, 1989; Eglitis and Anderson, Biotechniques 6:608, 1988; Tolstoshev and Anderson, Curr. Opin. Biotechnol. 1:55, 1990; Sharp, Lancet 337:1277, 1991; Cornetta et al., Nucleic Acid Research and Molecular Biology 36:311, 1987; Anderson, Science 226:401, 1984; Moen, Blood Cells 17:407, 1991; Miller et al., Biotechniques 7:980, 1989; La Salle et al., Science 259:988, 1993; Johnson, Chest 107:77S, 1995). Retroviral vectors are particularly well developed and have been used in clinical settings (Rosenberg et al., N. Engl. J. Med. 323:370, 1990; Anderson et al., U.S. Pat. No. 5,399,346). Non-viral approaches may also be employed for the introduction of therapeutic DNA into cells otherwise predicted to undergo apoptosis. For example, IAP may be introduced into a neuron or a T cell by lipofection (Felgner et al., Proc. Natl. Acad. Sci. USA 84:7413, 1987; Ono et al., Neurosci. Lett. 117:259, 1990; Brigham et al., Am. J. Med. Sci. 298:278, 1989; Staubinger et al., Meth. Enzymol. 101:512, 1983), asialorosonucoid-polylysine conjugation (Wu et al., J. Biol. Chem. 263:14621, 1988; Wu et al., J. Biol. Chem. 264: 16985, 1989); or, less preferably, microinjection under surgical conditions (Wolff et al., Science 247:1465, 1990).

For any of the methods of application described above, the therapeutic IAP DNA construct is preferably applied to the site of the predicted apoptosis event (for example, by injection). However, it may also be applied to tissue in the vicinity of the predicted apoptosis event or to a blood vessel supplying the cells predicted to undergo apoptosis.

In the constructs described, IAP cDNA expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in neural cells, T cells, or B cells may be used to direct IAP expression. The enhancers used could include, without limitation, those that are characterized as tissue- or cell-specific in their expression. Alternatively, if an IAP genomic clone is used as a therapeutic construct (for example, following its isolation by hybridization with the IAP cDNA described above), regulation may be mediated by the cognate regulatory sequences or, if desired, by regulatory sequences derived from a heterologous source, including any of the promoters or regulatory elements described above.

Less preferably, IAP gene therapy is accomplished by direct administration of the IAP mRNA or antisense IAP mRNA to a cell that is expected to undergo apoptosis. The mRNA may be produced and isolated by any standard technique, but is most readily produced by in vitro transcription using an IAP cDNA under the control of a high efficiency promoter (e.g., the T7 promoter). Administration of IAP mRNA to malignant cells can be carried out by any of the methods for direct nucleic acid administration described above.

Ideally, the production of IAP protein by any gene therapy approach will result in cellular levels of IAP that are at least equivalent to the normal, cellular level of IAP in an unaffected cell. Treatment by any IAP-mediated gene therapy approach may be combined with more traditional therapies.

Another therapeutic approach within the invention involves administration of recombinant IAP protein, either directly to the site of a predicted apoptosis event (for example, by injection) or systemically (for example, by any conventional recombinant protein administration technique). The dosage of IAP depends on a number of factors, including the size and health of the individual patient, but, generally, between 0.1 mg and 100 mg inclusive are administered per day to an adult in any pharmaceutically acceptable formulation.

X. Administration of IAP Polypeptides, IAP Genes, or Modulators of IAP Synthesis or Function An IAP protein, gene, or modulator may be administered within a pharmaceutically-acceptable diluent, carrier, or excipient, in unit dosage form. Conventional pharmaceutical practice may be employed to provide suitable formulations or compositions to administer IAP to patients suffering from a disease that is caused by excessive apoptosis. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for IAP modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with an IAP protein, gene, or modulatory compound may be combined with more traditional therapies for the disease such as surgery, steroid therapy, or chemotherapy for autoimmune disease; antiviral therapy for AIDS; and tissue plasminogen activator (TPA) for ischemic injury.

XI. Detection of Conditions Involving Altered Apoptosis

IAP polypeptides and nucleic acid sequences find diagnostic use in the detection or monitoring of conditions involving aberrant levels of apoptosis. For example, decrease expression of IAP may be correlated with enhanced apoptosis in humans (see section XII, below). Accordingly, a decrease or increase in the level of IAP production may provide an indication of a deleterious condition. Levels of IAP expression may be assayed by any standard technique. For example, IAP expression in a biological sample (e.g., a biopsy) may be monitored by standard northern blot analysis or may be aided by PCR (see, e.g., Ausubel et al., supra; *PCR Technology: Principles and Applications for DNA Amplification,* H. A. Ehrlich, Ed. Stockton Press, NY; Yap et al. Nucl. Acids. Res. 19:4294, 1991).

Alternatively, a biological sample obtained from a patient may be analyzed for one or more mutations in the IAP sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant IAP detection, and each is well known in the art; examples of particular techniques are described, without limitation, in Orita et al., Proc. Natl. Acad. Sci. USA 86:2766, 1989; Sheffield et al., Proc. Natl. Acad. Sci. USA 86:232, 1989).

In yet another approach, immunoassays are used to detect or monitor IAP protein in a biological sample. IAP-specific polyclonal or monoclonal antibodies (produced as described above) may be used in any standard immunoassay format (e.g., ELISA, western blot, or RIA) to measure IAP polypeptide levels. These levels would be compared to wild-type IAP levels, with a decrease in IAP production indicating a condition involving increased apoptosis. Examples of immunoassays are described, e.g., in Ausubel et al., supra. Immunohistochemical techniques may also be utilized for IAP detection. For example, a tissue sample may be obtained from a patient, sectioned, and stained for the presence of IAP using an anti-IAP antibody and any standard detection system (e.g., one which includes a secondary antibody conjugated to horseradish peroxidase). General guidance regarding such techniques can be found in, e.g., Bancroft and Stevens (*Theory and Practice of Histological Techniques,* Churchill Livingstone, 1982) and Ausubel et al. (supra).

In one preferred example, a combined diagnostic method may be employed that begins with an evaluation of IAP protein production (for example, by immunological techniques or the protein truncation test (Hogerrorst et al., Nat. Gen. 10:208, 1995)) and also includes a nucleic acid-based detection technique designed to identify more subtle IAP mutations (for example, point mutations). As described above, a number of mismatch detection assays are available to those skilled in the art, and any preferred technique may be used. Mutations in IAP may be detected that either result in loss of IAP expression or loss of IAP biological activity. In a variation of this combined diagnostic method, IAP biological activity is measured as protease activity using any appropriate protease assay system (for example, those described above).

Mismatch detection assays also provide an opportunity to diagnose an IAP-mediated predisposition to diseases caused by inappropriate apoptosis. For example, a patient heterozygous for an IAP mutation may show no clinical symptoms and yet possess a higher than normal probability of developing one or more types of neurodegenerative, myelodysplastic or ischemic diseases. Given this diagnosis, a patient may take precautions to minimize their exposure to adverse environmental factors (for example, UV exposure or chemical mutagens) and to carefully monitor their medical condition (for example, through frequent physical examinations). This type of IAP diagnostic approach may also be used to detect IAP mutations in prenatal screens. The IAP diagnostic assays described above may be carried out using any biological sample (for example, any biopsy sample or bodily fluid or tissue) in which IAP is normally expressed. Identification of a mutant IAP gene may also be assayed using these sources for test samples.

Alternatively, an IAP mutation, particularly as part of a diagnosis for predisposition to IAP-associated degenerative disease, may be tested using a DNA sample from any cell, for example, by mismatch detection techniques. Preferably, the DNA sample is subjected to PCR amplification prior to analysis.

In order to demonstrate the utility of IAP gene sequences as diagnostics and prognostics for cancer, a Human Cancer Cell Line Multiple Tissue Northern Blot (Clontech, Palo Alto, Calif.; #7757-1) was probed. This northern blot contained approximately 2 µg of poly $A^+$ RNA per lane from eight different human cell lines: (1) promyelocytic leukemia HL-60, (2) HeLa cell S3, (3) chronic myelogenous leukemia K-562, (4) lymphoblastic leukemia MOLT-4, (5) Burkitt's lymphoma Raji, (6) colorectal adenocarcinoma SW480, (7) lung carcinoma A549, and (8) melanoma G361. As a control, a Human Multiple Tissue Northern Blot (Clontech, Palo Alto, Calif.; #7759-1) was probed. This northern blot contained approximately 2 µg of poly $A^+$ RNA from eight different human tissues: (1) spleen, (2) thymus, (3) prostate, (4) testis, (5) ovary, (6) small intestine, (7) colon, and (8) peripheral blood leukocytes.

The northern blots were hybridized sequentially with: (1) a 1.6 kb probe to the xiap coding region, (2) a 375 bp hiap-2 specific probe corresponding to the 3' untranslated region, (3) a 1.3 kb probe to the coding region of hiap-1, which cross-reacts with hiap-2, (4) a 1.0 kb probe derived from the coding region of bcl-2, and (5) a probe to β-actin, which was provided by the manufacturer. Hybridization was carried out at 50° C. overnight, according to the manufacturer's suggestion. The blot was washed twice with 2×SSC, 0.1% SDS at room temperature for 15 minutes and then with 2×SSC, 0.1% SDS at 50° C.

All cancer lines tested showed increased IAP expression relative to samples from non-cancerous control tissues (Table 3). Expression of xiap was particularly high in HeLa (S-3), chronic myelogenous leukemia (K-562), colorectal adenocarcinoma (SW-480), and melanoma (G-361) lines. Expression of hiap-1 was extremely high in Burkitt's lymphoma, and was also elevated in colorectal adenocarcinoma. Expression of hiap-2 was particularly high in chronic myelogenous leukemia (K-562) and colorectal adenocarcinoma (SW-480). Expression of bcl-2 was upregulated only in HL-60 leukemia cells.

These observations suggest that upregulation of the antiapoptotic IAP genes may be a widespread phenomenon, perhaps occurring much more frequently than upregulation of bcl-2. Furthermore, upregulation may be necessary for the establishment or maintenance of the transformed state of cancerous cells.

Figure 17:
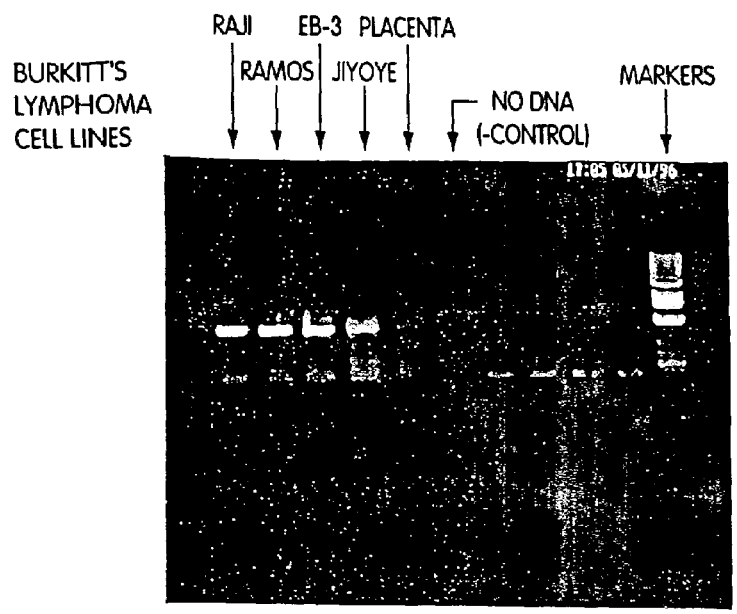
FIG. 17 is a photograph of an agarose gel containing cDNA fragments that were amplified, with hiap-1-specific primers, from RNA obtained from Raji, Ramos, EB-3, and Jiyoye cells, and from normal placenta.

In order to pursue the observation described above, i.e., that hiap-1 is overexpressed in the Raji Burkitt's lymphoma cell line, RT-PCR analysis was performed in multiple Burkitt's lymphoma cell lines. Total RNA was extracted from cells of the Raji, Ramos, EB-3, and Jiyoye cell lines, and as a positive control, from normal placental tissue. The RNA was reverse transcribed, and amplified by PCR with the following set of oligonucleotide primers: 5'-AGT-GCGGGTTTTTATTATGTG-3' (SEQ ID NO: 44) and 5'-AGATGACCACAAGGAATAAACACTA-3' (SEQ ID NO: 45), which selectively amplify a hiap-1 cDNA fragment. RT-PCR was conducted using a Perkin Elmer 480 Thermocycler to carry out 35 cycles of the following program: 94° C. for 1 minute, 50° C. for 1.5 minutes, and 72° C. for a minute. The PCR reaction product was electrophoresed on an agarose gel and stained with ethidium bromide. Amplified cDNA fragments of the appropriate size were clearly visible in all lanes containing Burkitt's lymphoma samples, but absent in the lanes containing the normal placental tissue sample, and absent in lanes containing negative control samples, where template DNA was omitted from the reaction (FIG. 17).

XII. Accumulation of a 26 kDa Cleavage Protein in Astrocytoma Cells

A. Identification of a 26 kDa Cleavage Protein

Figure 18:
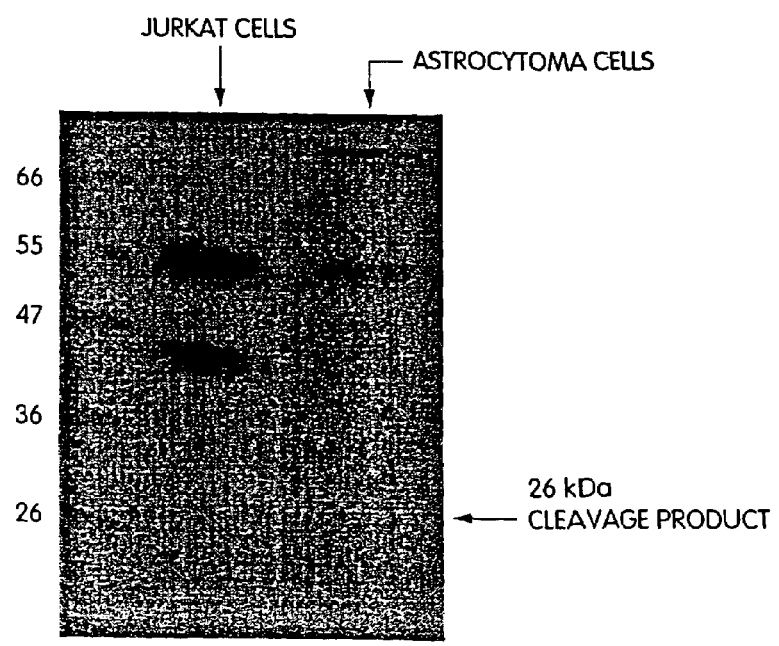
FIG. 18 is a photograph of a western blot containing protein extracted from Jurkat and astrocytoma cells stained with an anti-XIAP antibody. The position and size of a series of marker proteins is indicated.

A total protein extract was prepared from Jurkat and astrocytoma cells by sonicating them (X3 for 15 seconds at 4° C.) in 50 mM Tris-HCl (pH 8.0), 150 mM NaCl, 1 mM PMSF, 1 μg/ml aprotinin, and 5 mM benzamidine. Following sonication, the samples were centrifuged (14,000 RPM in a microfuge) for five minutes. Twenty tg of protein was loaded per well on a 10% SDS-polyacrylamide gel, electrophoresed, and electroblotted by standard methods to PVDF membranes. Western blot analysis, performed as described previously, revealed that the astrocytoma cell line (CCF-STTG1) abundantly expressed an anti-xiap reactive band of approximately 26 kDa, despite the lack of an apoptotic trigger event (FIG. 18). In fact, this cell line has been previously characterized as being particularly resistant to standard apoptotic triggers.

Figure 19:
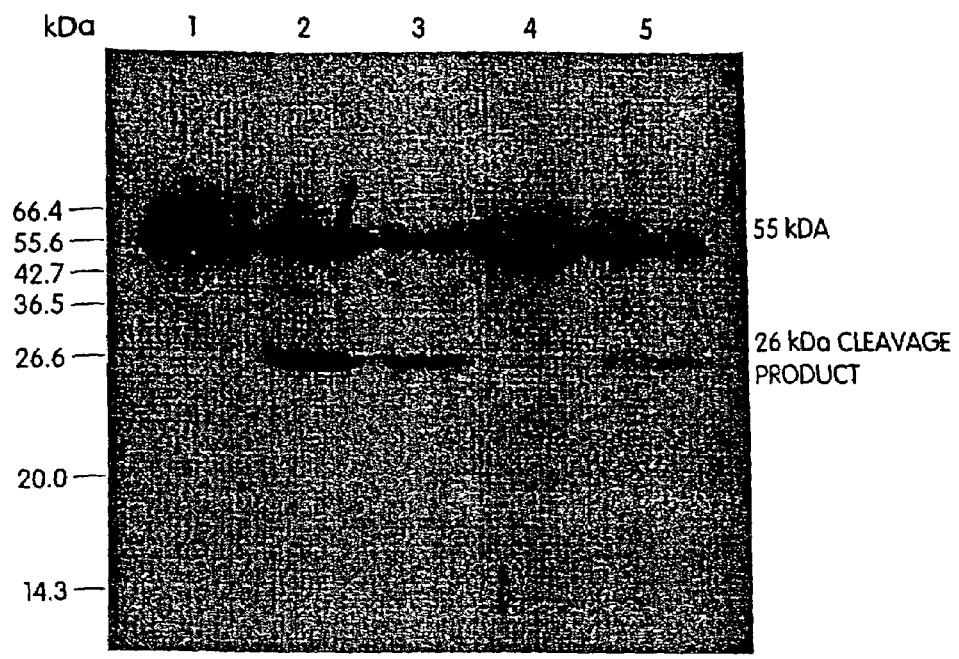
FIG. 19 is a photograph of a western blot containing protein extracted from Jurkat cells following treatment as described in Example XII. The blot was stained with a rabbit polyclonal anti-XIAP antibody. Lane 1, negative control; lane 2, anti-Fas antibody; lane 3, anti-Fas antibody and cycloheximide; lane 4, TNF-α; lane 5, TNF-α and cycloheximide.

A 26 kDa XIAP-reactive band was also observed under the following experimental conditions. Jurkat cells (a transformed human T cell line) were induced to undergo apoptosis by exposure to an anti-Fas antibody (1 μg/ml). Identical cultures of Jurkat cells were exposed either to: (1) anti-Fas antibody and cycloheximide (20 μg/ml), (2) tumor necrosis factor alpha (TNF-α, at 1,000 U/ml), or (3) TNF-α and cycloheximide (20 μg/ml). All cells were harvested 6 hours after treatment began. In addition, as a negative control, anti-Fas antibody was added to an extract after the cells were harvested. The cells were harvested in SDS sample buffer, electrophoresed on a 12.5% SDS polyacrylamide gel, and electroblotted onto PVDF membranes using standard methods. The membranes were immunostained with a rabbit polyclonal anti-XIAP antibody at 1:1000 for 1 hour at room temperature. Following four 15 minute washes, a goat anti-rabbit antibody conjugated to horse-radish peroxidase was applied at room temperature for 1 hour. Unbound secondary antibody was washed away, and chemiluminescent detection of XIAP protein was performed. The western blot revealed the presence of the full-length, 55 kDa XIAP protein, both in untreated and treated cells. In addition, a novel, approximately 26 kDa XIAP-reactive band was also observed in apoptotic cell extracts, but not in the control, untreated cell extracts (FIG. 19).

Figure 20:
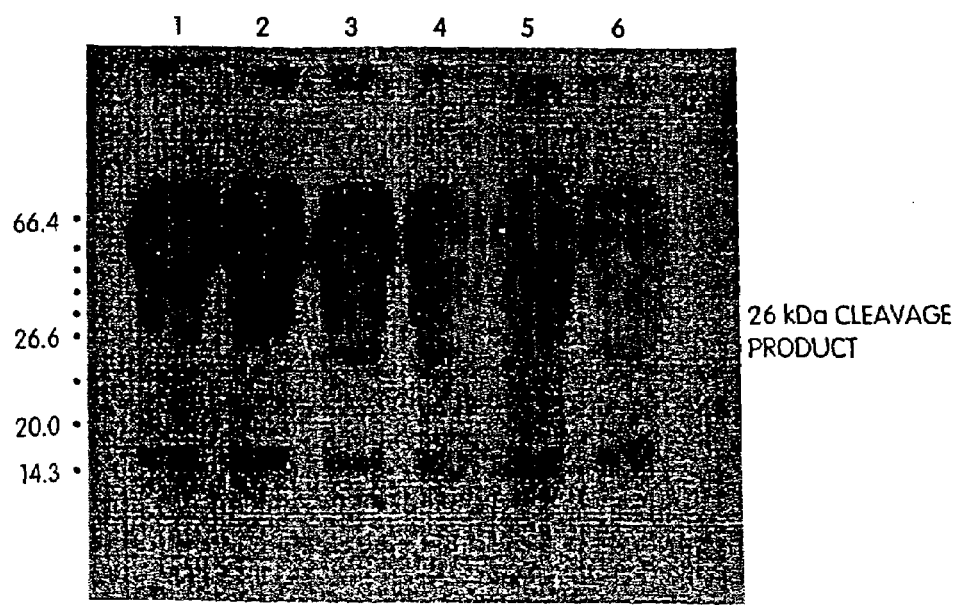
FIG. 20 is a photograph of a western blot containing protein extracted from HeLa cells following exposure to anti-Fas antibodies. The blot was stained with a rabbit polyclonal anti-XIAP antibody. Lane 1, negative control; lane 2, cycloheximide; lane 3, anti-Fas antibody; lane 4, anti-Fas antibody and cycloheximide; lane 5, TNF-α; lane 6, TNF-α and cycloheximide.

Cleavage of XIAP occurs in a variety of cell types, including other cancer cell lines such as HeLa. The expression of the 26 kDa XIAP cleavage product was demonstrated in HeLa cells as follows. HeLa cells were treated with either: (1) cyclohexamide (20 μg/ml), (2) anti-Fas antibody (1 μg/ml), (3) anti-Fas antibody (1 μg/ml) and cyclohexamide (20 μg/ml), (4) TNFα (1,000 U/ml), or (5) TNFα (1,000 U/ml) and cyclohexamide (20 μg/ml). All cells were harvested 18 hours after treatment began. As above, anti-Fas antibody was added to an extract after the cells were harvested. HeLa cells were harvested, and the western blot was probed under the same conditions as used to visualize xiap-reactive bands from Jurkat cell samples. A 26 kDa XIAP band was again seen in the apoptotic cell preparations (FIG. 20). Furthermore, the degree of XIAP cleavage correlated positively with the extent of apoptosis. Treatment of HeLa cells with cycloheximide or TNFα alone caused only minor apoptosis, and little cleavage product was observed. If the cells were treated with the anti-Fas antibody, a greater amount of cleavage product was apparent. These data indicate that XIAP is cleaved in more than one cell type and in response to more than one type of apoptotic trigger.

B. Time Course of Expression

Figure 21A:
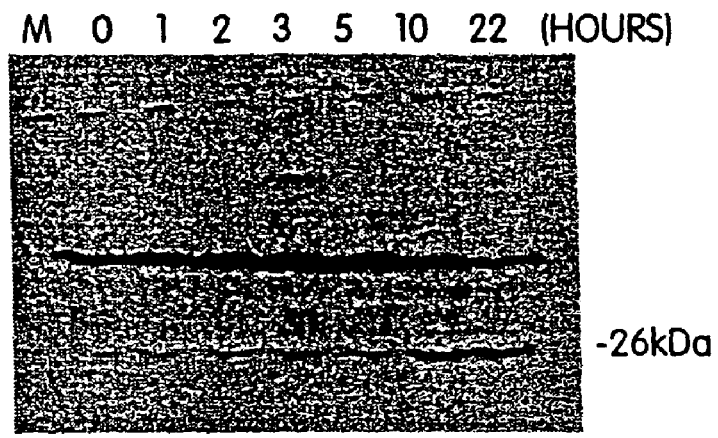
FIGS. 21A and 21B are photographs of western blots stained with rabbit polyclonal anti-XIAP antibody. Protein was extracted from HeLa cells (FIG. 21A) and Jurkat cells (FIG. 21B) immediately, 1, 2, 3, 5, 10, and 22 hours after exposure to anti-Fas antibody.
Figure 21B:
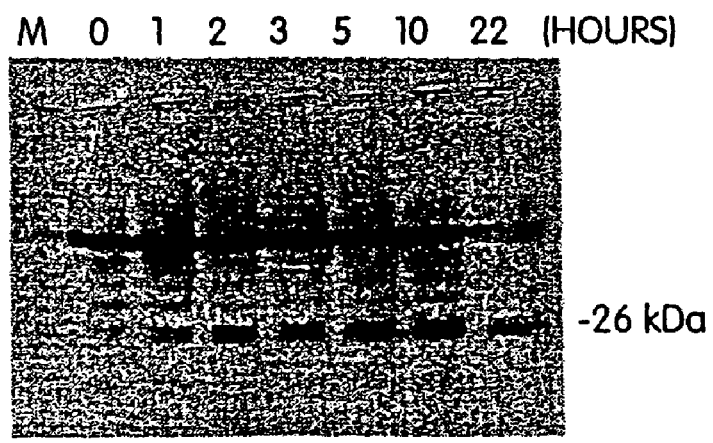

The time course over which the 26 kDa cleavage product accumulates was examined by treating HeLa and Jurkat cells with anti-Fas antibody (1 μg/ml) and harvesting them either immediately, or 1, 2, 3, 5, 10, or 22 hours after treatment. Protein extracts were prepared and western blot analysis was performed as described above. Both types of cells accumulated increasing quantities of the 26 kDa cleavage product over the time course examined (FIGS. 21A and 21B).

C. Subcellular Localization of the 26 kDa XIAP Cleavage Product

Figure 22A:
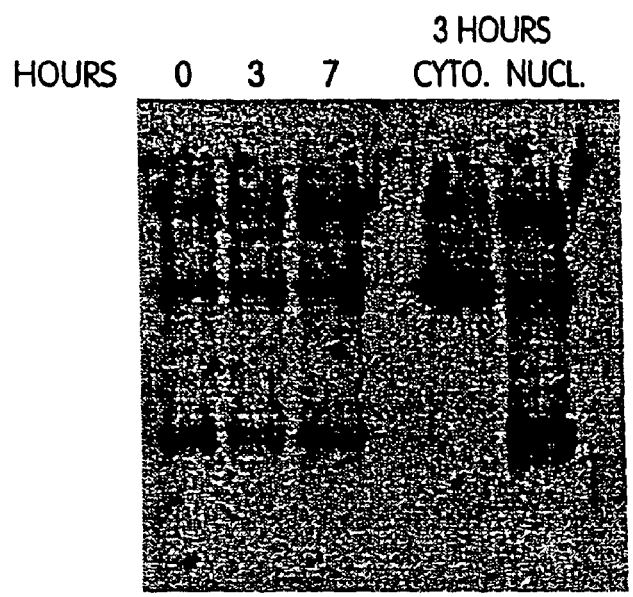
FIGS. 22A and 22B are photographs of western blots stained with an anti-CPP32 antibody (FIG. 22A) or a rabbit polyclonal anti-XIAP antibody (FIG. 22B). Protein was extracted from Jurkat cells immediately, 3 hours, or 7 hours after exposure to an anti-Fas antibody. In addition to total protein, cytoplasmic and nuclear extracts are shown.
Figure 22B:
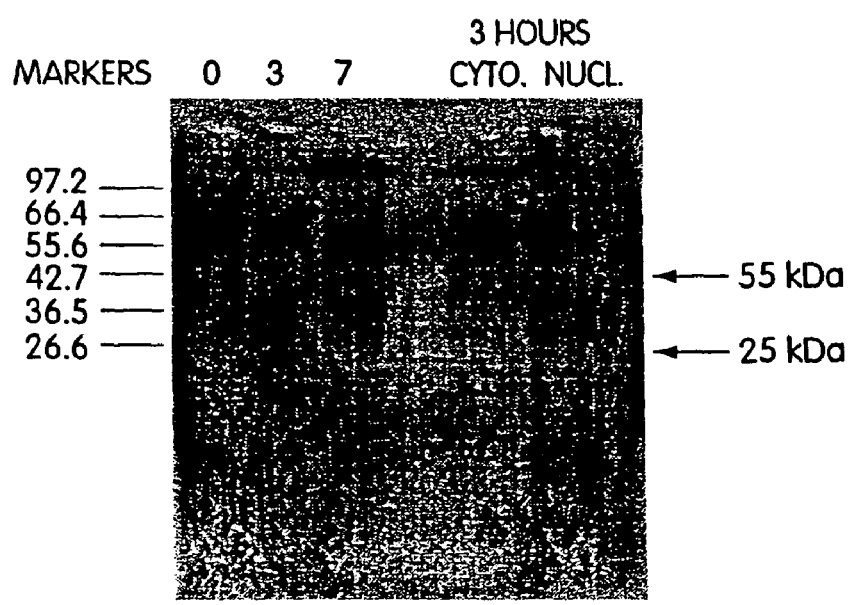

In order to determine the subcellular location of the 26 kDa cleavage product, Jurkat cells were induced to undergo apoptosis by exposure to anti-Fas antibody (1 μg/ml) and were then harvested either immediately, 3 hours, or 7 hours later. Total protein extracts were prepared, as described above, from cells harvested at each time point. In order to prepare nuclear and cytoplasmic cell extracts, apoptotic Jurkat cells were washed with isotonic Tris buffered saline (pH 7.0) and lysed by freezing and thawing five times in cell extraction buffer (50 mM PIPES, 50 mM KCl, 5 mM EGTA, 2 mM $MgCl_2$, 1 mM DTT, and 20 μM cytochalasin B). Nuclei were pelleted by centrifugation and resuspended in isotonic Tris (pH 7.0) and frozen at −80° C. The cytoplasmic fraction of the extract was processed further by centrifugation at 60,000 RPM in a TA 100.3 rotor for 30 minutes. Supernatants were removed and frozen at −80° C. Samples of both nuclear and cytoplasmic fractions were loaded on a 12.5% SDS-polyacrylamide gel, and electroblotted onto PVDF membranes. Western blot analysis was then performed using either an anti-CPP32 antibody (Transduction Laboratories Lexington, Ky.; FIG. 22A) or the rabbit anti-XIAP antibody described above (FIG. 22B).

The anti-CPP32 antibody, which recognizes the CPP32 protease (also known as YAMA or apopain) partitioned almost exclusively in the cytoplasmic fraction. The 55 kDa XIAP protein localized exclusively in the cytoplasm of apoptotic cells, in agreement with the studies presented above, where XIAP protein in normal, healthy COS cells was seen to localize, by immunofluoresence microscopy, to the cytoplasm. In contrast, the 26 kDa cleavage product localized exclusively to the nuclear fraction of apoptotic Jurkat cells. Taken together, these observations suggest that the anti-apoptotic component of XIAP could be the 26 kDa cleavage product, which exerts its influence within the nucleus.

D. In vitro Cleavage of XIAP Protein and Characterization of the Cleavage Product For this series of experiments, XIAP protein was labeled with $^{35}S$ using the plasmid pcDNA3-6myc-xiap, T7 RNA polymerase, and a coupled transcription/ translation kit (Promega) according to the manufacturer's instructions. Radioactively labeled XIAP protein was separated from unincorporated methionine by column chromatography using Sephadex G-50™. In addition, extracts of apoptotic Jurkat cells were prepared following treatment with anti-Fas antibody (1 μg/ml) for three hours. To prepare the extracts, the cells were lysed in Triton X-100 buffer (1% Triton X-100, 25 mM Tris HCl) on ice for two hours and then microcentrifuged for 5 minutes. The soluble extract was retained (and was labelled "TX100"). Cells were lysed in cell extraction buffer with freeze/thawing. The soluble cytoplasmic fraction was set aside (and labelled "CEB"). Nuclear pellets from the preparation of the CEB cytoplasmic fraction were solubilized with Triton X-100 buffer, microcentrifuged, and the soluble fractions, which contains primarily nuclear DNA, was retained (and labelled "CEB-TX100"). Soluble cell extract was prepared by lysing cells with NP-40 buffer, followed by microcentrifugation for 5 minutes (and was labeled NP-40). In vitro cleavage was performed by incubating 16 μl of each extract (CEB, TX-100, CEB-TX 100, and NP-40) with 4 μl of in vitro translated XIAP protein at 37° C. for 7 hours. Negative controls, containing only TX100 buffer or CEB buffer were also included. The proteins were separated on a 10% SDS-polyacrylamide gel, which was then dried and exposed to X-ray film overnight.

Figure 23:
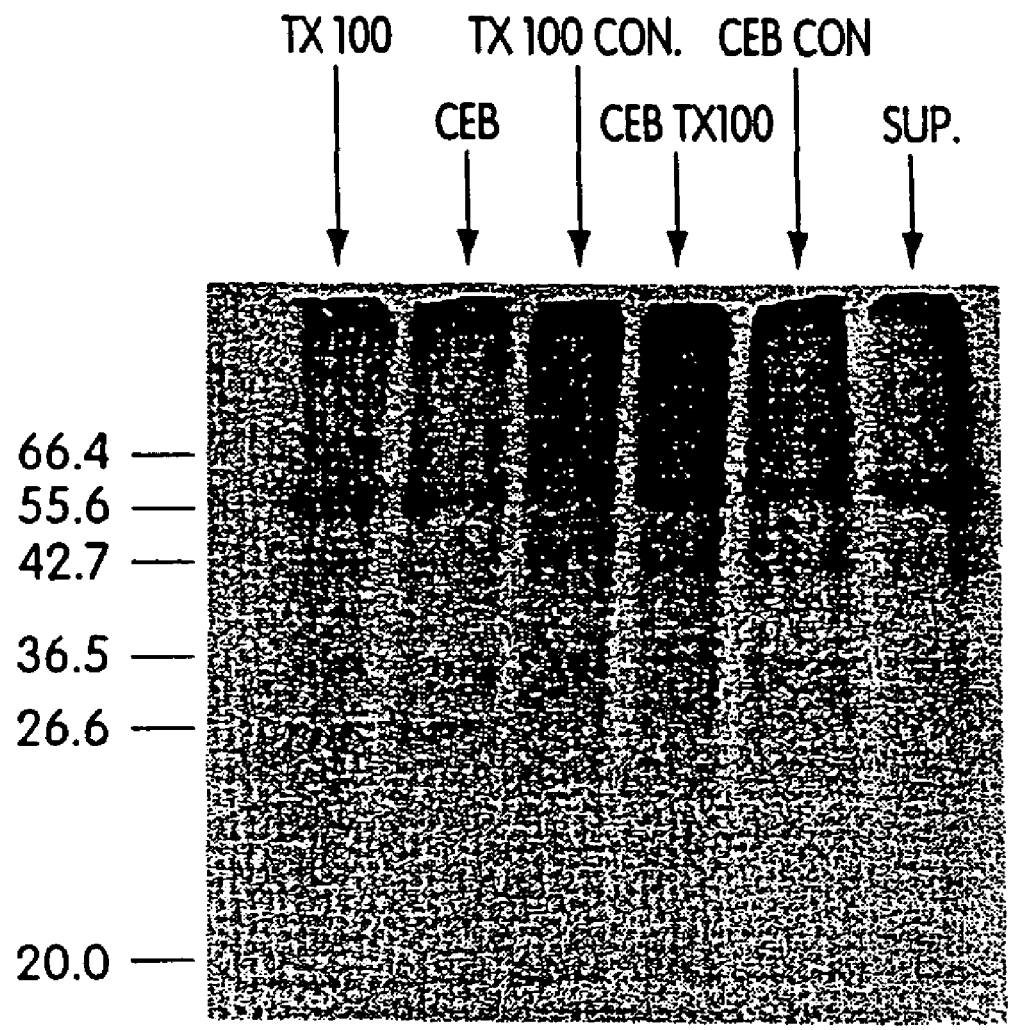
FIG. 23 is a photograph of a polyacrylamide gel following electrophoresis of the products of an in vitro XIAP cleavage assay.

In vitro cleavage of XIAP was apparent in the CEB extract. The observed molecular weight of the cleavage product was approximately 36 kDa (FIG. 23). The 10 kDa shift in the size of the cleavage product indicates that the observed product is derived from the amino-terminus of the recombinant protein, which contains six copies of the myc epitope (10 kDa). It thus appears that the cleavage product possesses at least two of the BIR domains, and that it is localized to the nucleus.

XIII. Treatment of HIV Infected Individuals

The expression of hiap-1 and hiap-2 is decreased significantly in HIV-infected human cells. Furthermore, this decrease precedes apoptosis. Therefore, administration of HIAP-1, HIAP-2, genes encoding these proteins, or compounds that upregulate these genes can be used to prevent T cell attrition in HIV-infected patients. The following assay may also be used to screen for compounds that alter hiap-1 and hiap-2 expression, and which also prevent apoptosis.

Figure 13A:
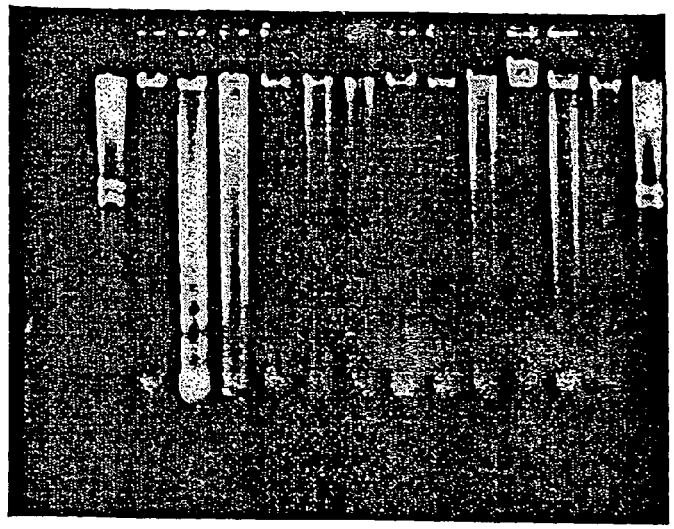
FIGS. 13A and 13B are photographs of agarose gels illustrating apoptotic DNA ladders and RT-PCR products using hiap-1 and hiap-2 specific probes in HIV-infected T cells.
Figure 13B:
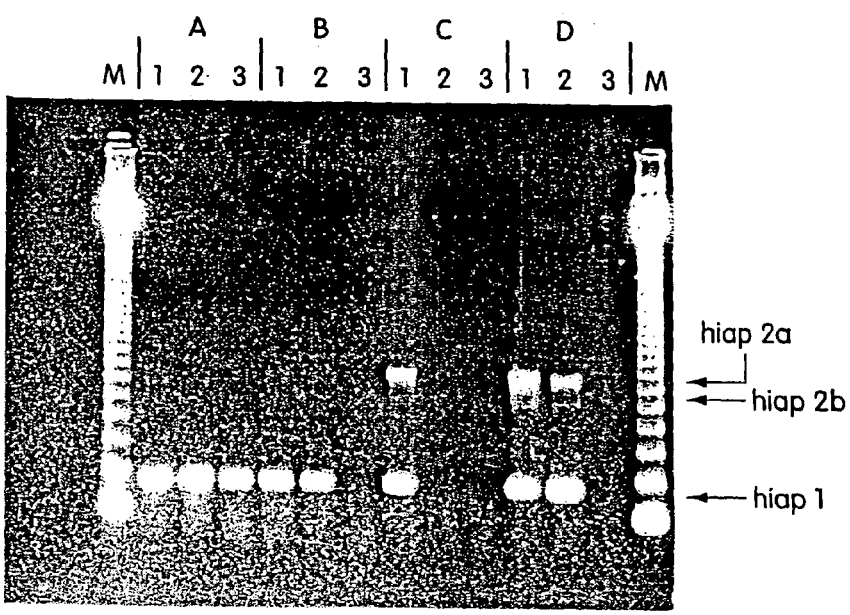

Cultured mature lymphocyte CD-4$^+$ T cell lines (H9, labelled "a"; CEM/CM-3, labelled "b"; 6T-CEM, labelled "c"; and Jurkat, labelled "d" in FIGS. 13A and 13B), were examined for signs of apoptosis (FIG. 13A) and hiap gene expression (FIG. 13B) after exposure to mitogens or HIV infection. Apoptosis was demonstrated by the appearance of DNA "laddering" upon gel electrophoresis and gene expression was assessed by PCR. The results obtained from normal (non-infected, non-mitogen stimulated) cells are shown in each lane labelled "1" in FIGS. 13A and 13B. The results obtained 24 hours after PHA/PMA (phytohemagglutinin/phorbol ester) stimulation are shown in each lane labelled "2". The results obtained 24 hours after HIV strain IIIB infection are shown in each lane labelled "3". The "M" refers to standard DNA markers (the 123 bp ladder in FIG. 13B, and the lambda HindIII ladder in FIG. 13A (both from Gibco-BRL)). DNA ladders (Prigent et al., J. Immunol. Meth., 160:139, 1993), which indicate apoptosis, are evident when DNA from the samples described above are electrophoresed on an ethidium bromide-stained agarose gel (FIG. 13A). The sensitivity and degree of apoptosis of the four T cell lines tested varies following mitogen stimulation and HIV infection.

In order to examine hiap gene expression, total RNA was prepared from the cultured cells and reverse transcribed using oligo-dT priming. The RT cDNA products were amplified by PCR using specific primers (as shown in Table 5) for the detection of hiap-2a, hiap-2b and hiap-1. The PCR was conducted using a Perkin Elmer 480 thermocycler with 35 cycles of the following program: 94° C. for one minute, 55° C. for 2 minutes and 72° C. for 1.5 minutes. The RT-PCR reaction products were electrophoresed on a 1% agarose gel, which was stained with ethidium bromide. Absence of hiap-2 transcripts is noted in all four cell lines 24 hours after HIV infection. In three of four cell lines (all except H9), the hiap-1 gene is also dramatically down-regulated after HIV infection. PHA/PMA mitogen stimulation also appears to decrease hiap gene expression; particularly of hiap-2 and to a lesser extent, of hiap-1. The data from these experiments is summarized in Table 5. The expression of β-actin was consistent in all cell lines tested, indicating that there is not a flaw in the RT-PCR assay that could account for the decrease in hiap gene expression.

TABLE 4

OLIGONUCLEOTIDE PRIMERS FOR THE SPECIFIC RT-PCR AMPLIFICATION OF UNIQUE IAP GENES

| IAP Gene | Forward Primer (nucleotide position*) | Reverse Primer (nucleotide position*) | Size of Product (bp) |
| --- | --- | --- | --- |
| h-xiap | p2415 (876–896) | p2449 (1291–1311) | 435 |
| m-xiap | p2566 (458–478) | p2490 (994–1013) | 555 |

TABLE 4-continued

OLIGONUCLEOTIDE PRIMERS FOR THE SPECIFIC RT-PCR
AMPLIFICATION OF UNIQUE IAP GENES

| IAP Gene | Forward Primer (nucleotide position*) | Reverse Primer (nucleotide position*) | Size of Product (bp) |
|---|---|---|---|
| h-hiap1 | p2465 (827–847) | p2464 (1008–1038) | 211 |
| m-hiap1 | p2687 (747–767) | p2684 (1177–1197) | 450 |
| hiap2 | p2595 (1562–1585) | p2578 (2339–2363) | 801[a] 618[b] |
| m-hiap2 | p2693 (1751–1772) | p2734 (2078–2100) | 349 |

*Nucleotide position as determined from FIGS. 1–4 for each IAP gene
[a]PCR product size of hiap2a
[b]PCR product size of hiap2b

TABLE 5

APOPTOSIS AND HIAP GENE EXPRESSION IN
CULTURED T-CELLS FOLLOWING
MITOGEN STIMULATION OR HIV INFECTION

| Cell Line | Condition | Apoptosis | hiap1 | hiap2 |
|---|---|---|---|---|
| H9 | not stimulated | – | + | ± |
| | PHA/PMA stimulated | +++ | + | ± |
| | HIV infected | ++ | + | – |
| CEM/CM-3 | not stimulated | – | + | ± |
| | PHA/PMA stimulated | ± | + | – |
| | HIV infected | ± | – | – |
| 6T-CEM | not stimulated | – | + | + |
| | PHA/PMA stimulated | ± | – | – |
| | HIV infected | + | – | – |
| Jurkat | not stimulated | – | + | ++ |
| | PHA/PMA stimulated | + | + | + |
| | HIV infected | ± | – | – |

XIV. Assignment of xiap, hiap-1, and hiap-2 To Chromosomes Xq25 and 11q22–23 by Fluorescence in situ Hybridization (FISH)

Fluorescence in situ hybridization (FISH) was used to identify the chromosomal location of xiap, hiap-1 and hiap-2. The probes used were cDNAs cloned in plasmid vectors: the 2.4 kb xiap clone included 1493 bp of coding sequence, 34bp of 5' UTR (untranslated region) and 913 bp of 3'UTR; the hiap-1 cDNA was 3.1 kb long and included 1812 bp coding and 1300 bp of 3' UTR; and the hiap-2 clone consisted of 1856 bp of coding and 1200 bp of 5' UTR. A total of 1 µg of probe DNA was labelled with biotin by nick translation (BRL). Chromosome spreads prepared from a normal peripheral blood culture were denatured for 2 minutes at 70° C. in 50% formamide/2×SSC and subsequently hybridized with the biotin labelled DNA probe for 18 hours at 37° C. in a solution consisting of 2×SSC/70% formamide/10% dextran sulfate. After hybridization, the spreads were washed in 2×SSC/50% formamide, followed by a wash in 2×SSC at 42° C. The biotin labelled DNA was detected by fluorescein isothiocyanate (FITC) conjugated avidin antibodies and anti-avidin antibodies (ONCOR detection kit), according to the manufacturer's instructions. Chromosomes were counterstained with propidium iodide and examined with a Olympus B×60 epifluorescence microscope. For chromosome identification, the slides with recorded labelled metaphase spreads were destained, dehydrated, dried, digested with trypsin for 30 seconds and stained with 4% Giemsa stain for 2 minutes. The chromosome spreads were relocated and the images were compared.

A total of 101 metaphase spreads were examined with the xiap probe, as described above. Symmetrical fluorescent signals on either one or both homologs of chromosome Xq25 were observed in 74% of the cells analyzed. Following staining with hiap-1 and hiap-2 probes, 56 cells were analyzed and doublet signals in the region 11q22–23 were observed in 83% of cells examined. The xiap gene was mapped to Xq25 while the hiap-1 and hiap-2 genes were mapped at the border of 11q22 and 11q23 bands.

These experiments confirmed the location of the xiap gene on chromosome Xq25. No highly consistent chromosomal abnormalities involving band Xq25 have been reported so far in any malignancies. However, deletions within this region are associated with a number of immune system defects including X-linked lymphoproliferative disease (Wu et al., Genomics 17:163, 1993).

Cytogenetic abnormalities of band 11q23 have been identified in more than 50% of infant leukemias regardless of the phenotype (Martinez-Climet et al., Leukaemia 9:1299, 1995). Rearrangements of the MLL Gene (mixed lineage leukemia or myeloid lymphoid leukemia; Ziemin Van der Poel et al., Proc. Natl. Acad. Sci. USA 88:10735, 1991) have been detected in 80% of cases with 11q23 translocation, however patients whose rearrangements clearly involved regions other than the MLL gene were also reported (Kobayashi et al., Blood 82:547, 1993). Thus, the IAP genes may follow the Bcl-2 paradigm, and would therefore play an important role in cancer transformation.

XV. Preventive Anti-Apoptotic Therapy

In a patient diagnosed to be heterozygous for an IAP mutation or to be susceptible to IAP mutations (even if those mutations do not yet result in alteration or loss of IAP biological activity), or a patient diagnosed as HIV positive, any of the above therapies may be administered before the occurrence of the disease phenotype. For example, the therapies may be provided to a patient who is HIV positive but does not yet show a diminished T cell count or other overt signs of AIDS. In particular, compounds shown to increase IAP expression or IAP biological activity may be administered by any standard dosage and route of administration (see above). Alternatively, gene therapy using an IAP expression construct may be undertaken to reverse or prevent the cell defect prior to the development of the degenerative disease.

The methods of the instant invention may be used to reduce or diagnose the disorders described herein in any mammal, for example, humans, domestic pets, or livestock. Where a non-human mammal is treated or diagnosed, the IAP polypeptide, nucleic acid, or antibody employed is preferably specific for that species.

OTHER EMBODIMENTS

In other embodiments, the invention includes any protein which is substantially identical to a mammalian IAP polypeptides (FIGS. 1–6; SEQ ID NOs: 1–42); such homologs include other substantially pure naturally-occurring mammalian IAP proteins as well as allelic variants; natural mutants; induced mutants; DNA sequences which encode proteins and also hybridize to the IAP DNA sequences of FIGS. 1–6 (SEQ ID NOS: 1–42) under high stringency conditions or, less preferably, under low stringency conditions (e.g., washing at 2×SSC at 40° C. with a probe length of at least 40 nucleotides); and proteins specifically bound by antisera directed to a IAP polypeptide. The term also includes chimeric polypeptides that include a IAP portion.

The invention further includes analogs of any naturally-occurring IAP polypeptide. Analogs can differ from the naturally-occurring IAP protein by amino acid sequence differences, by post-translational modifications, or by both. Analogs of the invention will generally exhibit at least 85%, more preferably 90%, and most preferably 95% or even 99% identity with all or part of a naturally occurring IAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring IAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or nonnaturally occurring or synthetic amino acids, e.g., β or γ amino acids. In addition to full-length polypeptides, the invention also includes IAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of IAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which facilitate specific detection of a IAP nucleic acid or amino acid sequence in a sample to be diagnosed. Particularly useful IAP fragments for this purpose include, without limitation, the amino acid fragments shown in Table 2.

SEQUENCE LISTING

```
<160> NUMBER OF SEQ ID NOS: 45

<210> SEQ ID NO 1
<211> LENGTH: 46
<212> TYPE: PRT
<213> ORGANISM: Artificial Sequence
<220> FEATURE:
<223> OTHER INFORMATION: Synthetic based on Homo sapiens, Mus musculus,
      Drosophila melanogaster, Cydia pomonella, and
      Orgyia pseudotsugata
<220> FEATURE:
<221> NAME/KEY: VARIANT
<222> LOCATION: (2)...(45)
<223> OTHER INFORMATION: Xaa at positions 2, 3, 4, 5,  6, 7, 9, 10, 11,
      17, 18, 19, 20, 21, 23, 25, 30, 31, 32, 34, 35,  38,
      39, 40, 41, 42, and 45 may be any amino acid.
<220> FEATURE:
<221> NAME/KEY: VARIANT
<222> LOCATION: (8)...(8)
<223> OTHER INFORMATION: Xaa at position 8 is Glu or Asp.
<220> FEATURE:
<221> NAME/KEY: VARIANT
<222> LOCATION: (14)...(14)
<223> OTHER INFORMATION: Xaa at position 14 is Val or Ile.
<220> FEATURE:
<221> NAME/KEY: VARIANT
<222> LOCATION: (22)...(22)
<223> OTHER INFORMATION: Xaa at position 22 is Val or Ile.

<400> SEQUENCE: 1

Glu Xaa Xaa Xaa Xaa Xaa Xaa Xaa Xaa Xaa Cys Lys Xaa Cys Met
  1               5                  10                  15

Xaa Xaa Xaa Xaa Xaa Xaa Xaa Phe Xaa Pro Cys Gly His Xaa Xaa Xaa
                 20                  25                  30

Cys Xaa Xaa Cys Ala Xaa Xaa Xaa Xaa Xaa Cys Pro Xaa Cys
            35                  40                  45

<210> SEQ ID NO 2
<211> LENGTH: 68
<212> TYPE: PRT
<213> ORGANISM: Artificial Sequence
<220> FEATURE:
<221> NAME/KEY: VARIANT
<222> LOCATION: (1)...(66)
<223> OTHER INFORMATION: Xaa at positions 1, 2, 3,  6, 9, 10, 14, 15,
```

-continued

```
       18, 19, 20, 21, 24, 30, 32, 33, 35, 37, 40, 42, 43,
       44, 45, 46, 47, 49, 50, 51, 53, 54, 55, 56, 57,
       59, 60, 61, 62, 64 and 66 may be any amino acid.
<221> NAME/KEY: VARIANT
<222> LOCATION: (13)...(17)
<223> OTHER INFORMATION: Xaa at positions 13, 16 and 17 may be any amino
       acid or may be absent.
<220> FEATURE:
<223> OTHER INFORMATION: Synthetic based on Homo sapiens, Mus musculus,
       Drosophila melanogaster, Cydia pomonella, and
       Orgyia pseudotsugata

<400> SEQUENCE: 2

Xaa Xaa Xaa Arg Leu Xaa Thr Phe Xaa Xaa Trp Pro Xaa Xaa Xaa Xaa
 1               5                  10                  15

Xaa Xaa Xaa Xaa Xaa Leu Ala Xaa Ala Gly Phe Tyr Tyr Xaa Gly Xaa
             20                  25                  30

Xaa Asp Xaa Val Xaa Cys Phe Xaa Cys Xaa Xaa Xaa Xaa Xaa Xaa Trp
         35                  40                  45

Xaa Xaa Xaa Asp Xaa Xaa Xaa Xaa His Xaa Xaa Xaa Xaa Pro Xaa
     50                  55                  60

Cys Xaa Phe Val
65

<210> SEQ ID NO 3
<211> LENGTH: 2540
<212> TYPE: DNA
<213> ORGANISM: Homo sapiens
<220> FEATURE:
<221> NAME/KEY: variation
<222> LOCATION: (2540)...(2540)
<223> OTHER INFORMATION: N may be any nucleotide

<400> SEQUENCE: 3
gaaaaggtgg acaagtccta ttttcaagag aagatgactt ttaacagttt tgaaggatct      60
aaaacttgtg tacctgcaga catcaataag gaagaagaat ttgtagaaga gtttaataga    120
ttaaaaactt ttgctaattt tccaagtggt agtcctgttt cagcatcaac actggcacga    180
gcagggtttc tttatactgg tgaaggagat accgtgcggt gctttagttg tcatgcagct    240
gtagatagat ggcaatatgg agactcagca gttggaagac acaggaaagt atccccaaat    300
tgcagattta tcaacggctt ttatcttgaa aatagtgcca cgcagtctac aaattctggt    360
atccagaatg gtcagtacaa agttgaaaac tatctgggaa gcagagatca ttttgcctta    420
gacaggccat ctgagacaca tgcagactat cttttgaaaa ctgggcaggt tgtagatata    480
tcagacacca tacccgag gaaccctgcc atgtattgtg aagaagctag attaaagtcc      540
tttcagaact ggccagacta tgctcaccta accccaagag agttagcaag tgctggactc    600
tactacacag gtattggtga ccaagtgcag tgcttttgtt gtggtggaaa actgaaaaat    660
tgggaacctt gtgatcgtgc ctggtcagaa cacaggcgac actttcctaa ttgcttcttt    720
gttttgggcc ggaatcttaa tattcgaagt gaatctgatg ctgtgagttc tgataggaat    780
ttcccaaatt caacaaatct tccaagaaat ccatccatgg cagattatga agcacggatc    840
tttacttttg ggacatggat atactcagtt aacaaggagc agcttgcaag agctggattt    900
tatgctttag gtgaaggtga taaagtaaag tgctttcact gtggaggagg gctaactgat    960
tggaagccca gtgaagaccc ttgggaacaa catgctaaat ggtatccagg gtgcaaatat   1020
ctgttagaac agaagggaca agaatatata aacaatattc atttaactca ttcacttgag   1080
gagtgtctgg taagaactac tgagaaaaca ccatcactaa ctagaagaat tgatgatacc   1140
```

```
                                           -continued atcttccaaa atcctatggt acaagaagct atacgaatgg ggttcagttt caaggacatt    1200
aagaaaataa tggaggaaaa aattcagata tctgggagca actataaatc acttgaggtt    1260
ctggttgcag atctagtgaa tgctcagaaa gacagtatgc aagatgagtc aagtcagact    1320
tcattacaga aagagattag tactgaagag cagctaaggc gcctgcaaga ggagaagctt    1380
tgcaaaatct gtatggatag aaatattgct atcgttttg ttccttgtgg acatctagtc    1440
acttgtaaac aatgtgctga agcagttgac aagtgtccca tgtgctacac agtcattact    1500
ttcaagcaaa aaattttat gtcttaatct aactctatag taggcatgtt atgttgttct    1560
tattaccctg attgaatgtg tgatgtgaac tgactttaag taatcaggat tgaattccat    1620
tagcatttgc taccaagtag gaaaaaaat gtacatggca gtgttttagt tggcaatata    1680
atctttgaat ttcttgattt ttcagggtat tagctgtatt atccattttt tttactgtta    1740
tttaattgaa accatagact aagaataaga agcatcatac tataactgaa cacaatgtgt    1800
attcatagta tactgattta atttctaagt gtaagtgaat taatcatctg gattttttat    1860
tcttttcaga taggcttaac aaatggagct ttctgtatat aaatgtggag attagagtta    1920
atctccccaa tcacataatt tgttttgtgt gaaaaggaa taaattgttc catgctggtg    1980
gaaagataga gattgttttt agaggttggt tgttgtgttt taggattctg tccattttct    2040
tgtaaaggga taaacacgga cgtgtgcgaa atatgtttgt aaagtgattt gccattgttg    2100
aaagcgtatt taatgataga atactatcga gccaacatgt actgacatgg aaagatgtca    2160
gagatatgtt aagtgtaaaa tgcaagtggc gggacactat gtatagtctg agccagatca    2220
aagtatgtat gttgttaata tgcatagaac gagagatttg gaaagatata caccaaactg    2280
ttaaatgtgg tttctcttcg gggagggggg gattggggga ggggcccag aggggtttta    2340 gagggccctt ttcactttcg acttttttca ttttgttctg ttcggatttt ttataagtat    2400
gtagaccccg aagggttta tgggaactaa catcagtaac ctaaccccg tgactatcct    2460 gtgctcttcc tagggagctg tgttgtttcc cacccaccac ccttccctct gaacaaatgc    2520
ctgagtgctg gggcactttn                                                2540

<210> SEQ ID NO 4
<211> LENGTH: 497
<212> TYPE: PRT
<213> ORGANISM: Homo sapiens

<400> SEQUENCE: 4

Met Thr Phe Asn Ser Phe Glu Gly Ser Lys Thr Cys Val Pro Ala Asp
 1               5                  10                  15

Ile Asn Lys Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125
```

```
Leu Asp Arg Pro Ser Glu Thr His Ala Asp Tyr Leu Leu Arg Thr Gly
        130                 135                 140

Gln Val Val Asp Ile Ser Asp Thr Ile Tyr Pro Arg Asn Pro Ala Met
145                 150                 155                 160

Tyr Cys Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
                180                 185                 190

Gly Ile Gly Asp Gln Val Gln Cys Phe Cys Gly Gly Lys Leu Lys
                195                 200                 205

Asn Trp Glu Pro Cys Asp Arg Ala Trp Ser Glu His Arg Arg His Phe
210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
                260                 265                 270

Gly Thr Trp Ile Tyr Ser Val Asn Lys Glu Gln Leu Ala Arg Ala Gly
                275                 280                 285

Phe Tyr Ala Leu Gly Glu Gly Asp Lys Val Lys Cys Phe His Cys Gly
                290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
                325                 330                 335

Glu Tyr Ile Asn Asn Ile His Leu Thr His Ser Leu Glu Glu Cys Leu
                340                 345                 350

Val Arg Thr Thr Glu Lys Thr Pro Ser Leu Thr Arg Arg Ile Asp Asp
                355                 360                 365

Thr Ile Phe Gln Asn Pro Met Val Gln Glu Ala Ile Arg Met Gly Phe
            370                 375                 380

Ser Phe Lys Asp Ile Lys Lys Ile Met Glu Glu Lys Ile Gln Ile Ser
385                 390                 395                 400

Gly Ser Asn Tyr Lys Ser Leu Glu Val Leu Val Ala Asp Leu Val Asn
                405                 410                 415

Ala Gln Lys Asp Ser Met Gln Asp Glu Ser Ser Gln Thr Ser Leu Gln
                420                 425                 430

Lys Glu Ile Ser Thr Glu Glu Gln Leu Arg Arg Leu Gln Glu Glu Lys
                435                 440                 445

Leu Cys Lys Ile Cys Met Asp Arg Asn Ile Ala Ile Val Phe Val Pro
                450                 455                 460

Cys Gly His Leu Val Thr Cys Lys Gln Cys Ala Glu Ala Val Asp Lys
465                 470                 475                 480

Cys Pro Met Cys Tyr Thr Val Ile Thr Phe Lys Gln Lys Ile Phe Met
                485                 490                 495

Ser
```

<210> SEQ ID NO 5
<211> LENGTH: 2676
<212> TYPE: DNA
<213> ORGANISM: Homo sapiens
<220> FEATURE:
<221> NAME/KEY: variation -continued
<222> LOCATION: (2470)...(2470)
<223> OTHER INFORMATION: N may be any nucleotide
<220> FEATURE:
<221> NAME/KEY: variation
<222> LOCATION: (2476)...(2476)
<223> OTHER INFORMATION: N may be any nucleotide
<220> FEATURE:
<221> NAME/KEY: variation
<222> LOCATION: (2483)...(2483)
<223> OTHER INFORMATION: N may be any nucleotide
<220> FEATURE:
<221> NAME/KEY: variation
<222> LOCATION: (2602)...(2602)
<223> OTHER INFORMATION: N may be any nucleotide

<400> SEQUENCE: 5

```
tccttgagat gtatcagtat aggatttagg atctccatgt tggaactcta aatgcataga      60
aatggaaata atgaaatttt tcattttgg cttttcagcc tagtattaaa actgataaaa     120
gcaaagccat gcacaaaact acctccctag agaaaggcta gtcccttttc ttccccattc     180
atttcattat gaacatagta gaaaacagca tattcttatc aaatttgatg aaaagcgcca     240
acacgtttga actgaaatac gacttgtcat gtgaactgta ccgaatgtct acgtattcca     300
cttttcctgc tggggttcct gtctcagaaa ggagtcttgc tcgtgctggt ttctattaca     360
ctggtgtgaa tgacaaggtc aaatgcttct gttgtggcct gatgctggat aactggaaaa     420
gaggagacag tcctactgaa agcataaaa agttgtatcc tagctgcaga ttcgttcaga     480
gtctaaattc cgttaacaac ttggaagcta cctctcagcc tactttcct tcttcagtaa     540
cacattccac acactcatta cttccgggta cagaaaacag tggatatttc cgtggctctt     600
attcaaactc tccatcaaat cctgtaaact ccagagcaaa tcaagaattt tctgccttga     660
tgagaagttc ctaccccctgt ccaatgaata acgaaaatgc cagattactt acttttcaga     720
catggccatt gacttttctg tcgccaacag atctggcacg agcaggcttt tactacatag     780
gacctggaga cagagtggct tgctttgcct gtggtgaaa attgagcaat gggaaccga     840
aggataatgc tatgtcagaa cacctgagac attttcccaa atgcccattt atagaaaatc     900
agcttcaaga cacttcaaga tacacagttt ctaatctgag catgcagaca catgcagccc     960
gctttaaaac attctttaac tggccctcta gtgttctagt taatcctgag cagcttgcaa    1020
gtgcgggttt ttattatgtg gtaacagtg atgatgtcaa atgcttttgc tgtgatggtg    1080
gactcaggtg ttgggaatct ggagatgatc catgggttca acatgccaag tggtttccaa    1140
ggtgtgagta cttgataaga attaaaggac aggagttcat ccgtcaagtt caagccagtt    1200
accctcatct acttgaacag ctgctatcca catcagacag cccaggagat gaaaatgcag    1260
agtcatcaat tatccatttg gaacctggag aagaccattc agaagatgca atcatgatga    1320
atactcctgt gattaatgct gccgtggaaa tgggctttag tagaagcctg gtaaaacaga    1380
cagttcagag aaaaatccta gcaactggag agaattatag actagtcaat gatcttgtgt    1440
tagacttact caatgcagaa gatgaaataa gggaagagga gagagaaaga gcaactgagg    1500
aaaaagaatc aaatgattta ttattaatcc ggaagaataa aatggcactt ttcaacatt    1560
tgacttgtgt aattccaatc ctggatagtc tactaactgc cggaattatt aatgaacaag    1620
aacatgatgt tattaaacag aagacacaga cgtctttaca agcaagagaa ctgattgata    1680
cgatttagt aaaaggaaat attgcagcca ctgtattcag aaactctctg caagaagctg    1740
aagctgtgtt atatgagcat ttatttgtgc aacaggacat aaaatatatt cccacagaag    1800
atgtttcaga tctaccagtg gaagaacaat tgcggagact accagaagaa agaacatgta    1860
```

-continued

```
aagtgtgtat ggacaaagaa gtgtccatag tgtttattcc ttgtggtcat ctagtagtat      1920
gcaaagattg tgctccttct ttaagaaagt gtcctatttg taggagtaca atcaagggta      1980
cagttcgtac atttctttca tgaagaagaa ccaaaacatc gtctaaactt tagaattaat      2040
ttattaaatg tattataact ttaactttta tcctaatttg gtttccttaa aattttatt      2100 tatttacaac tcaaaaaaca ttgttttgtg taacatattt atatatgtat ctaaaccata      2160
tgaacatata ttttttagaa actaagagaa tgataggctt ttgttcttat gaacgaaaaa      2220
gaggtagcac tacaaacaca atattcaatc caaatttcag cattattgaa attgtaagtg      2280
aagtaaaact taagatattt gagttaacct ttaagaattt taaatatttt ggcattgtac      2340
taataccggg aacatgaagc caggtgtggt ggtatgtacc tgtagtccca ggctgaggca      2400
agagaattac ttgagcccag gagtttgaat ccatcctggg cagcatactg agaccctgcc      2460
tttaaaaacn aacagnacca aanccaaaca ccagggacac atttctctgt cttttttgat      2520
cagtgtccta tacatcgaag gtgtgcatat atgttgaatc acattttagg gacatggtgt      2580
ttttataaag aattctgtga gnaaaaattt aataaagcaa ccaaattact cttaaaaaaa      2640
aaaaaaaaaa aaaaaactcg aggggcccgt accaat                                2676
```

<210> SEQ ID NO 6
<211> LENGTH: 604
<212> TYPE: PRT
<213> ORGANISM: Homo sapiens

<400> SEQUENCE: 6

```
Met Asn Ile Val Glu Asn Ser Ile Phe Leu Ser Asn Leu Met Lys Ser
 1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
    50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr His Ser Thr His Ser Leu Leu Pro Gly Thr
        115                 120                 125

Glu Asn Ser Gly Tyr Phe Arg Gly Ser Tyr Ser Asn Ser Pro Ser Asn
    130                 135                 140

Pro Val Asn Ser Arg Ala Asn Gln Glu Phe Ser Ala Leu Met Arg Ser
145                 150                 155                 160

Ser Tyr Pro Cys Pro Met Asn Asn Glu Asn Ala Arg Leu Leu Thr Phe
                165                 170                 175

Gln Thr Trp Pro Leu Thr Phe Leu Ser Pro Thr Asp Leu Ala Arg Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
    210                 215                 220

His Leu Arg His Phe Pro Lys Cys Pro Phe Ile Glu Asn Gln Leu Gln
```

-continued

```
                225                 230                 235                 240
Asp Thr Ser Arg Tyr Thr Val Ser Asn Leu Ser Met Gln Thr His Ala
                    245                 250                 255
Ala Arg Phe Lys Thr Phe Phe Asn Trp Pro Ser Ser Val Leu Val Asn
                260                 265                 270
Pro Glu Gln Leu Ala Ser Ala Gly Phe Tyr Tyr Val Gly Asn Ser Asp
            275                 280                 285
Asp Val Lys Cys Phe Cys Cys Asp Gly Gly Leu Arg Cys Trp Glu Ser
        290                 295                 300
Gly Asp Asp Pro Trp Val Gln His Ala Lys Trp Phe Pro Arg Cys Glu
305                 310                 315                 320
Tyr Leu Ile Arg Ile Lys Gly Gln Glu Phe Ile Arg Gln Val Gln Ala
                325                 330                 335
Ser Tyr Pro His Leu Leu Glu Gln Leu Leu Ser Thr Ser Asp Ser Pro
                340                 345                 350
Gly Asp Glu Asn Ala Glu Ser Ser Ile Ile His Leu Glu Pro Gly Glu
                355                 360                 365
Asp His Ser Glu Asp Ala Ile Met Met Asn Thr Pro Val Ile Asn Ala
            370                 375                 380
Ala Val Glu Met Gly Phe Ser Arg Ser Leu Val Lys Gln Thr Val Gln
385                 390                 395                 400
Arg Lys Ile Leu Ala Thr Gly Glu Asn Tyr Arg Leu Val Asn Asp Leu
                405                 410                 415
Val Leu Asp Leu Leu Asn Ala Glu Asp Glu Ile Arg Glu Glu Glu Arg
                420                 425                 430
Glu Arg Ala Thr Glu Glu Lys Glu Ser Asn Asp Leu Leu Leu Ile Arg
                435                 440                 445
Lys Asn Arg Met Ala Leu Phe Gln His Leu Thr Cys Val Ile Pro Ile
            450                 455                 460
Leu Asp Ser Leu Leu Thr Ala Gly Ile Ile Asn Glu Gln Glu His Asp
465                 470                 475                 480
Val Ile Lys Gln Lys Thr Gln Thr Ser Leu Gln Ala Arg Glu Leu Ile
                485                 490                 495
Asp Thr Ile Leu Val Lys Gly Asn Ile Ala Ala Thr Val Phe Arg Asn
                500                 505                 510
Ser Leu Gln Glu Ala Glu Ala Val Leu Tyr Glu His Leu Phe Val Gln
            515                 520                 525
Gln Asp Ile Lys Tyr Ile Pro Thr Glu Asp Val Ser Asp Leu Pro Val
        530                 535                 540
Glu Glu Gln Leu Arg Arg Leu Pro Glu Glu Arg Thr Cys Lys Val Cys
545                 550                 555                 560
Met Asp Lys Glu Val Ser Ile Val Phe Ile Pro Cys Gly His Leu Val
                565                 570                 575
Val Cys Lys Asp Cys Ala Pro Ser Leu Arg Lys Cys Pro Ile Cys Arg
            580                 585                 590
Ser Thr Ile Lys Gly Thr Val Arg Thr Phe Leu Ser
                595                 600

<210> SEQ ID NO 7
<211> LENGTH: 2580
<212> TYPE: DNA
<213> ORGANISM: Homo sapiens
<220> FEATURE:
<221> NAME/KEY: variation
<222> LOCATION: (2412)...(2412)
```

<223> OTHER INFORMATION: N may be any nucleotide

<400> SEQUENCE: 7

| | | | | | |
|---|---|---|---|---|---|
| ttaggttacc | tgaaagagtt | actacaaccc | caaagagttg | tgttctaagt | agtatcttgg | 60 |
| taattcagag | agatactcat | cctacctgaa | tataaactga | gataaatcca | gtaaagaaag | 120 |
| tgtagtaaat | tctacataag | agtctatcat | tgatttcttt | ttgtggtgga | aatcttagtt | 180 |
| catgtgaaga | aatttcatgt | gaatgtttta | gctatcaaac | agtactgtca | cctactcatg | 240 |
| cacaaaactg | cctcccaaag | acttttccca | ggtccctcgt | atcaaaacat | taagagtata | 300 |
| atggaagata | gcacgatctt | gtcagattgg | acaaacagca | acaaacaaaa | aatgaagtat | 360 |
| gactttcct | gtgaactcta | cagaatgtct | acatattcaa | ctttccccgc | cggggtgcct | 420 |
| gtctcagaaa | ggagtcttgc | tcgtgctggt | ttttattata | ctggtgtgaa | tgacaaggtc | 480 |
| aaatgcttct | gttgtggcct | gatgctggat | aactggaaac | taggagacag | tcctattcaa | 540 |
| aagcataaac | agctatatcc | tagctgtagc | tttattcaga | atctggtttc | agctagtctg | 600 |
| ggatccacct | ctaagaatac | gtctccaatg | agaaacagtt | ttgcacattc | attatctccc | 660 |
| accttggaac | atagtagctt | gttcagtggt | tcttactcca | gccttcctcc | aaaccctctt | 720 |
| aattctagag | cagttgaaga | catctcttca | tcgaggacta | ccccctacag | ttatgcaatg | 780 |
| agtactgaag | aagccagatt | tcttacctac | catatgtggc | cattaacttt | tttgtcacca | 840 |
| tcagaattgg | caagagctgg | ttttattat | ataggacctg | agatagggt | agcctgcttt | 900 |
| gcctgtggtg | ggaagctcag | taactgggaa | ccaaaggatg | atgctatgtc | agaacaccgg | 960 |
| aggcattttc | ccaactgtcc | atttttggaa | aattctctag | aaactctgag | gtttagcatt | 1020 |
| tcaaatctga | gcatgcagac | acatgcagct | cgaatgagaa | catttatgta | ctggccatct | 1080 |
| agtgttccag | ttcagcctga | gcagcttgca | agtgctggtt | tttattatgt | gggtcgcaat | 1140 |
| gatgatgtca | aatgctttgg | ttgtgatggt | ggcttgaggt | gttgggaatc | tggagatgat | 1200 |
| ccatgggtag | aacatgccaa | gtggtttcca | aggtgtgagt | tcttgatacg | aatgaaaggc | 1260 |
| caagagtttg | ttgatgagat | tcaaggtaga | tatcctcatc | ttcttgaaca | gctgttgtca | 1320 |
| acttcagata | ccactggaga | agaaaatgct | gacccaccaa | ttattcattt | tggacctgga | 1380 |
| gaaagttctt | cagaagatgc | tgtcatgatg | aatacacctg | tggttaaatc | tgccttggaa | 1440 |
| atgggcttta | atagagacct | ggtgaaacaa | acagttctaa | gtaaaatcct | gacaactgga | 1500 |
| gagaactata | aaacagttaa | tgatattgtg | tcagcacttc | ttaatgctga | agatgaaaaa | 1560 |
| agagaagagg | agaaggaaaa | acaagctgaa | gaaatggcat | cagatgattt | gtcattaatt | 1620 |
| cggaagaaca | gaatggctct | ctttcaacaa | ttgacatgtg | tgcttcctat | cctggataat | 1680 |
| cttttaaagg | ccaatgtaat | taataaacag | gaacatgata | ttattaaaca | aaaaacacag | 1740 |
| ataccttac | aagcgagaga | actgattgat | accatttggg | ttaaaggaaa | tgctgcggcc | 1800 |
| aacatcttca | aaaactgtct | aaaagaaatt | gactctacat | tgtataagaa | cttatttgtg | 1860 |
| gataagaata | tgaagtatat | tccaacagaa | gatgtttcag | gtctgtcact | ggaagaacaa | 1920 |
| ttgaggaggt | tgcaagaaga | acgaacttgt | aaagtgtgta | tggacaaaga | agtttctgtt | 1980 |
| gtatttattc | cttgtggtca | tctggtagta | tgccaggaat | gtgccccttc | tctaagaaaa | 2040 |
| tgccctattt | gcagggtat | aatcaagggt | actgttcgta | catttctctc | ttaaagaaaa | 2100 |
| atagtctata | ttttaacctg | cataaaaagg | tctttaaaat | attgttgaac | acttgaagcc | 2160 |
| atctaaagta | aaaagggaat | tatgagtttt | tcaattagta | acattcatgt | tctagtctgc | 2220 |
| tttggtacta | ataatcttgt | ttctgaaaag | atggtatcat | atatttaatc | ttaatctgtt | 2280 |

```
tatttacaag ggaagattta tgtttggtga actatattag tatgtatgtg tacctaaggg    2340
agtagcgtcn ctgcttgtta tgcatcattt caggagttac tggatttgtt gttctttcag    2400
aaagctttga anactaaatt atagtgtaga aaagaactgg aaaccaggaa ctctggagtt    2460
catcagagtt atggtgccga attgtctttg gtgcttttca cttgtgtttt aaaataagga    2520 ttttctctt atttctcccc ctagtttgtg agaaacatct caataaagtg ctttaaaaag     2580
```

<210> SEQ ID NO 8
<211> LENGTH: 618
<212> TYPE: PRT
<213> ORGANISM: Homo sapiens

<400> SEQUENCE: 8

```
Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
            20                  25                  30

Asn Ser Asn Lys Gln Lys Met Lys Tyr Asp Phe Ser Cys Glu Leu Tyr
        35                  40                  45

Arg Met Ser Thr Tyr Ser Thr Phe Pro Ala Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
            100                 105                 110

Ile Gln Asn Leu Val Ser Ala Ser Leu Gly Ser Thr Ser Lys Asn Thr
        115                 120                 125

Ser Pro Met Arg Asn Ser Phe Ala His Ser Leu Ser Pro Thr Leu Glu
    130                 135                 140

His Ser Ser Leu Phe Ser Gly Ser Tyr Ser Ser Leu Pro Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
    290                 295                 300

Lys Cys Phe Gly Cys Asp Gly Gly Leu Arg Cys Trp Glu Ser Gly Asp
305                 310                 315                 320
```

-continued

```
Asp Pro Trp Val Glu His Ala Lys Trp Phe Pro Arg Cys Glu Phe Leu
            325                 330                 335
Ile Arg Met Lys Gly Gln Glu Phe Val Asp Glu Ile Gln Gly Arg Tyr
        340                 345                 350
Pro His Leu Leu Glu Gln Leu Leu Ser Thr Ser Asp Thr Thr Gly Glu
    355                 360                 365
Glu Asn Ala Asp Pro Ile Ile His Phe Gly Pro Gly Glu Ser Ser
370                 375                 380
Ser Glu Asp Ala Val Met Met Asn Thr Pro Val Val Lys Ser Ala Leu
385                 390                 395                 400
Glu Met Gly Phe Asn Arg Asp Leu Val Lys Gln Thr Val Leu Ser Lys
                405                 410                 415
Ile Leu Thr Thr Gly Glu Asn Tyr Lys Thr Val Asn Asp Ile Val Ser
            420                 425                 430
Ala Leu Leu Asn Ala Glu Asp Glu Lys Arg Glu Glu Lys Glu Lys
        435                 440                 445
Gln Ala Glu Glu Met Ala Ser Asp Asp Leu Ser Leu Ile Arg Lys Asn
    450                 455                 460
Arg Met Ala Leu Phe Gln Gln Leu Thr Cys Val Leu Pro Ile Leu Asp
465                 470                 475                 480
Asn Leu Leu Lys Ala Asn Val Ile Asn Lys Gln Glu His Asp Ile Ile
                485                 490                 495
Lys Gln Lys Thr Gln Ile Pro Leu Gln Ala Arg Glu Leu Ile Asp Thr
            500                 505                 510
Ile Trp Val Lys Gly Asn Ala Ala Ala Asn Ile Phe Lys Asn Cys Leu
        515                 520                 525
Lys Glu Ile Asp Ser Thr Leu Tyr Lys Asn Leu Phe Val Asp Lys Asn
    530                 535                 540
Met Lys Tyr Ile Pro Thr Glu Asp Val Ser Gly Leu Ser Leu Glu Glu
545                 550                 555                 560
Gln Leu Arg Arg Leu Gln Glu Arg Thr Cys Lys Val Cys Met Asp
                565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
        595                 600                 605
Ile Lys Gly Thr Val Arg Thr Phe Leu Ser
    610                 615
```

<210> SEQ ID NO 9
<211> LENGTH: 2100
<212> TYPE: DNA
<213> ORGANISM: Mus musculus

<400> SEQUENCE: 9

```
gacactctgc tgggcggcgg gccgccctcc tccgggacct cccctcggga accgtcgccc      60
gcggcgctta gttaggactg gagtgcttgg cgcgaaaagg tggacaagtc ctattttcca     120
gagaagatga cttttaacag ttttgaagga actagaactt ttgtacttgc agacaccaat     180
aaggatgaag aatttgtaga agagtttaat agattaaaaa catttgctaa cttcccaagt     240
agtagtcctg tttcagcatc aacattggcg cgagctgggt ttctttatac cggtgaagga     300
gacaccgtgc aatgtttcag ttgtcatgcg caatagata gatggcagta tggagactca     360
gctgttggaa gacacaggag aatatcccca aattgcagat ttatcaatgg ttttattttt     420
```

```
gaaaatggtg ctgcacagtc tacaaatcct ggtatccaaa atggccagta caaatctgaa    480
aactgtgtgg gaaatagaaa tccttttgcc cctgacaggc cacctgagac tcatgctgat    540
tatctcttga aactggaca ggttgtagat atttcagaca ccatataccc gaggaaccct     600
gccatgtgta gtgaagaagc cagattgaag tcatttcaga actggccgga ctatgctcat    660
ttaaccccca gagagttagc tagtgctggc ctctactaca cagggctga tgatcaagtg     720
caatgctttt gttgtggggg aaaactgaaa aattgggaac cctgtgatcg tgcctggtca    780
gaacacagga gacactttcc caattgcttt tttgttttgg ccggaacgt taatgttcga     840
agtgaatctg gtgtgagttc tgataggaat ttcccaaatt caacaaactc tccaagaaat    900
ccagccatgg cagaatatga agcacggatc gttacttttg aacatggat atactcagtt     960
aacaaggagc agcttgcaag agctggattt tatgctttag gtgaaggcga taaagtgaag   1020
tgcttccact gtggaggagg gctcacggat tggaagccaa gtgaagaccc ctgggaccag   1080
catgctaagt gctacccagg gtgcaaatac ctattggatg agaaggggca agaatatata   1140
aataatattc atttaaccca tccacttgag gaatctttgg gaagaactgc tgaaaaaaca   1200
ccaccgctaa ctaaaaaaat cgatgatacc atcttccaga atcctatggt gcaagaagct   1260
atacgaatgg gatttagctt caaggacctt aagaaaacaa tggaagaaaa aatccaaaca   1320
tccgggagca gctatctatc acttgaggtc ctgattgcag atcttgtgag tgctcagaaa   1380
gataatacgg aggatgagtc aagtcaaact tcattgcaga aagacattag tactgaagag   1440
cagctaaggc gcctacaaga ggagaagctt tccaaaatct gtatggatag aaatattgct   1500
atcgtttttt ttccttgtgg acatctggcc acttgtaaac agtgtgcaga agcagttgac   1560
aaaatgtccca tgtgctacac cgtcattacg ttcaaccaaa aaattttttat gtcttagtgg   1620
ggcaccacat gttatgttct tcttgctcta attgaatgtg taatgggagc gaactttaag   1680
taatcctgca tttgcattcc attagcatcc tgctgtttcc aaatggagac caatgctaac   1740
agcactgttt ccgtctaaac attcaatttc tggatctttc gagttatcag ctgtatcatt   1800
tagccagtgt tttactcgat tgaaaccta gacagagaag catttatag cttttcacat     1860
gtatattggt agtacactga cttgatttct atatgtaagt gaattcatca cctgcatgtt   1920
tcatgccttt tgcataagct taacaaatgg agtgttctgt ataagcatgg agatgtgatg   1980
gaatctgccc aatgacttta attggcttat tgtaaacacg gaaagaactg ccccacgctg   2040
ctgggaggat aaagattgtt ttagatgctc acttctgtgt tttaggattc tgcccattta   2100
```

<210> SEQ ID NO 10
<211> LENGTH: 496
<212> TYPE: PRT
<213> ORGANISM: Mus musculus

<400> SEQUENCE: 10

Met Thr Phe Asn Ser Phe Glu Gly Thr Arg Thr Phe Val Leu Ala Asp
1               5                   10                  15

Thr Asn Lys Asp Glu Glu Phe Val Glu Glu Phe Asn Arg Leu Lys Thr
            20                  25                  30

Phe Ala Asn Phe Pro Ser Ser Ser Pro Val Ser Ala Ser Thr Leu Ala
        35                  40                  45

Arg Ala Gly Phe Leu Tyr Thr Gly Glu Gly Asp Thr Val Gln Cys Phe
    50                  55                  60

Ser Cys His Ala Ala Ile Asp Arg Trp Gln Tyr Gly Asp Ser Ala Val
65                  70                  75                  80

```
Gly Arg His Arg Arg Ile Ser Pro Asn Cys Arg Phe Ile Asn Gly Phe
                85                  90                  95

Tyr Phe Glu Asn Gly Ala Ala Gln Ser Thr Asn Pro Gly Ile Gln Asn
            100                 105                 110

Gly Gln Tyr Lys Ser Glu Asn Cys Val Gly Asn Arg Asn Pro Phe Ala
        115                 120                 125

Pro Asp Arg Pro Pro Glu Thr His Ala Asp Tyr Leu Leu Arg Thr Gly
130                 135                 140

Gln Val Val Asp Ile Ser Asp Thr Ile Tyr Pro Arg Asn Pro Ala Met
145                 150                 155                 160

Cys Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ala Asp Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
        210                 215                 220

Pro Asn Cys Phe Phe Val Leu Gly Arg Asn Val Asn Val Arg Ser Glu
225                 230                 235                 240

Ser Gly Val Ser Ser Asp Arg Asn Phe Pro Asn Ser Thr Asn Ser Pro
                245                 250                 255

Arg Asn Pro Ala Met Ala Glu Tyr Glu Ala Arg Ile Val Thr Phe Gly
            260                 265                 270

Thr Trp Ile Tyr Ser Val Asn Lys Glu Gln Leu Ala Arg Ala Gly Phe
        275                 280                 285

Tyr Ala Leu Gly Glu Gly Asp Lys Val Lys Cys Phe His Cys Gly Gly
    290                 295                 300

Gly Leu Thr Asp Trp Lys Pro Ser Glu Asp Pro Trp Asp Gln His Ala
305                 310                 315                 320

Lys Cys Tyr Pro Gly Cys Lys Tyr Leu Leu Asp Glu Lys Gly Gln Glu
                325                 330                 335

Tyr Ile Asn Asn Ile His Leu Thr His Pro Leu Glu Glu Ser Leu Gly
            340                 345                 350

Arg Thr Ala Glu Lys Thr Pro Pro Leu Thr Lys Lys Ile Asp Asp Thr
        355                 360                 365

Ile Phe Gln Asn Pro Met Val Gln Glu Ala Ile Arg Met Gly Phe Ser
370                 375                 380

Phe Lys Asp Leu Lys Lys Thr Met Glu Glu Lys Ile Gln Thr Ser Gly
385                 390                 395                 400

Ser Ser Tyr Leu Ser Leu Glu Val Leu Ile Ala Asp Leu Val Ser Ala
                405                 410                 415

Gln Lys Asp Asn Thr Glu Asp Glu Ser Ser Gln Thr Ser Leu Gln Lys
            420                 425                 430

Asp Ile Ser Thr Glu Glu Gln Leu Arg Arg Leu Gln Glu Glu Lys Leu
        435                 440                 445

Ser Lys Ile Cys Met Asp Arg Asn Ile Ala Ile Val Phe Phe Pro Cys
450                 455                 460

Gly His Leu Ala Thr Cys Lys Gln Cys Ala Glu Ala Val Asp Lys Cys
465                 470                 475                 480

Pro Met Cys Tyr Thr Val Ile Thr Phe Asn Gln Lys Ile Phe Met Ser
                485                 490                 495
```

```
<210> SEQ ID NO 11
<211> LENGTH: 67
<212> TYPE: PRT
<213> ORGANISM: Orgyia pseudotsugata

<400> SEQUENCE: 11

Lys Ala Ala Arg Leu Gly Thr Tyr Thr Asn Trp Pro Val Gln Phe Leu
 1               5                  10                  15

Glu Pro Ser Arg Met Ala Ala Ser Gly Phe Tyr Tyr Leu Gly Arg Gly
            20                  25                  30

Asp Glu Val Arg Cys Ala Phe Cys Lys Val Glu Ile Thr Asn Trp Val
        35                  40                  45

Arg Gly Asp Asp Pro Glu Thr Asp His Lys Arg Trp Ala Pro Gln Cys
    50                  55                  60

Pro Phe Val
65

<210> SEQ ID NO 12
<211> LENGTH: 275
<212> TYPE: PRT
<213> ORGANISM: Cydia pomonella

<400> SEQUENCE: 12

Met Ser Asp Leu Arg Leu Glu Glu Val Arg Leu Asn Thr Phe Glu Lys
 1               5                  10                  15

Trp Pro Val Ser Phe Leu Ser Pro Glu Thr Met Ala Lys Asn Gly Phe
            20                  25                  30

Tyr Tyr Leu Gly Arg Ser Asp Glu Val Arg Cys Ala Phe Cys Lys Val
        35                  40                  45

Glu Ile Met Arg Trp Lys Glu Gly Glu Asp Pro Ala Ala Asp His Lys
    50                  55                  60

Lys Trp Ala Pro Gln Cys Pro Phe Val Lys Gly Ile Asp Val Cys Gly
65                  70                  75                  80

Ser Ile Val Thr Thr Asn Asn Ile Gln Asn Thr Thr Thr His Asp Thr
                85                  90                  95

Ile Ile Gly Pro Ala His Pro Lys Tyr Ala His Glu Ala Ala Arg Val
            100                 105                 110

Lys Ser Phe His Asn Trp Pro Arg Cys Met Lys Gln Arg Pro Glu Gln
        115                 120                 125

Met Ala Asp Ala Gly Phe Phe Tyr Thr Gly Tyr Gly Asp Asn Thr Lys
    130                 135                 140

Cys Phe Tyr Cys Asp Gly Gly Leu Lys Asp Trp Glu Pro Glu Asp Val
145                 150                 155                 160

Pro Trp Glu Gln His Val Arg Trp Phe Asp Arg Cys Ala Tyr Val Gln
                165                 170                 175

Leu Val Lys Gly Arg Asp Tyr Val Gln Lys Val Ile Thr Glu Ala Cys
            180                 185                 190

Val Leu Pro Gly Glu Asn Thr Thr Val Ser Thr Ala Ala Pro Val Ser
        195                 200                 205

Glu Pro Ile Pro Glu Thr Lys Ile Glu Lys Glu Pro Gln Val Glu Asp
    210                 215                 220

Ser Lys Leu Cys Lys Ile Cys Tyr Val Glu Glu Cys Ile Val Cys Phe
225                 230                 235                 240

Val Pro Cys Gly His Val Val Ala Cys Ala Lys Cys Ala Leu Ser Val
                245                 250                 255

Asp Lys Cys Pro Met Cys Arg Lys Ile Val Thr Ser Val Leu Lys Val
```

```
                260                 265                 270
Tyr Phe Ser
        275

<210> SEQ ID NO 13
<211> LENGTH: 498
<212> TYPE: PRT
<213> ORGANISM: Drosophila melanogaster

<400> SEQUENCE: 13

Met Thr Glu Leu Gly Met Glu Leu Glu Ser Val Arg Leu Ala Thr Phe
 1               5                  10                  15

Gly Glu Trp Pro Leu Asn Ala Pro Val Ser Ala Glu Asp Leu Val Ala
            20                  25                  30

Asn Gly Phe Phe Ala Thr Gly Lys Trp Leu Glu Ala Glu Cys His Phe
        35                  40                  45

Cys His Val Arg Ile Asp Arg Trp Glu Tyr Gly Asp Gln Val Ala Glu
    50                  55                  60

Arg His Arg Arg Ser Ser Pro Ile Cys Ser Met Val Leu Ala Pro Asn
65                  70                  75                  80

His Cys Gly Asn Val Pro Arg Ser Gln Glu Ser Asp Asn Glu Gly Asn
                85                  90                  95

Ser Val Val Asp Ser Pro Glu Ser Cys Ser Cys Pro Asp Leu Leu Leu
            100                 105                 110

Glu Ala Asn Arg Leu Val Thr Phe Lys Asp Trp Pro Asn Pro Asn Ile
        115                 120                 125

Thr Pro Gln Ala Leu Ala Lys Ala Gly Phe Tyr Tyr Leu Asn Arg Leu
    130                 135                 140

Asp His Val Lys Cys Val Trp Cys Asn Gly Val Ile Ala Lys Trp Glu
145                 150                 155                 160

Lys Asn Asp Asn Ala Phe Glu Glu His Lys Arg Phe Phe Pro Gln Cys
                165                 170                 175

Pro Arg Val Gln Met Gly Pro Leu Ile Glu Phe Ala Thr Gly Lys Asn
            180                 185                 190

Leu Asp Glu Leu Gly Ile Gln Pro Thr Thr Leu Pro Leu Arg Pro Lys
        195                 200                 205

Tyr Ala Cys Val Asp Ala Arg Leu Arg Thr Phe Thr Asp Trp Pro Ile
    210                 215                 220

Ser Asn Ile Gln Pro Ala Ser Ala Leu Ala Gln Ala Gly Leu Tyr Tyr
225                 230                 235                 240

Gln Lys Ile Gly Asp Gln Val Arg Cys Phe His Cys Asn Ile Gly Leu
                245                 250                 255

Arg Ser Trp Gln Lys Glu Asp Glu Pro Trp Phe Glu His Ala Lys Trp
            260                 265                 270

Ser Pro Lys Cys Gln Phe Val Leu Leu Ala Lys Gly Pro Ala Tyr Val
        275                 280                 285

Ser Glu Val Leu Ala Thr Thr Ala Ala Asn Ala Ser Ser Gln Pro Ala
    290                 295                 300

Thr Ala Pro Ala Pro Thr Leu Gln Ala Asp Val Leu Met Asp Glu Ala
305                 310                 315                 320

Pro Ala Lys Glu Ala Leu Thr Leu Gly Ile Asp Gly Gly Val Val Arg
                325                 330                 335

Asn Ala Ile Gln Arg Lys Leu Leu Ser Ser Gly Cys Ala Phe Ser Thr
            340                 345                 350
```

```
Leu Asp Glu Leu Leu His Asp Ile Phe Asp Asp Ala Gly Ala Gly Ala
            355                 360                 365

Ala Leu Glu Val Arg Glu Pro Pro Glu Pro Ser Ala Pro Phe Ile Glu
        370                 375                 380

Pro Cys Gln Ala Thr Thr Ser Lys Ala Ala Ser Val Pro Ile Pro Val
385                 390                 395                 400

Ala Asp Ser Ile Pro Ala Lys Pro Gln Ala Ala Glu Ala Val Ser Asn
                405                 410                 415

Ile Ser Lys Ile Thr Asp Glu Ile Gln Lys Met Ser Val Ser Thr Pro
            420                 425                 430

Asn Gly Asn Leu Ser Leu Glu Glu Asn Arg Gln Leu Lys Asp Ala
        435                 440                 445

Arg Leu Cys Lys Val Cys Leu Asp Glu Glu Val Gly Val Val Phe Leu
    450                 455                 460

Pro Cys Gly His Leu Ala Thr Cys Asn Gln Cys Ala Pro Ser Val Ala
465                 470                 475                 480

Asn Cys Pro Met Cys Arg Ala Asp Ile Lys Gly Phe Val Arg Thr Phe
                485                 490                 495

Leu Ser

<210> SEQ ID NO 14
<211> LENGTH: 67
<212> TYPE: PRT
<213> ORGANISM: Cydia pomonella

<400> SEQUENCE: 14

Glu Glu Val Arg Leu Asn Thr Phe Glu Lys Trp Pro Val Ser Phe Leu
1               5                   10                  15

Ser Pro Glu Thr Met Ala Lys Asn Gly Phe Tyr Tyr Leu Gly Arg Ser
            20                  25                  30

Asp Glu Val Arg Cys Ala Phe Cys Lys Val Glu Ile Met Arg Trp Lys
        35                  40                  45

Glu Gly Glu Asp Pro Ala Ala Asp His Lys Lys Trp Ala Pro Gln Cys
    50                  55                  60

Pro Phe Val
65

<210> SEQ ID NO 15
<211> LENGTH: 67
<212> TYPE: PRT
<213> ORGANISM: Drosophila melanogaster

<400> SEQUENCE: 15

Glu Ala Asn Arg Leu Val Thr Phe Lys Asp Trp Pro Asn Pro Asn Ile
1               5                   10                  15

Thr Pro Gln Ala Leu Ala Lys Ala Gly Phe Tyr Tyr Leu Asn Arg Leu
            20                  25                  30

Asp His Val Lys Cys Val Trp Cys Asn Gly Val Ile Ala Lys Trp Glu
        35                  40                  45

Lys Asn Asp Asn Ala Phe Glu Glu His Lys Arg Phe Phe Pro Gln Cys
    50                  55                  60

Pro Arg Val
65

<210> SEQ ID NO 16
<211> LENGTH: 68
<212> TYPE: PRT
```

<213> ORGANISM: Mus musculus

<400> SEQUENCE: 16

Glu Phe Asn Arg Leu Lys Thr Phe Ala Asn Phe Pro Ser Ser Ser Pro
1               5                   10                  15

Val Ser Ala Ser Thr Leu Ala Arg Ala Gly Phe Leu Tyr Thr Gly Glu
            20                  25                  30

Gly Asp Thr Val Gln Cys Phe Ser Cys His Ala Ala Ile Asp Arg Trp
        35                  40                  45

Gln Tyr Gly Asp Ser Ala Val Gly Arg His Arg Ile Ser Pro Asn
    50                  55                  60

Cys Arg Phe Ile
65

<210> SEQ ID NO 17
<211> LENGTH: 68
<212> TYPE: PRT
<213> ORGANISM: Homo sapiens

<400> SEQUENCE: 17

Glu Phe Asn Arg Leu Lys Thr Phe Ala Asn Phe Pro Ser Gly Ser Pro
1               5                   10                  15

Val Ser Ala Ser Thr Leu Ala Arg Ala Gly Phe Leu Tyr Thr Gly Glu
            20                  25                  30

Gly Asp Thr Val Arg Cys Phe Ser Cys His Ala Ala Val Asp Arg Trp
        35                  40                  45

Gln Tyr Gly Asp Ser Ala Val Gly Arg His Arg Lys Val Ser Pro Asn
    50                  55                  60

Cys Arg Phe Ile
65

<210> SEQ ID NO 18
<211> LENGTH: 68
<212> TYPE: PRT
<213> ORGANISM: Homo sapiens

<400> SEQUENCE: 18

Glu Leu Tyr Arg Met Ser Thr Tyr Ser Thr Phe Pro Ala Gly Val Pro
1               5                   10                  15

Val Ser Glu Arg Ser Leu Ala Arg Ala Gly Phe Tyr Tyr Thr Gly Val
            20                  25                  30

Asn Asp Lys Val Lys Cys Phe Cys Cys Gly Leu Met Leu Asp Asn Trp
        35                  40                  45

Lys Arg Gly Asp Ser Pro Thr Glu Lys His Lys Lys Leu Tyr Pro Ser
    50                  55                  60

Cys Arg Phe Val
65

<210> SEQ ID NO 19
<211> LENGTH: 68
<212> TYPE: PRT
<213> ORGANISM: Homo sapiens

<400> SEQUENCE: 19

Glu Leu Tyr Arg Met Ser Thr Tyr Ser Thr Phe Pro Ala Gly Val Pro
1               5                   10                  15

Val Ser Glu Arg Ser Leu Ala Arg Ala Gly Phe Tyr Tyr Thr Gly Val
            20                  25                  30

Asn Asp Lys Val Lys Cys Phe Cys Cys Gly Leu Met Leu Asp Asn Trp
            35                  40                  45

Lys Leu Gly Asp Ser Pro Ile Gln Lys His Lys Gln Leu Tyr Pro Ser
        50                  55                  60

Cys Ser Phe Ile
65

<210> SEQ ID NO 20
<211> LENGTH: 68
<212> TYPE: PRT
<213> ORGANISM: Mus musculus

<400> SEQUENCE: 20

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ala
            20                  25                  30

Asp Asp Gln Val Gln Cys Phe Cys Cys Gly Gly Lys Leu Lys Asn Trp
            35                  40                  45

Glu Pro Cys Asp Arg Ala Trp Ser Glu His Arg Arg His Phe Pro Asn
        50                  55                  60

Cys Phe Phe Val
65

<210> SEQ ID NO 21
<211> LENGTH: 68
<212> TYPE: PRT
<213> ORGANISM: Homo sapiens

<400> SEQUENCE: 21

Glu Glu Ala Arg Leu Lys Ser Phe Gln Asn Trp Pro Asp Tyr Ala His
1               5                   10                  15

Leu Thr Pro Arg Glu Leu Ala Ser Ala Gly Leu Tyr Tyr Thr Gly Ile
            20                  25                  30

Gly Asp Gln Val Gln Cys Phe Cys Cys Gly Gly Lys Leu Lys Asn Trp
            35                  40                  45

Glu Pro Cys Asp Arg Ala Trp Ser Glu His Arg Arg His Phe Pro Asn
        50                  55                  60

Cys Phe Phe Val
65

<210> SEQ ID NO 22
<211> LENGTH: 67
<212> TYPE: PRT
<213> ORGANISM: Homo sapiens

<400> SEQUENCE: 22

Glu Asn Ala Arg Leu Leu Thr Phe Gln Thr Trp Pro Leu Thr Phe Leu
1               5                   10                  15

Ser Pro Thr Asp Leu Ala Arg Ala Gly Phe Tyr Tyr Ile Gly Pro Gly
            20                  25                  30

Asp Arg Val Ala Cys Phe Ala Cys Gly Gly Lys Leu Ser Asn Trp Glu
            35                  40                  45

Pro Lys Asp Asn Ala Met Ser Glu His Leu Arg His Phe Pro Lys Cys
        50                  55                  60

Pro Phe Ile
65

<210> SEQ ID NO 23
<211> LENGTH: 67
<212> TYPE: PRT
<213> ORGANISM: Homo sapiens

<400> SEQUENCE: 23

Glu Glu Ala Arg Phe Leu Thr Tyr His Met Trp Pro Leu Thr Phe Leu
1               5                   10                  15

Ser Pro Ser Glu Leu Ala Arg Ala Gly Phe Tyr Tyr Ile Gly Pro Gly
            20                  25                  30

Asp Arg Val Ala Cys Phe Ala Cys Gly Gly Lys Leu Ser Asn Trp Glu
        35                  40                  45

Pro Lys Asp Asp Ala Met Ser Glu His Arg Arg His Phe Pro Asn Cys
    50                  55                  60

Pro Phe Leu
65

<210> SEQ ID NO 24
<211> LENGTH: 66
<212> TYPE: PRT
<213> ORGANISM: Mus musculus

<400> SEQUENCE: 24

Tyr Glu Ala Arg Ile Val Thr Phe Gly Thr Trp Ile Tyr Ser Val Asn
1               5                   10                  15

Lys Glu Gln Leu Ala Arg Ala Gly Phe Tyr Ala Leu Gly Glu Gly Asp
            20                  25                  30

Lys Val Lys Cys Phe His Cys Gly Gly Gly Leu Thr Asp Trp Lys Pro
        35                  40                  45

Ser Glu Asp Pro Trp Asp Gln His Ala Lys Cys Tyr Pro Gly Cys Lys
    50                  55                  60

Tyr Leu
65

<210> SEQ ID NO 25
<211> LENGTH: 66
<212> TYPE: PRT
<213> ORGANISM: Homo sapiens

<400> SEQUENCE: 25

Tyr Glu Ala Arg Ile Phe Thr Phe Gly Thr Trp Ile Tyr Ser Val Asn
1               5                   10                  15

Lys Glu Gln Leu Ala Arg Ala Gly Phe Tyr Ala Leu Gly Glu Gly Asp
            20                  25                  30

Lys Val Lys Cys Phe His Cys Gly Gly Gly Leu Thr Asp Trp Lys Pro
        35                  40                  45

Ser Glu Asp Pro Trp Glu Gln His Ala Lys Trp Tyr Pro Gly Cys Lys
    50                  55                  60

Tyr Leu
65

<210> SEQ ID NO 26
<211> LENGTH: 68
<212> TYPE: PRT
<213> ORGANISM: Homo sapiens

<400> SEQUENCE: 26

His Ala Ala Arg Phe Lys Thr Phe Phe Asn Trp Pro Ser Ser Val Leu
1               5                   10                  15

```
Val Asn Pro Glu Gln Leu Ala Ser Ala Gly Phe Tyr Tyr Val Gly Asn
             20                  25                  30

Ser Asp Asp Val Lys Cys Phe Cys Asp Gly Gly Leu Arg Cys Trp
         35                  40                  45

Glu Ser Gly Asp Asp Pro Trp Val Gln His Ala Lys Trp Phe Pro Arg
 50                  55                  60

Cys Glu Tyr Leu
 65

<210> SEQ ID NO 27
<211> LENGTH: 68
<212> TYPE: PRT
<213> ORGANISM: Homo sapiens

<400> SEQUENCE: 27

His Ala Ala Arg Met Arg Thr Phe Met Tyr Trp Pro Ser Ser Val Pro
 1               5                  10                  15

Val Gln Pro Glu Gln Leu Ala Ser Ala Gly Phe Tyr Tyr Val Gly Arg
             20                  25                  30

Asn Asp Asp Val Lys Cys Phe Gly Cys Asp Gly Gly Leu Arg Cys Trp
         35                  40                  45

Glu Ser Gly Asp Asp Pro Trp Val Glu His Ala Lys Trp Phe Pro Arg
 50                  55                  60

Cys Glu Phe Leu
 65

<210> SEQ ID NO 28
<211> LENGTH: 68
<212> TYPE: PRT
<213> ORGANISM: Orgyia pseudotsugata

<400> SEQUENCE: 28

Glu Ala Ala Arg Leu Arg Thr Phe Ala Glu Trp Pro Arg Gly Leu Lys
 1               5                  10                  15

Gln Arg Pro Glu Glu Leu Ala Glu Ala Gly Phe Phe Tyr Thr Gly Gln
             20                  25                  30

Gly Asp Lys Thr Arg Cys Phe Cys Cys Asp Gly Gly Leu Lys Asp Trp
         35                  40                  45

Glu Pro Asp Asp Ala Pro Trp Gln Gln His Ala Arg Trp Tyr Asp Arg
 50                  55                  60

Cys Glu Tyr Val
 65

<210> SEQ ID NO 29
<211> LENGTH: 68
<212> TYPE: PRT
<213> ORGANISM: Cydia pomonella

<400> SEQUENCE: 29

Glu Ala Ala Arg Val Lys Ser Phe His Asn Trp Pro Arg Cys Met Lys
 1               5                  10                  15

Gln Arg Pro Glu Gln Met Ala Asp Ala Gly Phe Phe Tyr Thr Gly Tyr
             20                  25                  30

Gly Asp Asn Thr Lys Cys Phe Tyr Cys Asp Gly Gly Leu Lys Asp Trp
         35                  40                  45

Glu Pro Glu Asp Val Pro Trp Glu Gln His Val Arg Trp Phe Asp Arg
 50                  55                  60

Cys Ala Tyr Val
```

<210> SEQ ID NO 30
<211> LENGTH: 68
<212> TYPE: PRT
<213> ORGANISM: Drosophila melanogaster

<400> SEQUENCE: 30

Val Asp Ala Arg Leu Arg Thr Phe Thr Asp Trp Pro Ile Ser Asn Ile
1               5                   10                  15

Gln Pro Ala Ser Ala Leu Ala Gln Ala Gly Leu Tyr Tyr Gln Lys Ile
            20                  25                  30

Gly Asp Gln Val Arg Cys Phe His Cys Asn Ile Gly Leu Arg Ser Trp
        35                  40                  45

Gln Lys Glu Asp Glu Pro Trp Phe Glu His Ala Lys Trp Ser Pro Lys
    50                  55                  60

Cys Gln Phe Val
65

<210> SEQ ID NO 31
<211> LENGTH: 66
<212> TYPE: PRT
<213> ORGANISM: Drosophila melanogaster

<400> SEQUENCE: 31

Glu Ser Val Arg Leu Ala Thr Phe Gly Glu Trp Pro Leu Asn Ala Pro
1               5                   10                  15

Val Ser Ala Glu Asp Leu Val Ala Asn Gly Phe Phe Gly Thr Trp Met
            20                  25                  30

Glu Ala Glu Cys Asp Phe Cys His Val Arg Ile Asp Arg Trp Glu Tyr
        35                  40                  45

Gly Asp Leu Val Ala Glu Arg His Arg Ser Ser Pro Ile Cys Ser
    50                  55                  60

Met Val
65

<210> SEQ ID NO 32
<211> LENGTH: 46
<212> TYPE: PRT
<213> ORGANISM: Homo sapiens

<400> SEQUENCE: 32

Glu Gln Leu Arg Arg Leu Gln Glu Glu Arg Thr Cys Lys Val Cys Met
1               5                   10                  15

Asp Lys Glu Val Ser Val Val Phe Ile Pro Cys Gly His Leu Val Val
            20                  25                  30

Cys Gln Glu Cys Ala Pro Ser Leu Arg Lys Cys Pro Ile Cys
        35                  40                  45

<210> SEQ ID NO 33
<211> LENGTH: 46
<212> TYPE: PRT
<213> ORGANISM: Homo sapiens

<400> SEQUENCE: 33

Glu Gln Leu Arg Arg Leu Pro Glu Glu Arg Thr Cys Lys Val Cys Met
1               5                   10                  15

Asp Lys Glu Val Ser Ile Val Phe Ile Pro Cys Gly His Leu Val Val
            20                  25                  30

```
Cys Lys Asp Cys Ala Pro Ser Leu Arg Lys Cys Pro Ile Cys
        35                  40                  45
```

<210> SEQ ID NO 34
<211> LENGTH: 46
<212> TYPE: PRT
<213> ORGANISM: Mus musculus

<400> SEQUENCE: 34

```
Glu Gln Leu Arg Arg Leu Gln Glu Glu Lys Leu Ser Lys Ile Cys Met
 1               5                  10                  15

Asp Arg Asn Ile Ala Ile Val Phe Phe Pro Cys Gly His Leu Ala Thr
            20                  25                  30

Cys Lys Gln Cys Ala Glu Ala Val Asp Lys Cys Pro Met Cys
        35                  40                  45
```

<210> SEQ ID NO 35
<211> LENGTH: 46
<212> TYPE: PRT
<213> ORGANISM: Homo sapiens

<400> SEQUENCE: 35

```
Glu Gln Leu Arg Arg Leu Gln Glu Glu Lys Leu Cys Lys Ile Cys Met
 1               5                  10                  15

Asp Arg Asn Ile Ala Ile Val Phe Val Pro Cys Gly His Leu Val Thr
            20                  25                  30

Cys Lys Gln Cys Ala Glu Ala Val Asp Lys Cys Pro Met Cys
        35                  40                  45
```

<210> SEQ ID NO 36
<211> LENGTH: 46
<212> TYPE: PRT
<213> ORGANISM: Drosophila melanogaster

<400> SEQUENCE: 36

```
Glu Glu Asn Arg Gln Leu Lys Asp Ala Arg Leu Cys Lys Val Cys Leu
 1               5                  10                  15

Asp Glu Glu Val Gly Val Val Phe Leu Pro Cys Gly His Leu Ala Thr
            20                  25                  30

Cys Asn Gln Cys Ala Pro Ser Val Ala Asn Cys Pro Met Cys
        35                  40                  45
```

<210> SEQ ID NO 37
<211> LENGTH: 46
<212> TYPE: PRT
<213> ORGANISM: Cydia pomonella

<400> SEQUENCE: 37

```
Glu Lys Glu Pro Gln Val Glu Asp Ser Lys Leu Cys Lys Ile Cys Tyr
 1               5                  10                  15

Val Glu Glu Cys Ile Val Cys Phe Val Pro Cys Gly His Val Val Ala
            20                  25                  30

Cys Ala Lys Cys Ala Leu Ser Val Asp Lys Cys Pro Met Cys
        35                  40                  45
```

<210> SEQ ID NO 38
<211> LENGTH: 46
<212> TYPE: PRT
<213> ORGANISM: Orgyia pseudotsugata

<400> SEQUENCE: 38

```
Ala Val Glu Ala Glu Val Ala Asp Asp Arg Leu Cys Lys Ile Cys Leu
1               5                   10                  15

Gly Ala Glu Lys Thr Val Cys Phe Val Pro Cys Gly His Val Val Ala
            20                  25                  30

Cys Gly Lys Cys Ala Ala Gly Val Thr Thr Cys Pro Val Cys
        35                  40                  45

<210> SEQ ID NO 39
<211> LENGTH: 2474
<212> TYPE: DNA
<213> ORGANISM: Mus musculus

<400> SEQUENCE: 39
```

| | | | | | |
|---|---|---|---|---|---|
| gaattccggg | agacctacac | ccccggagat | cagaggtcat | tgctggcgtt | cagagcctag | 60
| gaagtgggct | gcggtatcag | cctagcagta | aaaccgacca | gaagccatgc | acaaaactac | 120
| atccccagag | aaagacttgt | cccttcccct | ccctgtcatc | tcaccatgaa | catggttcaa | 180
| gacagcgcct | ttctagccaa | gctgatgaag | agtgctgaca | cctttgagtt | gaagtatgac | 240
| ttttcctgtg | agctgtaccg | attgtccacg | tattcagctt | ttcccagggg | agttcctgtg | 300
| tcagaaagga | gtctggctcg | tgctggcttt | tactacactg | gtgccaatga | caaggtcaag | 360
| tgcttctgct | gtggcctgat | gctagacaac | tggaaacaag | gggacagtcc | catggagaag | 420
| cacagaaagt | tgtaccccag | ctgcaacttt | gtacagactt | tgaatccagc | caacagtctg | 480
| gaagctagtc | ctcggccttc | tcttccttcc | acggcgatga | gcaccatgcc | tttgagcttt | 540
| gcaagttctg | agaatactgg | ctatttcagt | ggctcttact | cgagctttcc | ctcagaccct | 600
| gtgaacttcc | gagcaaatca | agattgtcct | gctttgagca | caagtcccta | ccactttgca | 660
| atgaacacag | agaaggccag | attactcacc | tatgaaacat | ggccattgtc | ttttctgtca | 720
| ccagcaaagc | tggccaaagc | aggcttctac | tacataggac | ctggagatag | agtggcctgc | 780
| tttgcgtgcg | atgggaaact | gagcaactgg | gaacgtaagg | atgatgctat | gtcagagcac | 840
| cagaggcatt | tccccagctg | tccgttctta | aaagacttgg | gtcagtctgc | ttcgagatac | 900
| actgtctcta | acctgagcat | gcagacacac | gcagcccgta | ttagaacatt | ctctaactgg | 960
| ccttctagtg | cactagttca | ttcccaggaa | cttgcaagtg | cgggctttta | ttatacagga | 1020
| cacagtgatg | atgtcaagtg | tttatgctgt | gatggtgggc | tgaggtgctg | ggaatctgga | 1080
| gatgacccct | gggtggaaca | tgccaagtgg | tttccaaggt | gtgagtactt | gctcagaatc | 1140
| aaaggccaag | aatttgtcag | ccaagttcaa | gctggctatc | ctcatctact | tgagcagcta | 1200
| ttatctacgt | cagactcccc | agaagatgag | aatgcagacg | cagcaatcgt | gcattttggc | 1260
| cctggagaaa | gttcggaaga | tgtcgtcatg | atgagcacgc | ctgtggttaa | agcagccttg | 1320
| gaaatgggct | tcagtaggag | cctggtgaga | cagacggttc | agtggcagat | cctggccact | 1380
| ggtgagaact | acaggaccgt | cagtgacctc | gttataggct | tactcgatgc | agaagacgag | 1440
| atgagagagg | agcagatgga | gcaggcggcc | gaggaggagg | agtcagatga | tctagcacta | 1500
| atccggaaga | acaaaatggt | gcttttccaa | catttgacgt | gtgtgacacc | aatgctgtat | 1560
| tgcctcctaa | gtgcaagggc | catcactgaa | caggagtgca | atgctgtgaa | acagaaacca | 1620
| cacaccttac | aagcaagcac | actgattgat | actgtgttag | caaaaggaaa | cactgcagca | 1680
| acctcattca | gaaactccct | tcgggaaatt | gaccctgcgt | tatacagaga | tatatttgtg | 1740
| caacaggaca | ttaggagtct | tcccacagat | gacattgcag | ctctaccaat | ggaagaacag | 1800
| ttgcggcccc | tcccggagga | cagaatgtgt | aaagtgtgta | tggaccgaga | ggtatccatc | 1860

-continued

```
gtgttcattc cctgtggcca tctggtcgtg tgcaaagact gcgctccctc tctgaggaag    1920
tgtcccatct gtagagggac catcaagggc acagtgcgca catttctctc ctgaacaaga    1980
ctaatggtcc atggctgcaa cttcagccag gaggaagttc actgtcactc ccagttccat    2040
tcggaacttg aggccagcct ggatagcacg agacaccgcc aaacacacaa atataaacat    2100
gaaaactttt tgtctgaagt caagaatgaa tgaattactt atataataat tttaattggt    2160
ttccttaaaa gtgctatttg ttcccaactc agaaaattgt tttctgtaaa catatttaca    2220
tactacctgc atctaaagta ttcatatatt catatattca gatgtcatga gagagggttt    2280
tgttcttgtt cctgaaaagc tggtttatca tctgatcagc atatactgcg caacgggcag    2340
ggctagaatc catgaaccaa gctgcaaaga tctcacgcta ataaggcgg aaagatttgg    2400 agaaacgaaa ggaaattctt tcctgtccaa tgtatactct tcagactaat gacctcttcc    2460
tatcaagcct tcta                                                       2474
```

<210> SEQ ID NO 40
<211> LENGTH: 602
<212> TYPE: PRT
<213> ORGANISM: Mus musculus

<400> SEQUENCE: 40

```
Met Asn Met Val Gln Asp Ser Ala Phe Leu Ala Lys Leu Met Lys Ser
 1               5                  10                  15

Ala Asp Thr Phe Glu Leu Lys Tyr Asp Phe Ser Cys Glu Leu Tyr Arg
                20                  25                  30

Leu Ser Thr Tyr Ser Ala Phe Pro Arg Gly Val Pro Val Ser Glu Arg
            35                  40                  45

Ser Leu Ala Arg Ala Gly Phe Tyr Tyr Thr Gly Ala Asn Asp Lys Val
        50                  55                  60

Lys Cys Phe Cys Cys Gly Leu Met Leu Asp Asn Trp Lys Gln Gly Asp
65                  70                  75                  80

Ser Pro Met Glu Lys His Arg Lys Leu Tyr Pro Ser Cys Asn Phe Val
                85                  90                  95

Gln Thr Leu Asn Pro Ala Asn Ser Leu Glu Ala Ser Pro Arg Pro Ser
            100                 105                 110

Leu Pro Ser Thr Ala Met Ser Thr Met Pro Leu Ser Phe Ala Ser Ser
        115                 120                 125

Glu Asn Thr Gly Tyr Phe Ser Gly Ser Tyr Ser Ser Phe Pro Ser Asp
    130                 135                 140

Pro Val Asn Phe Arg Ala Asn Gln Asp Cys Pro Ala Leu Ser Thr Ser
145                 150                 155                 160

Pro Tyr His Phe Ala Met Asn Thr Glu Lys Ala Arg Leu Leu Thr Tyr
                165                 170                 175

Glu Thr Trp Pro Leu Ser Phe Leu Ser Pro Ala Lys Leu Ala Lys Ala
            180                 185                 190

Gly Phe Tyr Tyr Ile Gly Pro Gly Asp Arg Val Ala Cys Phe Ala Cys
        195                 200                 205

Asp Gly Lys Leu Ser Asn Trp Glu Arg Lys Asp Asp Ala Met Ser Glu
    210                 215                 220

His Gln Arg His Phe Pro Ser Cys Pro Phe Leu Lys Asp Leu Gly Gln
225                 230                 235                 240

Ser Ala Ser Arg Tyr Thr Val Ser Asn Leu Ser Met Gln Thr His Ala
                245                 250                 255

Ala Arg Ile Arg Thr Phe Ser Asn Trp Pro Ser Ser Ala Leu Val His
```

|  |  |  |  |  | 260 |  |  |  |  | 265 |  |  |  |  | 270 |  |  |
|---|---|---|---|---|---|---|---|---|---|---|---|---|---|---|---|---|---|
| Ser | Gln | Glu | Leu | Ala | Ser | Ala | Gly | Phe | Tyr | Tyr | Thr | Gly | His | Ser | Asp |
|  |  |  | 275 |  |  |  |  | 280 |  |  |  |  | 285 |  |  |
| Asp | Val | Lys | Cys | Leu | Cys | Cys | Asp | Gly | Gly | Leu | Arg | Cys | Trp | Glu | Ser |
|  | 290 |  |  |  |  | 295 |  |  |  |  | 300 |  |  |  |  |
| Gly | Asp | Asp | Pro | Trp | Val | Glu | His | Ala | Lys | Trp | Phe | Pro | Arg | Cys | Glu |
| 305 |  |  |  |  | 310 |  |  |  |  | 315 |  |  |  |  | 320 |
| Tyr | Leu | Leu | Arg | Ile | Lys | Gly | Gln | Glu | Phe | Val | Ser | Gln | Val | Gln | Ala |
|  |  |  |  | 325 |  |  |  |  | 330 |  |  |  |  | 335 |  |
| Gly | Tyr | Pro | His | Leu | Leu | Glu | Gln | Leu | Leu | Ser | Thr | Ser | Asp | Ser | Pro |
|  |  |  | 340 |  |  |  |  | 345 |  |  |  |  | 350 |  |  |
| Glu | Asp | Glu | Asn | Ala | Asp | Ala | Ala | Ile | Val | His | Phe | Gly | Pro | Gly | Glu |
|  |  | 355 |  |  |  |  | 360 |  |  |  |  | 365 |  |  |  |
| Ser | Ser | Glu | Asp | Val | Val | Met | Met | Ser | Thr | Pro | Val | Val | Lys | Ala | Ala |
|  | 370 |  |  |  |  | 375 |  |  |  |  | 380 |  |  |  |  |
| Leu | Glu | Met | Gly | Phe | Ser | Arg | Ser | Leu | Val | Arg | Gln | Thr | Val | Gln | Trp |
| 385 |  |  |  |  | 390 |  |  |  |  | 395 |  |  |  |  | 400 |
| Gln | Ile | Leu | Ala | Thr | Gly | Glu | Asn | Tyr | Arg | Thr | Val | Ser | Asp | Leu | Val |
|  |  |  |  | 405 |  |  |  |  | 410 |  |  |  |  | 415 |  |
| Ile | Gly | Leu | Leu | Asp | Ala | Glu | Asp | Glu | Met | Arg | Glu | Glu | Gln | Met | Glu |
|  |  |  | 420 |  |  |  |  | 425 |  |  |  |  | 430 |  |  |
| Gln | Ala | Ala | Glu | Glu | Glu | Ser | Asp | Asp | Leu | Ala | Leu | Ile | Arg | Lys |  |
|  |  | 435 |  |  |  |  | 440 |  |  |  |  | 445 |  |  |  |
| Asn | Lys | Met | Val | Leu | Phe | Gln | His | Leu | Thr | Cys | Val | Thr | Pro | Met | Leu |
|  | 450 |  |  |  |  | 455 |  |  |  |  | 460 |  |  |  |  |
| Tyr | Cys | Leu | Leu | Ser | Ala | Arg | Ala | Ile | Thr | Glu | Gln | Glu | Cys | Asn | Ala |
| 465 |  |  |  |  | 470 |  |  |  |  | 475 |  |  |  |  | 480 |
| Val | Lys | Gln | Lys | Pro | His | Thr | Leu | Gln | Ala | Ser | Thr | Leu | Ile | Asp | Thr |
|  |  |  |  | 485 |  |  |  |  | 490 |  |  |  |  | 495 |  |
| Val | Leu | Ala | Lys | Gly | Asn | Thr | Ala | Ala | Thr | Ser | Phe | Arg | Asn | Ser | Leu |
|  |  |  | 500 |  |  |  |  | 505 |  |  |  |  | 510 |  |  |
| Arg | Glu | Ile | Asp | Pro | Ala | Leu | Tyr | Arg | Asp | Ile | Phe | Val | Gln | Gln | Asp |
|  | 515 |  |  |  |  | 520 |  |  |  |  | 525 |  |  |  |  |
| Ile | Arg | Ser | Leu | Pro | Thr | Asp | Asp | Ile | Ala | Ala | Leu | Pro | Met | Glu | Glu |
|  | 530 |  |  |  |  | 535 |  |  |  |  | 540 |  |  |  |  |
| Gln | Leu | Arg | Pro | Leu | Pro | Glu | Asp | Arg | Met | Cys | Lys | Val | Cys | Met | Asp |
| 545 |  |  |  |  | 550 |  |  |  |  | 555 |  |  |  |  | 560 |
| Arg | Glu | Val | Ser | Ile | Val | Phe | Ile | Pro | Cys | Gly | His | Leu | Val | Val | Cys |
|  |  |  |  | 565 |  |  |  |  | 570 |  |  |  |  | 575 |  |
| Lys | Asp | Cys | Ala | Pro | Ser | Leu | Arg | Lys | Cys | Pro | Ile | Cys | Arg | Gly | Thr |
|  |  |  | 580 |  |  |  |  | 585 |  |  |  |  | 590 |  |  |
| Ile | Lys | Gly | Thr | Val | Arg | Thr | Phe | Leu | Ser |  |  |  |  |  |  |
|  |  |  | 595 |  |  |  |  | 600 |  |  |  |  |  |  |  |

<210> SEQ ID NO 41
<211> LENGTH: 2416
<212> TYPE: DNA
<213> ORGANISM: Mus musculus

<400> SEQUENCE: 41

| ctgtggtgga gatctattgt ccaagtggtg agaaacttca tctggaagtt taagcggtca | 60 |
|---|---|
| gaaatactat tactactcat ggacaaaact gtctcccaga gactcgccca aggtaccttt | 120 |
| cacccaaaaa cttaaacgta taatggagaa gagcacaatc ttgtcaaatt ggacaaagga | 180 |

```
gagcgaagaa aaaatgaagt ttgacttttc gtgtgaactc taccgaatgt ctacatattc    240
agcttttccc aggggagttc ctgtctcaga gaggagtctg gctcgtgctg gcttttatta    300
tacaggtgtg aatgacaaag tcaagtgctt ctgctgtggc ctgatgttgg ataactggaa    360 acaagggac agtcctgttg aaaagcacag acagttctat cccagctgca gctttgtaca     420
gactctgctt tcagccagtc tgcagtctcc atctaagaat atgtctcctg tgaaaagtag    480
atttgcacat tcgtcacctc tggaacgagg tggcattcac tccaacctgt gctctagccc    540
tcttaattct agagcagtgg aagacttctc atcaaggatg gatccctgca gctatgccat    600
gagtacagaa gaggccagat ttcttactta cagtatgtgg cctttaagtt ttctgtcacc    660
agcagagctg ccagagctg gcttctatta catagggcct ggagacaggg tggcctgttt     720
tgcctgtggt gggaaactga gcaactggga accaaaggat tatgctatgt cagagcaccg    780
cagacatttt ccccactgtc catttctgga aaatacttca gaaacacaga ggtttagtat    840
atcaaatcta gtatgcaga cacactctgc tcgattgagg acatttctgt actggccacc      900
tagtgttcct gttcagcccg agcagcttgc aagtgctgga ttctattacg tggatcgcaa    960
tgatgatgtc aagtgccttt gttgtgatgg tggcttgaga tgttgggaac ctggagatga   1020 ccctggata gaacacgcca atggttttcc aaggtgtgag ttcttgatac ggatgaaggg     1080
tcaggagttt gttgatgaga ttcaagctag atatcctcat cttcttgagc agctgttgtc    1140
cacttcagac accccaggag aagaaaatgc tgaccctaca gagacagtgg tgcattttgg    1200 ccctggaaa agttcgaaag atgtcgtcat gatgagcacg cctgtggtta agcagccttt     1260
ggaaatgggc ttcagtagga gcctggtgag acagacggtt cagcggcaga tcctggccac    1320
tggtgagaac tacaggaccg tcaatgatat tgtctcagta cttttgaatg ctgaagatga    1380
gagaagagaa gaggagaagg aaagacagac tgaagagatg gcatcaggtg acttatcact    1440
gattcggaag aatagaatgg ccctctttca acagttgaca catgtccttc ctatcctgga    1500
taatcttctt gaggccagtg taattacaaa acaggaacat gatattatta gacagaaaac    1560
acagataccc ttacaagcaa gagagcttat tgacaccgtt ttagtcaagg gaaatgctgc    1620
agccaacatc ttcaaaaact ctctgaaggg aattgactcc acgttatatg aaaacttatt    1680
tgtggaaaag aatatgaagt atattccaac agaagacgtt tcaggcttgt cattggaaga    1740
gcagttgcgg agattacaag aagaacgaac ttgcaaagtg tgtatggaca gagaggtttc    1800
tattgtgttc attccgtgtg gtcatctagt agtctgccag gaatgtgccc cttctctaag    1860
gaagtgcccc atctgcaggg ggacaatcaa ggggactgtg cgcacatttc tctcatgagt    1920
gaagaatggt ctgaaagtat tgttggacat cagaagctgt cagaacaaag aatgaactac    1980
tgatttcagc tcttcagcag gacattctac tctctttcaa gattagtaat cttgctttat    2040
gaagggtagc attgtatatt taagcttagt ctgttgcaag ggaaggtcta tgctgttgag    2100
ctacaggact gtgtctgttc cagagcagga gttgggatgc ttgctgtatg tccttcagga    2160
cttcttggga tttgggaatt tggggaaagc tttggaatcc agtgatgtgg agctcagaaa    2220
tcctggaacc agtgactctg gtactcagta gatagggtac cctgtacttc ttggtgcttt    2280
tccagtctgg gaaataagga ggaatctgct gctggtaaaa atttgctgga tgtgagaaat    2340
agatgaaagt gtttcgggtg ggggcgtgca tcagtgtagt gtgtgcaggg atgtatgcag    2400
gccaaacact gtgtag                                                   2416
```

<210> SEQ ID NO 42
<211> LENGTH: 591

```
<212> TYPE: PRT
<213> ORGANISM: Mus musculus

<400> SEQUENCE: 42

Met Glu Lys Ser Thr Ile Leu Ser Asn Trp Thr Lys Glu Ser Glu
 1               5                  10                  15

Lys Met Lys Phe Asp Phe Ser Cys Glu Leu Tyr Arg Met Ser Thr Tyr
                20                  25                  30

Ser Ala Phe Pro Arg Gly Val Pro Val Ser Glu Arg Ser Leu Ala Arg
            35                  40                  45

Ala Gly Phe Tyr Tyr Thr Gly Val Asn Asp Lys Val Lys Cys Phe Cys
        50                  55                  60

Cys Gly Leu Met Leu Asp Asn Trp Lys Gln Gly Asp Ser Pro Val Glu
65                  70                  75                  80

Lys His Arg Gln Phe Tyr Pro Ser Cys Ser Phe Val Gln Thr Leu Leu
                85                  90                  95

Ser Ala Ser Leu Gln Ser Pro Ser Lys Asn Met Ser Pro Val Lys Ser
            100                 105                 110

Arg Phe Ala His Ser Ser Pro Leu Glu Arg Gly Gly Ile His Ser Asn
            115                 120                 125

Leu Cys Ser Ser Pro Leu Asn Ser Arg Ala Val Glu Asp Phe Ser Ser
        130                 135                 140

Arg Met Asp Pro Cys Ser Tyr Ala Met Ser Thr Glu Glu Ala Arg Phe
145                 150                 155                 160

Leu Thr Tyr Ser Met Trp Pro Leu Ser Phe Leu Ser Pro Ala Glu Leu
                165                 170                 175

Ala Arg Ala Gly Phe Tyr Tyr Ile Gly Pro Gly Asp Arg Val Ala Cys
            180                 185                 190

Phe Ala Cys Gly Gly Lys Leu Ser Asn Trp Glu Pro Lys Asp Tyr Ala
        195                 200                 205

Met Ser Glu His Arg Arg His Phe Pro His Cys Pro Phe Leu Glu Asn
        210                 215                 220

Thr Ser Glu Thr Gln Arg Phe Ser Ile Ser Asn Leu Ser Met Gln Thr
225                 230                 235                 240

His Ser Ala Arg Leu Arg Thr Phe Leu Tyr Trp Pro Pro Ser Val Pro
                245                 250                 255

Val Gln Pro Glu Gln Leu Ala Ser Ala Gly Phe Tyr Tyr Val Asp Arg
            260                 265                 270

Asn Asp Asp Val Lys Cys Leu Cys Cys Asp Gly Gly Leu Arg Cys Trp
            275                 280                 285

Glu Pro Gly Asp Asp Pro Trp Ile Glu His Ala Lys Trp Phe Pro Arg
290                 295                 300

Cys Glu Phe Leu Ile Arg Met Lys Gly Gln Glu Phe Val Asp Glu Ile
305                 310                 315                 320

Gln Ala Arg Tyr Pro His Leu Leu Glu Gln Leu Leu Ser Thr Ser Asp
                325                 330                 335

Thr Pro Gly Glu Glu Asn Ala Asp Pro Thr Glu Thr Val His Phe
            340                 345                 350

Gly Pro Gly Glu Ser Ser Lys Asp Val Val Met Met Ser Thr Pro Val
            355                 360                 365

Val Lys Ala Ala Leu Glu Met Gly Phe Ser Arg Ser Leu Val Arg Gln
        370                 375                 380

Thr Val Gln Arg Gln Ile Leu Ala Thr Gly Glu Asn Tyr Arg Thr Val
385                 390                 395                 400
```

-continued

```
Asn Asp Ile Val Ser Val Leu Leu Asn Ala Glu Asp Glu Arg Arg Glu
                405                 410                 415
Glu Glu Lys Glu Arg Gln Thr Glu Glu Met Ala Ser Gly Asp Leu Ser
            420                 425                 430
Leu Ile Arg Lys Asn Arg Met Ala Leu Phe Gln Gln Leu Thr His Val
        435                 440                 445
Leu Pro Ile Leu Asp Asn Leu Leu Glu Ala Ser Val Ile Thr Lys Gln
    450                 455                 460
Glu His Asp Ile Ile Arg Gln Lys Thr Gln Ile Pro Leu Gln Ala Arg
465                 470                 475                 480
Glu Leu Ile Asp Thr Val Leu Val Lys Gly Asn Ala Ala Ala Asn Ile
                485                 490                 495
Phe Lys Asn Ser Leu Lys Gly Ile Asp Ser Thr Leu Tyr Glu Asn Leu
            500                 505                 510
Phe Val Glu Lys Asn Met Lys Tyr Ile Pro Thr Glu Asp Val Ser Gly
        515                 520                 525
Leu Ser Leu Glu Glu Gln Leu Arg Arg Leu Gln Glu Glu Arg Thr Cys
    530                 535                 540
Lys Val Cys Met Asp Arg Glu Val Ser Ile Val Phe Ile Pro Cys Gly
545                 550                 555                 560
His Leu Val Val Cys Gln Glu Cys Ala Pro Ser Leu Arg Lys Cys Pro
                565                 570                 575
Ile Cys Arg Gly Thr Ile Lys Gly Thr Val Arg Thr Phe Leu Ser
            580                 585                 590

<210> SEQ ID NO 43
<211> LENGTH: 11
<212> TYPE: PRT
<213> ORGANISM: Artificial Sequence
<220> FEATURE:
<223> OTHER INFORMATION: Synthetic based on viral sequence

<400> SEQUENCE: 43

Met Glu Gln Lys Leu Ile Ser Glu Glu Asp Leu
1               5                   10

<210> SEQ ID NO 44
<211> LENGTH: 21
<212> TYPE: DNA
<213> ORGANISM: Artificial Sequence
<220> FEATURE:
<223> OTHER INFORMATION: Synthetic primer based on Homo sapiens

<400> SEQUENCE: 44
agtgcgggtt tttattatgt g                                       21

<210> SEQ ID NO 45
<211> LENGTH: 25
<212> TYPE: DNA
<213> ORGANISM: Artificial Sequence
<220> FEATURE:
<223> OTHER INFORMATION: Synthetic primer based on Homo sapiens

<400> SEQUENCE: 45
agatgaccac aaggaataaa cacta                                   25
```

What is claimed is:

1. A substantially pure polypeptide consisting of a BIR-3 domain having at least 95% sequence identity to SEQ ID NO:24 or SEQ ID NO:25, wherein said polypeptide is capable of inhibiting apoptosis of a mammalian cell when said polypeptide is expressed in said cell.

2. The polypeptide of claim 1, wherein said polypeptide has at least 95% sequence identity to SEQ ID NO: 24.

3. The polypeptide of claim 1, wherein said polypeptide has at least 95% sequence identity to SEQ ID NO: 25.

4. A substantially pure polypeptide consisting of SEQ ID NO:24 or SEQ ID NO:25, wherein said polypeptide is capable of inhibiting apoptosis of a mammalian cell when said polypeptide is expressed in said cell.

5. The polypeptide of claim 4, wherein said polypeptide has the sequence of SEQ ID NO: 24.

6. The polypeptide of claim 4, wherein said polypeptide has the sequence of SEQ ID NO: 25.

7. A substantially pure polypeptide comprising SEQ ID NO:24 or SEQ ID NO:25, wherein said polypeptide is capable of inhibiting apoptosis of a mammalian cell when said polypeptide is expressed in said cell.

8. The polypeptide of claim 7, wherein said polypeptide comprises the sequence of SEQ ID NO: 24.

9. The polypeptide of claim 7, wherein said polypeptide comprises the sequence of SEQ ID NO: 25.

* * * * *